US007794980B2

(12) United States Patent
Pietrokovski et al.

(10) Patent No.: US 7,794,980 B2
(45) Date of Patent: Sep. 14, 2010

(54) CHIMERIC AUTOPROCESSING POLYPEPTIDES AND USES THEREOF

(75) Inventors: Shmuel Pietrokovski, Rehovot (IL); Gil Amitai, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 1094 days.

(21) Appl. No.: 10/534,544

(22) PCT Filed: Nov. 12, 2003

(86) PCT No.: PCT/IL03/00956

§ 371 (c)(1),
(2), (4) Date: May 10, 2005

(87) PCT Pub. No.: WO2004/043997

PCT Pub. Date: May 27, 2004

(65) Prior Publication Data

US 2006/0183121 A1 Aug. 17, 2006

Related U.S. Application Data

(60) Provisional application No. 60/425,295, filed on Nov. 12, 2002.

(51) Int. Cl.
| | |
|---|---|
| *C12P 21/04* | (2006.01) |
| *C12P 21/06* | (2006.01) |
| *C12N 1/20* | (2006.01) |
| *C12N 15/00* | (2006.01) |
| *C07K 14/00* | (2006.01) |
| *C08H 1/00* | (2006.01) |
| *A23J 1/00* | (2006.01) |

(52) U.S. Cl. .................. 435/69.7; 435/69.1; 435/252.3; 435/320.1; 530/350; 530/402; 530/412

(58) Field of Classification Search ........................ None
See application file for complete search history.

(56) References Cited

OTHER PUBLICATIONS

Nabedryk et al Biochemistry 2000,39,14654-14663.*
Jarvik et al Anu. Rev. Genet. 1998, 32:601-18.*
Ng et al. Genome Research May 2001; 11 (5): 863-874.*
Bowie et al. Science vol. 247, No. 4948, p. 1306-1310,1990.*
Burgess et al. The Journal of Cell Biology, vol. 111, Nov. 1990 2129-2138.*
Lazar et al. Molecular and Cellular Biology, Mar. 1988, p. 1247-1252.*
Amitai et al. "Distribution and Function of New Bacterial Intein-Like Protein Domains", Molecular Microbiology, 47(1): 61-73, 2003.
Fraser et al. "Novel Neisserial Polypeptides Predicted to Be Useful Antigens for Vaccines and Diagnostics", Database EMBL 'Online!, No. AAY75498, 2000.
Zhang et al "Construction of a Mini-Intein Fusion System to Allow Both Direct Monitoring of Soluble Protein Expression and Rapid Purification of Target Proteins", Gene, 275(2): 241-252, 2001. p. 250, 1-h col., § 3-p. 251, r-h col., § 1, Figs.1, 3.
Humphries et al. "Expression of the Class 1 Outer-Membrane Protein of *Neisseria meningitidis* in *Escherichia coli* and Purification Using a Self-Cleavable Affinity Tag", Protein Expression and Purification, 26(2): 243-248, 2002. p. 247, r-h col., § 2-p. 248, 1-h col., § 2, Fig.1.
Aspöck et al. "*Caenorhabditis elegans* Has Scores of Hedgehog-Related Genes: Sequence and Expression Analysis", Genome Research, 9(10): 909-923, 1999.
Pietrokovski "Intein Spread and Extinction in Evolution", Trends in Genetics 17(8): 465-472, 2001.
Buell et al. "Filamentous Hemagglutinin, Intein-Containing, Putative", Database Trembl 'Online!, No. Q880E1, 2003.
Brown et al. "Hypothetical Protein SCP1.201", Database Trembl 'Online!, No. Q9ACV2, 2003.
Ren "Probable Phenazine Biosynthesis Family Protein", Database Trembl 'Online!, No. Q8EZX6, 2003.
Gloeckner et al. "Hypothetical Protein RB6107", Database Trembl 'Online!, No. Q7UQT4, 2003.
Omura et al. "Hypothetical Protein SAV200", Database Trembl. 'Online!, No. Q82RE3, 2003.
Omura et al. "Hypothetical Protein SAV286", Database Trembl. 'Online!, No. Q82R58, 2003.
Omura et al. "Hypothetical Protein SAV5292", Database Trembl 'Online!, No. Q82CQ1, 2003.
Ren "Hypothetical Protein LA3719", Database Trembl 'Online!, No. Q8EZY2, 2003.
Dassa et al. "Protein Splicing and Auto-Cleavage of Bacterial Intein-Like Domains Lacking A C'-Flanking Nucleophilic Residue", The Journal of Biological Chemistry, 279(31): 32001-32007, 2004.
Dassa et al. "New Type of Polyubiquitin-Like Genes With Intein-Like Autoprocessing Domains", Trends in Genetics, 20(11): 538-542, 2004.
Southworth et al. "Rescue of Protein Splicing Activity From a Magnetospirillum Magnetotacticum Intein-Like Element", Biochemical Society Transactions, 32(Part 2): 250-254, 2004.
Dassa et al. "Origin and Evolution of Inteins and Other Hint Domains", Nucleic Acids and Molecular Biology, 16: 209-229, 2005.
Belfort et al. "Homing Endonucleases: Keeping the House in Order", Nucleic Acids Research, 25(17): 3379-3388, 1997.
Bürglin "Warthog and Groundhog, Novel Families Related to Hedgehog", Current Biology, 6(9): 1047-1950, 1996.
Cattoli et al. "Separation of MBP Fusion Proteins Through Affinity Membranes", Biotechnological Progresses, 18(1): 94-100, 2002.
Chong et al. "Protein Splicing Involving the *Saccharomyces cerevisiae* VMA Intein", The Journal of Biological Chemistry, 271(36): 22159-22168, 1996.
Chong et al. "Single-Column Purification of Free Recombinant Proteins Using A Self-Cleavable Affinity Tag Derived From A Protein Splicing Element", Gene, 192: 271-281, 1997.

(Continued)

*Primary Examiner*—Robert Mondesi
*Assistant Examiner*—Oluwatosin Ogunbiyi

(57) ABSTRACT

A chimeric polypeptide comprising an autoprocessing segment having an amino acid sequence being capable of auto-cleavage, a polynucleotide encoding such a polypeptide, and uses of such a polypeptide and such a polynucleotide are provided.

15 Claims, 21 Drawing Sheets

OTHER PUBLICATIONS

Chong et al. "Protein Splicing of the *Saccharomyces cerevisiae* VMA Intein Without the Endonuclease Motifs", The Journal of Biological Chemistry, 272(25): 15587-15590, 1997.

Chong et al. "Modulation of Protein Splicing of the *Saccharomyces cerevisiae* Vacuolar Membrane ATPase Intein", The Journal of Biological Chemistry, 273(17): 10567-10577, 1998.

Chong et al. "Utilizing the C-Terminal Cleavage Activity of A Prtoein Splicing Element to Purify Recombinant Proteins in a Single Chromatographic Step", Nucleic Acids Research, 26(22): 5109-5115, 1998.

Clonis "High-Performance Affinity Chromatography (HPAC)", HPLC of Macromolecules: A Practical Approach, IRL Press, Chap.6: 157-182, 1989.

Coote "Structural and Functional Relationships Among the RTX Toxin Determinants of Gram-Negative Bacteria", FEMS Microbiology Reviews, 88: 137-162, 1992.

Dalgaard et al. "Statistical Modeling, Phylogenetic Analysis and Structure Prediction of a Protein Splicing Domain Common to Inteins and Hedgehog Proteins", Journal of Computational Biology, 4(2): 193-214, 1997.

Derbyshire et al. "Genetic Definition of A Protein-Splicing Domain: Functional Mini-Inteins Support Structure Predictions and a Model for Intein Evolution", Proc. Natl. Acad. Sci. USA, 94: 11466-11471, 1997.

Fouts et al. "Genomewide Identification of *Pseudomonas syringae* Pv. Tomato DC3000 Promoters Controlled by the HrpL Alternative Sigma Factor", Proc. Natl. Acad. Sci. USA, 99(4): 2275-2280, 2002.

Gimble et al. "Homing of a DNA Endonuclease Gene by Meiotic Gene Conversion in *Saccharomyces cerevisiae*", Nature, 357(6376): 301-306, 1992.

Guan et al. "Production of Extracellular Domain of Human Tissue Factor Using Maltose-Binding Protein Fusion System", Protein Expression and Purification, 26: 229-234, 2002.

Tanaka Hall et al. "Crystal Structure of a Hedgehog Autoprocessing Domain: Homology Between Hedgehog and Self-Splicing Proteins", Cell, 91: 85-97, 1997.

Hammerschmidt et al. "The World According to Hedgehog", Trends in Genetics, 13(1): 14-21, 1997.

Haselkorn et al. "The Rhodobacter Capsulatus Genome", Photosynthesis Research, 70: 43-52, 2001.

Hirata et al. "Molecular Structure of a Gene, VMA1, Encoding the Catalytic Subunit of H+-Translocating Adenosine Triphosphatase From Vacuolar Membranes of *Saccharomyces cerevisiae*", The Jornal of Biological Chemistry, 265(12): 6726-6733, 1990.

Jack "Immunoaffinity Chromatography", Molecular Biotechnology, 1: 59-86, 1994.

James et al. "The Biology of E Colicins: Paradigms and Paradoxes", Microbiology, 142: 1569-1580, 1996.

Janson et al. "Packings in Affinity Chromatography", Techniques, p. 747-781, 1990.

Jensen et al. "Delayed Extraction Improves Specificity in Database Searches by Matrix-Assisted Laser Desorption/Ionization Peptide Maps", Rapid Communications in Mass Spectrometry, 10: 1371-1378, 1996.

Kane et al. "Protein Splicing Converts the Yeast TFP1 Gene Product to the 69-KD Subunit of the Vacuolar H$ +$-Adenosine Triphosphatase", Science, 250(4981): 651-657, 1990.

Kaufmann et al. "Crystal Structure of the Anti-His Tag Antibody 3D5 Single-Chain Fragment Complexed to Its Antigen", Journal of Molecular Biology, 318: 135-147, 2002.

Kussmann et al. "Matrix-Assisted Laser Desorption/Ionization Mass Spectrometry Sample Preparation Techniques Designed for Various Peptide and Protein Analytes", Journal of Mass Spectrometry, 32: 593-601, 1997.

Narayanan "Preparative Affinity Chromatography of Proteins", Journal of Chromatography A, 658: 237-258, 1994.

Nilsson et al. "Affinity Fusion Strategies for Detection, Purification, and Immobilization of Recombinat Proteins", Protein Expression and Purification, 11: 1-16, 1997.

Nisnevitch et al. "The Solid Phase in Affinity Chromatography: Strategies for Antibody Attachement", Journal of Biochemical and Biophysical Methods, 49: 467-480, 2001.

Noren et al. "Dissecting the Chemistry of Protein Splicing and Its Applications", Angewandte Chemie, International Edition, 39: 450-466, 2000.

Paulus "Protein Splicing and Related Forms of Protein Autoprocessing", Annual Review of Biochemistry, 69: 447-496, 2000.

Perler et al. "Protein Splicing and Its Applications", Current Opinion in Biotechnology, 11: 377-383, 2000.

Perler et al. "Protein Splicing Elements: Inteins and Exteins—A Definition of Terms and Recommended Nomenclature", Nucleic Acids Research, 22(7): 1125-1127, 1994.

Pietrokovski "Conserved Sequence Features of Inteins (Protein Introns) and Their Use in Identifying New Inteins and Related Proteins", Protein Science, 3: 2340-2350, 1994.

Pietrokovski "Modular Organization of Inteins and C-Terminal Autocatalytic Domains", Protein Science, 7: 64-71, 1998.

Porter et al. "Hedgehog Patterning Activity: Role of a Lipophilic Modification Mediated by the Carboxy-Terminal Auotprocessing Domain", Cell, 86: 21-34, 1996.

Porter et al. "Cholesterol Modification of Hedgehog Signaling Proteins in Animal Development", Science, 274(5285): 255-259, 1996.

Sano et al. "Streptavidin-Containing Chimeric Proteins: Design and Production", Methods in Enzymology, 326(19): 305-311, 2000.

Sano et al. "Genetic Engineering of Streptavidin, A Versatile Affinity Tag", Journal of Chromatography B, 715: 85-91, 1998.

Schmidt et al. "Molecular Interaction Between the Strap-Tag Affinity Peptide and Its Cognate Target, Strepatvidin", Journal of Molecular Biology, 255: 753-766, 1996.

Schmidt et al. "The Random Peptide Library-Assisted Engineering of A C-Terminal Affinity Peptide, Useful for the Detection and Purification of a Functional Ig Fv Fragment", Protein Engineering, 6(1): 109-122, 1993.

Sheibani "Prolkaryotic Gene Fusion Expression System and Their Use in Structural and Functional Studies of Proteins", Preparations in Biochemistry & Biotechnology, 29(1): 77-90, 1999.

Shingledecker et al. "Molecular Dissection of the Myobacterium Tuberculosis RecA Intein: Design of a Minimal Intein and of A Trans-Splicing System Involving Two Intein Fragments", Gene, 207: 187-195, 1998.

Skerra et al. "Applications of A Peptide Ligand for Strepatvidin: The Strep-Tag", Biomolecular Engineering, 16: 79-86, 1999.

Stoddard et al. "Breaking Up Is Hard to Do", Nature Structural Biology, 5(1): 3-5, 1998.

Vorm et al. "Improved Resolution and Very High Sensitivity in MALDI TOF of Matrix Surfaces Made by Fast Evaporation", Analytical Chemistry, 66(19): 3281-3287, 1994.

Wilchek et al. "An Overview of Affinity Chromatography", Methods in Molecular Biology, 147: 1-6, 2000.

Xu et al. "The Mechanism of Protein Splicing and Its Modulation by Mutation", The EMBO Journal, 15(19): 5146-5153, 1996.

* cited by examiner

Fig. 1a

```
A2115+_neime            9 SFHGSTLVKTADG   (0) YKAIAHIQAGDRVFAKDETSGK  (27) NNQTLISNKIHPFYS   (3) WIQAGRLKKGDTLLS   (0)
ESGAKQTVQNITLK        (4) KAYNLTVADWHTYFV  (7) EGVWVHNE (SEQ ID NO: 8)

B0372+_neimeB           6 SFHGSTLVKTADG   (0) YKAIARIRTGDRVFAKDEASGK  (27) NNQTLISNKIHPFYS   (3) WIQAGRLKKGDTLLS   (0)
ESGAKQTVQNITLK        (4) KAYNLTVADWHTYFV  (7) EGVWVHND (SEQ ID NO: 9)

B0655+_neimeB           9 SFHGSTLVKTADG   (0) YKAIARIRTGDRVFAKDEASGK  (27) NNQTLISNKIHPFYS   (3) WIQAGRLKKGDTLLS   (0)
ESGAKQTVQNITFK        (4) KAYNLTVADWHTYFV  (7) EGVWVHND (SEQ ID NO: 10)

3875_87_magma         292 CFVAGTPVRMADG   (1) EKAIETVEIGEQVQGTDGTINE  (17) NSLDFFVTADHPFLT  (17) ALNVTQLVIGDTLIT   (-)
--------------       (19) VVYNLHLIGNNTYVA  (0) SGYYVHNY (SEQ ID NO: 11)

FhaB_psesy           5987 CFAAGTMVSTPDG   (0) ERAIDTLKVGDIVWSKPEGGGK  (31) EDESLLVTPGHPFYV   (5) FVPVIDLKPGDRLQS   (-)
--------------       (23) KTYNLTVDGHTFYV   (2) LKTWVHNT (SEQ ID NO: 12)

FhaB1_psefl-PfO-1    1783 CFAAGTMVATPKG   (0) ERAIETLKIGDVVWSKPEQGGE  (31) SSETLEVTPGHPFYV   (5) FVPLIELQPGDRLQS   (-)
--------------       (23) RTYNLTVDIGHTFYV  (2) LGTWVHNV (SEQ ID NO: 13)

FhaB2_psefl-SBW25    3835 CFAAGTMVATPSG   (0) DRAIDTLKVGEIVWSKPEHGGE  (31) EGETLLVTPSHPFYV   (5) FVPAINLKPGDLLQS   (-)
--------------       (23) KTFNLTVDIGHTFYV  (2) LKTWVHNT (SEQ ID NO: 14)

SCP1.201_strco       1082 SFPAGTRVLMADG   (0) RRSIEQIEAGDLVTATDPTTGE  (24) DGSTLTSTTHHPYWS   (5) WKNAGDLEAGDTLRT   (0)
PQNTAVVIAATHDW        (4) DAYDLTVDGFHSYYV  (4) TDVLVHNN (SEQ ID NO: 15)

39_9_thefus           314 SFVPGTLVLLADG   (1) YAPIETITVGDDVWAFDPRTGT  (28) HGGVVVATDAHPFWV   (5) WVAAIDLEPGTWLRT   (0)
SAGTWVQVRAVAVR        (5) RVHNLTVADLHTYYV  (4) ADALVHNE (SEQ ID NO: 16)

MafB1_neigo           347 SFHGSTLVKTADG   (0) YKAIAHIQAGDRVLSKDEASGE  (27) NSQTLISNRIHPFYS   (3) WIKAEDLKAGSRLLS   (0)
ESGKTQTVRNIIVK        (4) KAYNLTVADWHTYFV  (7) EGVWVHND (SEQ ID NO: 17)

BIl2_neigo              9 PFHGSTLVKTADG   (0) YKAIARIRVGDHVFAKDEASGE  (27) NNQTLISNRIHPFYS   (3) WIKAEDLKAGSRLLS   (0)
ESGRTQTVRNIIVK        (4) KAYNLTVADWHTYFV  (7) EGVWVHNA (SEQ ID NO: 18)

BIl3_neigo              9 SFHGSTLVRTADG   (0) YKAIAHIQAGDRVLSKDEASGK  (27) NSQTLISNRIHPFYS   (3) WIKAEDLKAGNRLFA   (0)
ESGKTQTVRNIVVK        (4) KAYNLTVADWHTYFV  (7) EGVWVHNS (SEQ ID NO: 19)
```

```
MafB2_neigo      347 SFHGSTLVKTADG  (0) YKAIAHIQAGDRVLSKDEASGE (27) NSQTLISNRIHPFYS (3) WIKAEDLKAGSRLLS (0)
ESGKTQTVRNIVVK   (4) KAYNLTVADWHTYFV  (7) EGVWVHND (SEQ ID NO: 20)
BIL5_neigo         9 SFHGSTLVKTADG  (0) YKAIAHIQAGDRVLSKDEASGE (27) NSQTLISNRIHPFYS (3) WIKAEDLKAGSRLFA (0)
ESGKTQTVRNIIVK   (4) KAYNLTVADWHTYFV  (7) EGVWVHND (SEQ ID NO: 21)
BIL6_neigo         9 PFHGSTLVKTADG  (0) YKAIAHIQTGEHVFAKDETSGK (27) NSQTLISNRIHPFYS (3) WIKAEDLKAGSRLLS (0)
ESGRTQTVRNTVVK   (4) KAYNLTVADWHTYFV  (7) EGVWVHNS (SEQ ID NO: 22)
MafB1_neimeC     348 SFHGSTLVKTADG  (0) YKAIAHIRVGESVFAKDETSGK (27) NSQTLISNRIHPFYS (3) WIQAGRLKKGDTLLS (0)
ESGAKQTVQNITLK   (4) KAYNLTVADWHTYFV  (7) EGVWVHND (SEQ ID NO: 23)
BIL2_neimeC        9 PLVVGALVKTADG  (0) YKAIAHIRVGESVLSKDEASGK (27) NSQTLISNRIHPFYS (3) WIQAGRLKKGDTLLS (0)
ESGAKQTVQNITFK   (4) KAYNLTVADWHTYFV  (7) EGVWVHNA (SEQ ID NO: 24)
BIL4_neimeC        9 SFHGSTLVKTADG  (0) YKAIAHIRVGESVLSKDEASGK (27) NSQTLVSNKIHPFYS (3) WIKAEDLKAGSRLLS (0)
ESGKTQTVRNIVVK   (4) KAYNLTVADWHTYFV  (7) EGVWVHNA (SEQ ID NO: 25)
BIL5_neimeC        9 SFHGSTLVKTADG  (0) YKAIARIRTGDRVFAKDEASGK (27) NNQTLISNKIHPFYS (3) WIQAGRLKKGDTLLS (0)
ESGAKQTVQNITFK   (4) KAYNLTVADWHTYFV  (7) EGVWVHNA (SEQ ID NO: 26)
BIL6_neimeC        9 SFHGSTLVKTADG  (0) YKAIAHIQAGDRVLSKDEASGE (27) NSQTLVSNKIHPFYS (3) WIQAGRLKKGDTLLS (0)
ESGAKQTVQNITLK   (4) KAYNLTVADWHTYFV  (7) EGVWVHNS (SEQ ID NO: 27)
FhaB_manha      2881 SFHGDMEVKTDKG  (0) YRQISSIKVGDKVLAKNERTGI (27) KYHTIVSNKIHPFFT (24) WVDAQHLQKGYRLLA (0)
ESGEWQTVTKVKIK   (4) KAYNMTVEKDHTYFI  (7) EGVWVHND (SEQ ID NO: 28)
BIL1_cloth        48 CFVAGTLILTVAG  (0) LVAIENIKAGDKVIATNLETFE (22) NGEVIKTTFEHPFYV (4) FVEAKELQVGDKLLD (0)
SKGNVLVVEEKKLE   (6) KVYNFHVDDFYTYHV  (2) NGILVHNA (SEQ ID NO: 29)
BIL2_cloth        31 CFVAGTMVLTAAG  (0) LVAIENIKVGDKVIAANPETFE (22) GGEVIKTTVDHPFYV (4) FVEAVNLQVGDKLVD (0)
SKGNVLVVEEKKLK   (6) KVYNFKVDDFHTYHV  (2) KGILVHNA (SEQ ID NO: 30)
BIL4_cloth        16 CFVAGTMILTATG  (0) LVAIENIKAGDKVIATNPETFE (22) GGEVIKTTFDHPFYV (4) FVEAGKLQVGDKLLD (0)
SRGNVLVVEEKKLE   (6) KVYNFKVDDFHTYHV  (2) NEVLVHNA (SEQ ID NO: 31)
BIL5_cloth        31 CFVAGTMILTTTG  (0) LVAIENIKAGDKVIATNPETFE (22) GGEVIKTTFDHPFYV (4) FVEAKQLHVGDKLLD (0)
SKGNVLVVEDKKIK   (6) KVYNFQVADFHTYHV  (2) NGVLVHNV (SEQ ID NO: 32)
```

```
BIL6_cloth        87 CFVAGTMILTVAG  (0) LVAIENIKAGDKVIATNPETFE (22) NGDVIKTTFEHLFYA  (4) FVEAKELQVGDKLLD  (0)
SKGNVLVVEDKKIK  (6) KVYNFQVDDFHTYHV (2) NGVLVHNV (SEQ ID NO: 33)

BIL8_cloth         8 CFVAGTMILTATG  (0) LVAIENIKAGDKVIATNPETFE (22) GXEIIKTTLGHLFYV  (4) FVEAVKLQPTDKLVD  (0)
SGGNVLVVEXKKFE  (6) KVYNFKVNDFYTYHV (2) NGILVHNV (SEQ ID NO: 34)

BIL9_cloth        22 CFVAGTMILTATG  (0) LVAIENIKAGDKVIATNPETFE (22) GXEIIKTTLGHLFYV  (4) FVEAVKLQPTDKLVD  (0)
SGGNVLVVEXKKFE  (6) KVYNFKVNDFYTYHV (2) NGILVHNV (SEQ ID NO: 35)

0709_lepin      2026 CFTAGSKVTKLKN (29) FANIEEIKIGDIVRSWNENTNT (23) GEEEIHTTWNHPFRR (78) WVKVEDLRLKDQVLR  (0)
SDGSWGTVTGIYYY  (5) KVYNLEVEDNHTYVV (6) IGYVVHNY (SEQ ID NO: 36)

3725_lepin      2037 CFVAGSKVTKLKN (29) FANIEEIRIGDVVRSWNENTNT (23) GEEEIHTTWNHPFRR (74) WVKVEDLRLRDQVLR  (0)
SDGSWGTVTGIYYY  (5) KVYNLEVEDNHTYVV (6) KGYVVHNY (SEQ ID NO: 37)

BIL2_gemob      1296 CFAAGTKLLTRRG  (0) WVAVELLGIGDEVASRTEHDLT (24) GGELIRTTPEHPFWV  (4) WTAAGSLAAGDRIAT  (4)
LSGEWVPIAEVFDT  (4) PVYNLRVADHHTYFV (6) FAAWAHNA (SEQ ID NO: 38)

BIL1_gemob      6441 CFASGTPMRTPGG  (0) WCNIENLRVGDFVLSRDEFSPE (23) LGQTIRSTDEHPFFV  (-) ---------------  (-)
-------------- (37) TVYNFRVADHHTYFV (6) FSVWAHNI (SEQ ID NO: 39)

BIL1_pirsp       560 CLVAGTLVWTDRG  (0) MRPVESLRLGDQVLSCDVQTGS (22) GSDEIVASKGHPFWV  (4) WTTTEQLVPGDALHG  (-)
-------------- (16) KTYNLVVEQTHSYFV (2) SRILSHDA (SEQ ID NO: 40)

BIL1_strav      2125 SFKPTTRVLMKDG  (1) TKPLGKIKPGDLVEAADPTSGH (28) RIQTLHTTARHRIWD  (5) WEQAGRLITGHKVNT  (0)
SGNQHATITSVLAQ  (4) DMYDLTVEGLHTYYV (4) TPVLVHNG (SEQ ID NO: 41)

BIL2_strav      2105 CFLAGTDILMADG  (1) TKDIEEVELGDKVQATDPKTGE (27) GAEELTATHEHPFWS  (5) WITAGSLEPGMTLLT  (0)
DDGDTVIVTGNRAF  (4) TTYNLTVNDLHTYYA (4) TPVLVHNS (SEQ ID NO: 42)

BIL3_strav       389 SFPAGTRVLMGDG  (2) TLPIEQITVGDSVLATDPEAGT (29) GPPALTATDRHPFWV  (5) WADARDLNSGDTLRT  (0)
PDGTGVRIDKVTHW  (4) GAYNLTVNDLHTYYV (4) VPVLVHNA (SEQ ID NO: 43)

o1070_myxxa      937 CVAPWELVLLGDG  (1) EVPAEMLRPGMRVLTMHEHERD (22) DGRVLVVTPDHRWRT  (-) ---------------  (-)
-------------- (33) DVMRITVRFAMTYIV (0) QGLLAHNL (SEQ ID NO: 44)

```
o1078_myxxa            945 CVAPWEPVLLSDG  (1) EVPAEMLRPGMKVLTMHEHERD (22) DGRAVVTPDHRWRT  (-) --------------------- (-)
------------------    (35) DVMKISVRFAKTYVV (0) QGLLAHNL (SEQ ID NO: 45)

o649_versp             415 CFPSGTMVQTARG  (0) KVAIETLKEGDVVLAYDFLSEC (22) GDSKISATRFHLFWV (5) WVPAVDLQPGMVLRL      (0)
ESGALTVVTLAKLR         (6) ATHNFEVADLHNYFV (2) QGFLVHNG (SEQ ID NO: 46)

o5687_versp            548 CFPAGTMVLMADG  (1) SVPIEQVVEGDIVLAAEPETES (24) TGSVLKTGEHPIWT  (4) WQHADDLVEGDLLLK      (-)
------------------    (19) DTFNLCVEGVHTFYV (4) DAVLVHNT (SEQ ID NO: 47)

o3395_versp           3123 CFAPGTPVLMGDG  (1) TRPVETIREGDWIMADDPEDER (30) PDGALKATGGHPFWT (4) WIKVCNLQPNDILAD      (-)
------------------    (18) ATYNLSVANIHTFFV (4) VPVLVHNT (SEQ ID NO: 48)

BIL3_glovi            1741 CFAEGTEVQTETG  (0) TKAIEKVEPGEKVLARNEQTGE (29) ERDTLTVTGEHPFFL (4) WTAAERLRSGERVQA      (0)
VDGKWLRVVGLQPQ         (4) RTYNLEVEGEHTFFV (2) TRAWVHNE (SEQ ID NO: 49)

BIL2_glovi             115 CFAEGTEVQTETG  (0) AKPIELVAPGEKVLARNEQTGE (29) DRDVLTVTGEHPFFL (4) WTAADKLQVGERVQT      (0)
VDGQWLRVAGLQAQ         (4) RTYNLEVERDHTFYV (2) SKAWVHNE (SEQ ID NO: 50)

BIL1_glovi             184 CFSEGTEVQTEAG  (0) AKPIELVEPGEKVLARNEQTGE (29) ERDTLTVTGEHPFFL (4) WTAAERLKSGERVQA      (0)
ADGKWLRVAGLEAQ         (4) RTYNLEVEGDHTFFV (2) NQAWVHNE (SEQ ID NO: 51)

BIL1_chrvi             485 CFVAGTQVLTDKG  (0) LKAIETFVGGEWVWSRSDQTGE (27) RQETFRTTAEHPFWV (4) WLKASLLQAGVILVD      (0)
------------------    (18) TVFNIQVAEFQTYHV (2) LGVWVHNA (SEQ ID NO: 52)

BIL4_glovi              81 CFAEGTEVQTETG  (0) TKAIEKVEPGEKVLARNEKTGE (29) ERDTLTVTGEHPFFL (4) WTAADKLQAGDRVQA      (0)
VDGRWLRVVGLAAQ         (4) RTYNLEIEGEHTFFV (2) NQAWVHNE (SEQ ID NO: 53)

BIL5_glovi             104 CFGEGTAVQTETR  (0) AKPIEQIEPGEKVLARSERTGQ (43) ERDTSTVTGEHPFYL (-) ---------------      (-)
------------------    (-) --------------- (-) -------- (SEQ ID NO: 54)

BIL3_neimeC             11 -------------  (-) --------------------- (-) --------------- (3) WIKAEDLKAGSRLLS      (0)
ESGKTQTVRNIVVK         (4) KAYNLTVADWHTYFV (7) EGVWVHND (SEQ ID NO: 55)

BIL3_cloth              70 CFVAGTMILTATG  (0) LVAIENIKAGDKVIATNPETFE (22) NGEVIKTTFEHPFYV (4) FVEAGKLQIGDRLVD      (0)
------------------    (-) --------------- (-) -------- (SEQ ID NO: 56)

BIL7_cloth              17 -------------  (-) --------------------- (-) --------------- (-) ---------------      (-)
SKGNVLVVEEKKLE         (6) KVYNFKVNDFHTYHV (2) DGILVHNA (SEQ ID NO: 57)
```

| | | | | | | |
|---|---|---|---|---|---|---|
| BIL10_cloth | (-) | 0 VYNFKVDNFHTYHV | (-) | (2) NRVLVHNA | (-) | (SEQ ID NO: 58) (-) |
| BIL11_cloth KVYNF | (-) | 10 | (-) | (-) | (-) FVKEMKLQPGNRLVD | (SEQ ID NO: 59) (19) |
| 3719_lepin SDGSWGTVTGIYYY | (5) | 123 KVYNLEVEDNHTYIV | (-) | (6) IGYVVHNY | (-) WVKVEDLRLRDQVLR | (SEQ ID NO: 60) (0) |
| BIL6_glovi | (-) | 136 CFAEGTEVQT | (-) | (-) | (-) | (SEQ ID NO: 61) (-) |
| BIL7_glovi | (-) | 13 | (-) | (-) | (-) WTAAERLEPGDRVQA | (SEQ ID NO: 62) (-) |

Fig. 1b

```
00126_rhoca  160  CFTPGTLIDTPAG (0) PRPVEALRPGDRVSTRD (3) QEILWIGSRRM (12) PVRLGAVRLG (14) AADLLVSPQHRVLV (12)
EVLVQACDLVDDAAV   (8) VTYLHLLFARHQVIRAN (0) GVETESF (SEQ ID NO: 63)

00199_rhoca   37  GFYGETVLQTARG (0) LRRVSSILEGEKMRTFT (3) APVLSIERFAL (12) PLSLPAGLFG (1) TRNRFVAPEQCLLL (12)
LLLVPAKVLGLLPQV   (8) AVLYRLLFERPELVVTD (1) GAVMLCD (SEQ ID NO: 64)

00459_rhoca   38  GFAAGTRVRTPAG (0) LRRIETLKPGDLVETQE (3) QPVVAVERTRL (7) PIRFAAGAHG (1) ERPVLVAPQQRVLV (12)
EVLVAARTLVDGEMV   (7) VDYVRLVFDCAHMVFAE (0) GLAVECF (SEQ ID NO: 65)

00460_rhoca  174  CFAPSTPIATPGG (0) DCPAASLKAGDLVLTAD (3) QPILWSGRIAL (7) PVRLCAPAFG (1) TRDLWVLPQHRVAL (12)
EVLVPAHHLVDGISA   (8) LSWHGLLLQGHHLLIAD (0) GCRVESL (SEQ ID NO: 66)

00588_rhoca  473  CFTAGTLIETPRG (0) PVPVESLRAGDLVVTRD (3) VPVLWSGGRSL (12) PVAIRENALG (1) HGALLLSPQHAVLA (5)
ERLVRARHLAGLNDP  (10) VSYHHILLERHGIVTAN (0) GLACESL (SEQ ID NO: 67)

00746_rhoca   85  ALARGSVLMTEDG (0) PVAIEDLQPGQGVLTAE (3) ERVCWIGSMVI (15) LTRITAEAFG (4) ALDLVLGPRARLCL (12)
AADVPARAFLDGISV   (8) VTYVHVLEQHGSLRVA (0) GLEVEAF (SEQ ID NO: 68)

00949_rhoca  125  CLGTGTMIATAEG (0) PAPIDWLRPGDRVLTRD (3) QPLLWVGQHTM (9) PLLLSAACFG (4) ERDVLLSPGTGVLL (12)
EMFAKARHALPKAEA   (4) QKLYSMLLATPEVVLAE (0) GMWVGSV (SEQ ID NO: 69)

01216_rhoca  128  CFAAGTLIATRRG (0) PKPVEDLGPEDRLQTSD (3) RPVQWVGRWRV (7) PVRFAPGVLG (1) DRALFLSGQHRVLI (10)
EVLVAAKALVGLPGI   (7) VDWVHVMPTHEVIFAE (0) NARAETM (SEQ ID NO: 70)

01374_rhoca  144  AFTTGTLITMAGG (1) QRPIETLAPGDRVLTRD (3) QPVRLVARATL (7) PVVISAGTLG (1) ESDLVVAPHHRVFL (12)
EILVQAKHLVDGEHV   (7) VDYFALVFDRHEIVYAE (0) GVPVESL (SEQ ID NO: 71)

01523_rhoca   85  CFTATSLIATGQG (0) GVPVSELVPGARVITRD (3) QELLWVGRRRF (12) PVRIAAGALG (4) ERDMLVSPNHRFLT (9)
ERLTMARDLVGLDGI   (7) VDYWQLLFAHHELVLAD (0) GAWSESF (SEQ ID NO: 72)

01524_rhoca   89  CLTPGTLIETKRG (0) QVPVEKLRPGDRVLTRD (3) QPIRWIGRRRL (12) PVRIAAGALG (4) ETDMLVSPQHRMLI (12)
EVLAAALHMLGQPGI   (7) VTYLHLMLDAHEIIRAN (0) GAWTESF (SEQ ID NO: 73)

02710_rhoca  541  CLVAGSRVSTPRG (0) PVPVEDLRPEDLVTVRD (3) LPVLWIGRRRV (12) PVEIGAGRLG (1) AAPVRLSALHGIAV (2)
GFLARAGHLAATGWG  (14) VLYLHLLLPRHALLSVE (0) GLWVESF (SEQ ID NO: 74)
```

```
03530_rhoca    39 GFAMGSRVATMDG  (0) LLPVEFLNGDRIVTRS  (-) ----------      (16) LVGIAPGALG  (4) GQAMVLGSTQVLL  (12)
QALVAVERLIDGQFI   (7) IRIFALHFEAPEVIYAD (0) GVEIGCK           (SEQ ID NO: 75)
4825_rhosp     28 CFTPGTLIATVRG  (0) EVAVEALAAGDRIVTRD (3) QPLRWISRRRL   (12) PVLIEKGSLG  (4) DRDMVSPNHRILV  (12)
EVLVAAKHLVGPRGI   (7) TTYLHLMFDRHEVVLAN (0) GAWTESF           (SEQ ID NO: 76)
BIL2_rhosp     34 SLTAGTPVLTLAG  (0) IRPAEGIRPGDRLVARS (-) ----------      (17) MVAIGASTLA  (4) DETLLVPADQPLLL (12)
PVVLPARRLVDGQLT   (7) VDLVTLTFAAPAAIYAS (0) ELHPVTR           (SEQ ID NO: 77)
BIL1_brusu     86 CLLKGTLVTTPNG  (0) PVAVEKLCVGDLVTTVS (3) LPIKWIGWQNY   (12) PIRVRRHALD  (4) HRDLYLSPNHALFI (1)
GVLIRVKDLVNGRSI   (8) LDYNIVLDRHAVVLAE  (0) GAAVETF           (SEQ ID NO: 78)
II0519_brume   15 CLLKGTLVTTPNG  (0) PVAVEKLCVGDLVTTVS (3) LPIKWIGWQNY   (12) PIRVRRHALD  (4) HRDLYLSPNHALFI (1)
GVLIRVKDLVNGRSI   (8) LDYNIVLDRHAVVLAE  (0) GAAVETF           (SEQ ID NO: 79)
BIL1_unknwn   217 CFLPGTMIKTPSG  (0) ERPVEDIQINDEVITFD (8) SKIKWVGSKTI   (13) PVRILKNAIS  (4) HKDLLVTPEHCLFF (1)
GKFIPVRMLVNHQTI   (8) YTYYHIETENHSVIYSD (0) GMLTESY           (SEQ ID NO: 80)
BIL2_unknwn   184 CFLSGTQIKTKLG  (0) VKNIEALQVGDFVTTYD (8) REVTWVGXKYC   (13) PVRIVKDAIA  (4) YKDLLVTAEHCLFF (1)
DKFIPARMLVNGSTI   (8) YEYYHLETQDHAVIIAD (0) GVRTESY           (SEQ ID NO: 81)
BIL1_metex    139 CFTTGTLIRTARG  (0) SVAVEDLIVGDLAVTAS (3) RPITWIGNRAL   (12) PIRIRAGAFG  (4) ARDLRLSHGHPVLV (8)
GVLIVPVMCLINGTSV  (7) VTYWHIELDAHDILLAE (0) GLAAESY           (SEQ ID NO: 82)
BIL2_silpo    162 CFTPGTKIATPKG  (0) ERLVEDLEVGDRVITRD (3) QEIRWVGSRTL   (12) PVLIRQGALG  (4) ERDMIVSPNHRILV (12)
EVLVAAKHLIGLEGV   (7) VTYIHFMFDQHEVVLSD (0) GAWTESF           (SEQ ID NO: 83)
BIL2_silpo    697 CFCRGTLIATAGG  (0) EIPVEKLRPGDRVITRD (3) QRIRWIGGTSR   (7)  PIRIRTGVLK  (1) TRDLLVSPNHRILM (12)
EVLVAAKFLVDGRAI   (7) VDYYHMLFDQHELVLSE (0) QAWSESF           (SEQ ID NO: 84)
BIL3_silpo    512 CFAAGTRIETDRG  (0) GRAIEDIAVGDLVLTRD (3) QPVRWTGRRSV   (7)  PIRIASGKLG  (1) LRDLLVSPQHRLLL (12)
EVLAAAVHLRDDRHI   (7) VTYVHLMFDRHEIIYAE (0) GVSAESF           (SEQ ID NO: 85)
BIL4_silpo    159 CFTPGTRIATPTG  (0) PRLIEELREGDKVQTRD (3) QEIQWIGQRRM   (12) PIRMRVGALG  (4) DAELLVSPEHRMLL (12)
EVLVPARDLVNDSTI   (8) VTYVHLLLPSHQILWAN (0) GIETESF           (SEQ ID NO: 86)
```

```
BIL5_silpo   153  CFAAGTFIEIESG (0) PIPVETLRPGDLVQTLD (3) QPLLQLAKTTV (7) PVLFRAGVLG (1) FRDLYVSQQHRMLI (12)
EVFVPARMLVNGSTI   (7) LTYYHLLFARHEIVFSE (0) GIPTESY (SEQ ID NO: 87)

BIL6_silpo   350  CFVAGTLIDTPYG (0) ERQVERLTPGDQVFTRD (3) QEVRWVGERTV (7) PILIRAGTYG (1) QRDLMVSPQHRILI (12)
EVLVAAKDLVDGRRV   (7) ITYVHVMFDSHQVIYSE (0) GLASESF (SEQ ID NO: 88)

BIL7_silpo   248  SLHPETPIATPDG (0) YRPLSKIRRGDTVIVAS (3) VPVLHRVSRTM (7) PLTIRRPYFG (1) RQDIQAAPSQRLLL (12)
SVLVPARHLTGGHSV   (8) ATYAQLLLPTNEAMITA (0) GALAESL (SEQ ID NO: 89)

BIL8_silpo   179  CFVAGSLIDTVEG (0) PRPVETLAVGDLVPVED (3) QPILWIGKRTL (12) PVRIRRDALG (4) HRTLWVSPQHRIVL (12)
QVFAAAIHLTNDDTI   (8) VTYYHLAFERHLLLRAH (0) GLLSESI (SEQ ID NO: 90)

BIL9_silpo   511  CFTPGTLIATAHG (0) PRAIETLRPGDLIVTRD (3) QPLRWVGSRTV (7) PIRLDPTLLQ (2) SAPLLVSPQHRMLW (12)
EVLVAATHLLGSPAA   (7) VTYMHLMLDRHEVIYAN (0) DAATESF (SEQ ID NO: 91)

BIL10_silpo  174  CFTPGTIIDTEDG (0) PRLIEELQPGDLIRTLD (3) QPLRWIGRTTV (7) PVLIRAGALD (1) RRDLIVSPQHRMLI (12)
QALVAAKHLVNARDI   (7) VTYIHLLFDRHEIWAE (0) GCPTESF (SEQ ID NO: 92)

BIL11_silpo  162  CFAAGTRIATPKG (0) ARPVETLAVGDLVQTLD (3) QPIRWIGTRRV (12) PVVIPAHSFA (4) THPLLLSQQHRVLL (12)
EILIAARRLTGLHGI   (8) VRYIHFALDRHEIVFAN (0) GLPAETL (SEQ ID NO: 93)

BIL12_silpo  158  SFTRGTHITLGSG (1) QVRIEDLKVGDRVLTRD (3) REVRWIGQTTV (7) PIVIRAGTLN (1) ENDLVVSPDHRLFV (12)
ELLLKARHLVNGDTV   (7) VDYFQLLFDRHHIIYAE (0) GIAAETM (SEQ ID NO: 94)

BIL13_silpo  75   AFSRGSLIDTDCG (0) PMAIEDLLPGDRVITQD (3) QEVVWKGSTVI (13) LTRIMADAFG (4) MSGVIAGPSARLLA (12)
PMLTPVQHFVDGMGI   (8) IEVFHICLRRHAVINVD (0) GLQFETY (SEQ ID NO: 95)

BIL14_silpo  30   GLPAGTMLETEAG (0) WSPVEEIRPGTRVATID (1) --------- (18) LWRIPGGTLG (1) CSDLLLPEGHFLAL (12)
TVLAPVAALAGFEGI   (7) LPAHSLRFAEEEVVWAQ (-) ------- (SEQ ID NO: 96)

BIL15_silpo  35   GFLAGTILLTQDG (0) EMPVEFLSPGDRIITRD (3) VPLHHITRAPQ (3) AIRIAAGSLG (4) DCDLILPAGQPVLI (12)
QAMVRADALVDGEFI   (7) MQLFQLHFDSAHVLYAG (-) ------- (SEQ ID NO: 97)

BIL16_silpo  53   GLLAGTSVASNFG (0) WQPVEALKVGDKVLTFD (3) QTVADIQRETV (11) PVRLPEGVCH (1) RRDLWMMPDQGLLV (12)
YAVVPARMLRGYRGI   (8) VEVTTLAFHQDEVIYVE (-) ------- (SEQ ID NO: 98)

BIL1_rhile   122  CFLRGTAILTDCG (0) EKPVENLSIGDRVALPD (3) RPIKWVGRQSF (12) PIRVSRHALD (4) HSDLYLSPGHALYL (1)
GILIQVKDLVNGKTI   (10) IEYYAVMLDTHEVILAG (0) GAETESF (SEQ ID NO: 99)
```

```
BIL3_magma    45 CYVTGTRIRTERG (0) EIAVEDLQVGDFAVTAS (3) RPITWIGHREI (12) PVRVRAGAFG (4) VNDLFLSPGHPVLV (8)
GVLVPVMCLINGTTI  (7) VTYWHVELDAHDILLAE (0) GLPAESY (SEQ ID NO: 100)

BIL4_magma   129 CFVSGTRISVERG (0) SIPVELLRIGEKARLAS (3) RTITWIGHREI (12) PVRVRAGAFG (4) ARDLFLSPGHPVLI (8)
GVLVPVMCLINGTSI  (7) VTYWHVELDRHDILLAE (0) GLPAESY (SEQ ID NO: 101)

BIL2_magma   126 CFVTGTMIATARG (0) EVAVEDLRAGDFARTAE (3) RPIVWIGHREI (12) PVRVRTGAFG (4) ARDLYLSPGHPVLV (8)
GTLVPI-------    (-) ----------------- (-) ----------- (-)  ---------- (-) -------------- (-)
                                                                                                (SEQ ID NO: 102)

BIL5_magma    18 (-) ------------- (-) ----------------- (-) ----------- (-) ---------- (-) -------------- (-)
---------------  (-) VTYWHVELDAHDILLAE (0) GLPAESY (SEQ ID NO: 103)

BIL6_magma    10 (-) ------------- (-) ----------------- (-) ----------- (-) ---------- (-) -------------- (-)
RLPAESY-------                                                                          (SEQ ID NO: 104)
```

Fig. 2a

SEQ ID NO: 105

[CSP] [FLV] XX [GSWDT] [TESAM] X [VILM] X [TMLK] XX [GN] X(0-100) [IVAL] [EADGS] X [ILVF] XX [G] [DEM] X [VI] X [ASTG] X(0-100) [LIFV] X [STVAVL] [TNS] XXH [PLR] [FIWYV] X (0-200) [AVTM] [YFHM] [NDRK] [LFIM] X [VIL] XXXX [TSNE] [YFL] X [VAI] X (0-100) [WLVY] [VAS] [H] [ND] X

Fig. 2b

SEQ ID NO: 106

[CGAS] [FLY] XX [GEST] [TS] X [IVL] XXXXGX (0-100) [VIAL] [ESAD] X [LI] XX [GEN] [DEAQT] X [VIALM] X [TVLA] X [DSET] X (0-100) [PLAM] [VILTW] X [ILVFM] XXXXX [ADGHKNQS] X (0-100) [ACDEFGHLMQRSTVY] [ACEGHKLNQRST] [ADEGNPT] [ILMRV] [FILMQRVWY] [ALMV] [AGLMPST] [AEGHPQS] [DEGHLNQRS] [AHQT] [ACFGPQR] [FILMV] [ACFLVY] [AFILMTVW] X (0-100) [ADEGLPQSTY] [AFIKLMRTV] [DFLMV] [AILTV] [AKMPQR] [AIV] [ACDEGHIKLMQRTV] [ACDFHMRTV] [AFLM] [AGILRTV] [ADGLNP] [ADFGHKLNPQSTY] [ADEGHIMNPQRSTK] [ADEFGHLMQRSTW] [AGIPTV] X (0-100) [AILMQTVY] [DEKLPQRSTV] [AILVWY] [AFHILMTVWY] [AGHNQRST] [FILMV] [ACEHLMRTV] [FLMT] [ADEHPQR] [ACDEGHNQRST] [ADEHNP] [ADEGHLQS] [AILMSV] [ILMV] [FILNRSTVWY] [AGSTV] [ADEGHNQS]

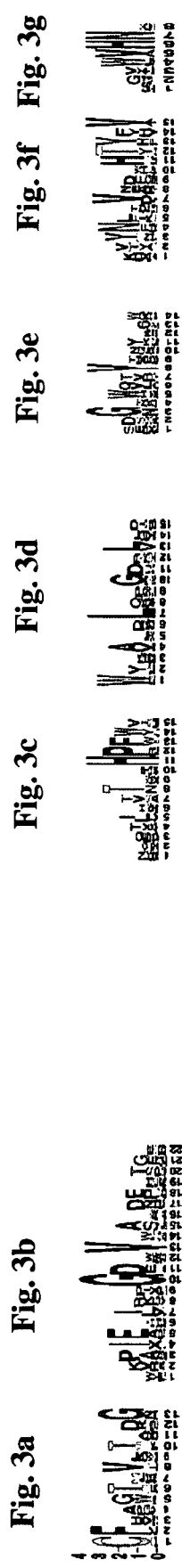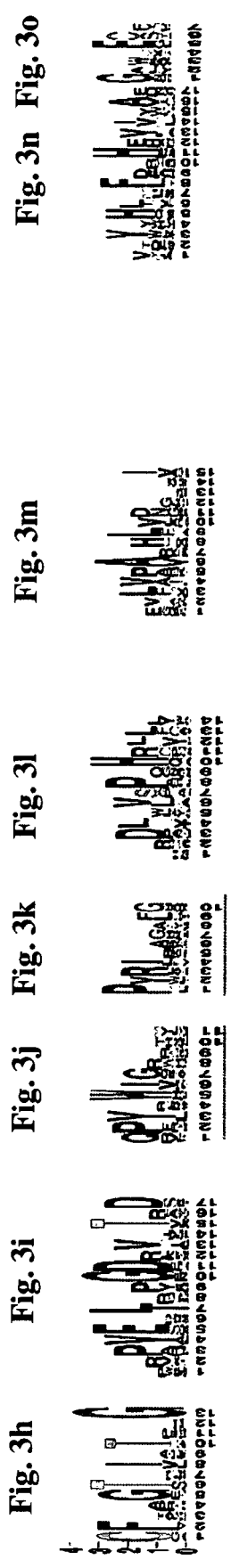

Fig. 5c

SEQ ID NO: 107

| | | | | | |
|---|---|---|---|---|---|
| CFAAGTMVST | PDGERAIDTL | KVGDIVWSKP | EGGGKPFAAA | ILATHIRTDQ | PIYRLKLKGK | 6046
| QENGQAEDES | LLVTPGHPFY | VPAQHGFVPV | IDLKPGDRLQ | SLADGASENT | SSEVESLELY | 6106
| LPVGKTYNLT | VDVGHTFYVG | KLKTWVHNT | | | | 6135

Fig. 7

SEQ ID NO: 108

```
MKTEEGKLVI  WINGDKGYNG  LAEVGKKFEK  DTGIKVTVEH  PDKLEEKFPQ  VAATGDGPDI   60
IFWAHDRFGG  YAQSGLLAEI  TPDKAFQDKL  YPFTWDAVRY  NGKLIAYPIA  VEALSLIYNK  120
DLLPNPPKTW  EEIPALDKEL  KAKGKSALMF  NLQEPYFTWP  LIAADGGYAF  KYENGKYDIK  180
DVGVDNAGAK  FLVDLIAGLT  KNKHMNADTD  YSIAEAAFNK  GETAMTINGP  WAWSNIDTSK  240
VNYGVTVLPT  FKGQPSKPFV  GVLSAGINAA  SPNKELAKEF  LENYLLTDEG  LEAVNKDKPL  300
GAVALKSYEE  ELAKDPRIAA  TMENAQKGEI  MPNIPQMSAF  WYAVRTAVIN  AASGRQTVDE  360
ALKDAQTNSS  SNNNNNNNNN  NLGIEGRISE  FGSTSRVDCG  GLTGLNSGLT  TNPGVSAWQV  420
NTAYTAGQLV  TYNGKTYKCL  QPHTSLAGWE  PSNVPALWQL  Q                      461
```

Fig. 8

SEQ ID NO: 109

```
MKTEEGKLVI WINGDKGYNG LAEVGKKFEK DTGIKVTVEH PDKLEEKFPQ VAATGDGPDI    60
IFWAHDRFGG YAQSGLLAEI TPDKAFQDKL YPFTWDAVRY NGKLIAYPIA VEALSLIYNK   120
DLLPNPPKTW EEIPALDKEL KAKGKSALMF NLQEPYFTWP LIAADGGYAF KYENGKYDIK   180
DVGVDNAGAK AGLTFLVDLI KNKHMNADTD YSIAEAAFNK GETAMTINGP WAWSNIDTSK   240
VNYGVTVLPT FKGQPSKPFV GVLSAGINAA SPNKELAKEF LENYLLTDEG LEAVNKDKPL   300
GAVALKSYEE ELAKDPRIAA TMENAQKGEI MPNIPQMSAF WYAVRTAVIN AASGRQTVDE   360
ALKDAQTNSS SNNNNNNNNN NLGIEGRISE FGScfaagtm vstpdgerai dtlkvgdivw   420
skpegggkpf aaailathir tdqpiyrlkl kgkqengqae desllvtpgh pfyvpaqhgf   480
vpvidlkpgd rlqsladgas entsseevesl elylpvgkty nltvdvghtf yvgklktwvh   540
n                                                                   541
```

Fig. 12a
Fig. 12b
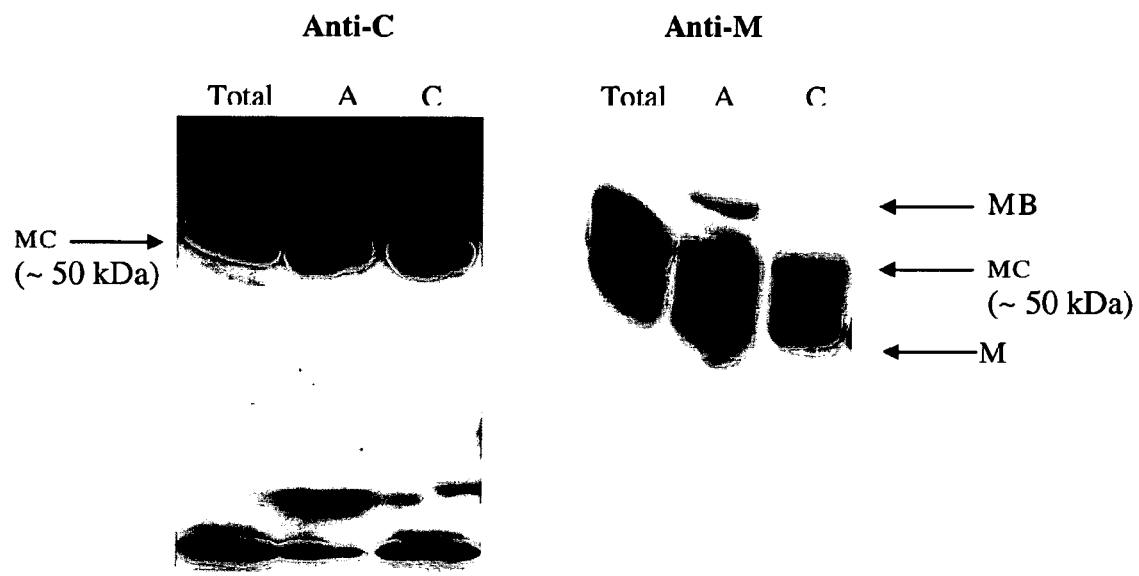
Fig. 12c
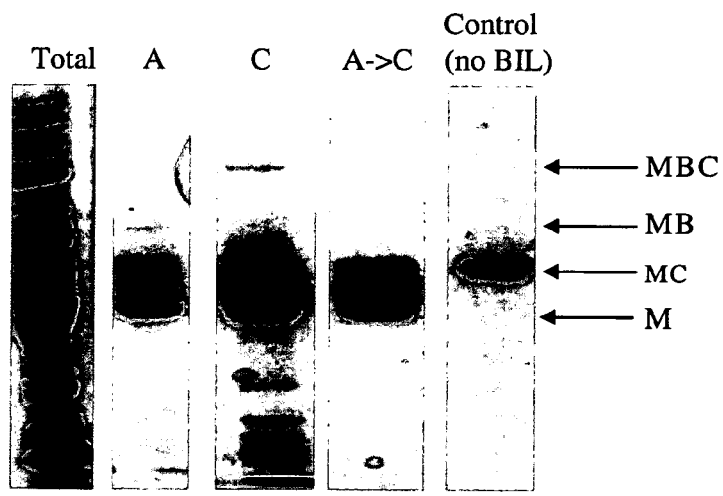

CHIMERIC AUTOPROCESSING POLYPEPTIDES AND USES THEREOF

RELATED PATENT APPLICATION

This application is a National Phase Application of PCT/IL03/00956 having International Filing Date of 12 Nov. 2003, which benefits of U.S. Provisional Patent Application No. 60/425,295 filed 12 Nov. 2002.

FIELD AND BACKGROUND OF THE INVENTION

The present invention relates to polypeptides having the capacity to display auto-cleavage, polynucleotides encoding such polypeptides, and uses of such polypeptides and polynucleotides for reversibly binding proteins to specific substrates, reversibly binding specific substrates to each other, and for splicing amino acid sequences. More particularly, the present invention relates to chimeric polypeptides capable of auto-cleaving at defined locations, including auto-cleaving resulting in defined auto-splicing, to polynucleotides suitable for expressing such polypeptides, and to methods of using such polypeptides and polynucleotides for protein purification, affinity selection of display phages, and post-translational ligation of proteins.

Autoprocessing protein domains, such as inteins and Hogs, have the capacity to post-translationally auto-cleave or auto-splice flanking polypeptide sequences and thereby serve as unique and potent protein engineering tools useful in various applications, including protein purification, affinity selection of display phages, generation of cytotoxic proteins, segmental modification or labeling of proteins, protein or peptide cyclization, and generation of reactive polypeptide termini in expressed proteins for various biochemical reactions, including protein ligation (Perler and Adam, 2000. Curr Opin Biotechnol. 11, 377-83). However, the usefulness of the presently available repertoire of autoprocessing polypeptides is hampered by various limitations, as described in further detail hereinbelow.

Inteins are internal protein domains naturally occurring in a variety of host proteins (Hirata et al., 1990. J. Biol. Chem. 265, 6726-6733; Kane et al., 1990. Science 250, 651-657; Perler et al., 1994. Nucl. Acids Res. 22, 1125-1127; Noren et al., 2000. Angew. Chem. Int. Ed. 39, 450). Inteins have been found in organisms from all three domains of life, including in yeast and algal chloroplasts (eukaryotes), mycobacteria and cyanobacteria (bacteria), and thermophilic archaea (archaea). So far, no essential biological role has been shown for inteins, and all of their identified functions involve their own preservation and maintenance, with no apparent benefit to the host protein and organism (reviewed in Pietrokovski, 2000. Trends in Genetics 17, 465-472). At least some inteins are multifunctional, being able to both catalyze their own protein splicing and to home a copy of their gene into intein-less alleles (Gimble and Thorner, 1992. Nature 357, 301; Chong et al., 1996. J Biol. Chem. 271, 22159). Hogs are protein domains found in Hedgehogs which are proteins composed of an amino terminal Hedge protein domain and a carboxy terminal Hog protein region (Aspock G., 1999. Genome Res. 9, 909; Hammerschmidt et al., 1997. Trends Genet. 13, 14). Other protein domains, such as various *Caenorhabditis elegans* carboxy terminal domains, are believed to autocatalytically cleave themselves from host proteins, thereby modulating the activity of the amino terminal parts (Burglin, 1996. Curr Biol. 6, 1047; Porter et al., 1996. Cell 86, 21), similarly to Hogs.

Members of the intein and Hog protein domain families share the capacity to autocatalytically cleave the peptide bond joining them to polypeptides flanking their amino terminal ends ("amino terminal cleavage"). Inteins have the further capacity to cleave the peptide bond joining them to polypeptides flanking their carboxy terminal ends ("carboxy terminal cleavage") while splicing polypeptides flanking their amino and carboxy terminal ends (termed "exteins"), resulting in self-excision of the intein from the host protein, and concomitant ligation of the flanking extein domains with a peptide bond. Thus, intein-containing host proteins undergo a switch from an intein-containing state to an intein-less state via such a process. Most reported inteins furthermore also contain an endonuclease domain whose function is to mediate the copying of the intein gene into specific unoccupied genomic insertion points, thereby enabling intein propagation.

Both inteins and Hogs share a similar structure fold and contain characteristic "Hint" consensus motifs which mediate the biochemical reactions involved in the autocatalytic activities of these protein domains (Hall T M., 1997. Cell 91, 85; Pietrokovski S., 1994. Protein Sci. 3, 2340; Pietrokovski S., 1998. Protein Sci. 7, 64; Paulus, 2000. Annu. Rev. Biochem. 69, 447). These Hint motif-mediated biochemical reactions are similar in both inteins and Hogs, but are involved in different biological processes (Dalgaard et al., 1997. J Comput Biol. 4, 193; Hall et al., 1997. Cell 91, 85; Pietrokovski S., 1998. Protein Sci. 7, 64; Xu and Perler, 1996. EMBO J. 15, 5146). The initial biochemical reactions of intein and Hog amino terminal cleavage are identical; the peptide bond attaching the amino terminal end of the Hint domain to an amino terminal-flanking sequence is converted into a thioester (or ester) bond, a trans-esterification reaction then covalently attaches the sequence flanking the carboxy terminal end of the intein, or a cholesterol molecule in the case of Hog proteins, to the amino terminal flanking sequence, thereby cleaving the bond attaching the amino terminal sequence to the Hint domain. In a process essential for organismal development, Hint-mediated autocatalytic excision of the carboxy terminal Hog protein domain from the amino terminal Hedge protein domain in Hedgehogs leads to covalent attachment of a cholesterol molecule to the carboxy end of the Hedge domain, leading to its activation and secretion from the cell (Porter J A. et al., 1996. Cell 86, 21; Porter, J A. et al., 1996. Science 274, 255). In the case of inteins, protein splicing is effected sequentially by cleavage of the bond attaching the intein amino terminal end to the carboxy terminal extein, ligation of the amino and carboxy terminal exteins, and cleavage of the bond attaching the intein carboxy terminal end to the carboxy terminal extein.

Mechanistic studies have determined the roles of highly conserved residues positioned near the intein/extein junctions in the splicing reaction (Chong et al., 1996. J. Biol. Chem. 271, 22159-22168; Xu et al., 1996. EMBO J. 15, 5146-5153; Stoddard et al., 1998. Nat. Struct. Biol. 5, 3). These residues include: the Cys, Ser or Thr residue forming the amino terminal end of the intein, which initiates splicing with an acyl shift; the conserved Cys, Ser or Thr residue flanking the carboxy terminal end of the intein, which ligates the exteins through nucleophilic attack; and the conserved Asn forming the carboxy terminal end of the intein, which releases the intein from the ligated exteins via succinimide formation. The amino terminal acyl shift and the carboxy terminal succinimide formation cleavage activities of the intein are separable. The amino terminal cleavage takes place in two separate steps. In the first step, as described above, the peptide bond between the intein and the amino terminal extein is converted to a thioester (or ester in some cases). In the second step, the thioester bond is cleaved by a nucleophilic attack from the side-chain of the residue flanking the carboxy terminal end of the intein, causing a transesterification reaction.

Because the structural information required for splicing exists entirely within inteins, and since the process of splicing has no energy requirements (for example hydrolysis of ATP), such protein domains can be used in a variety of applications involving intein insertion into foreign contexts. Various methods have been used in attempts to control and alter intein-mediated functions. Since endonuclease activity is not required for protein splicing, mini-inteins with accurate splicing activity have been generated by deletion of this central domain (Derbyshire et al., 1997. Proc. Natl. Acad. Sci. USA. 94, 11466; Chong et al., 1997. J. Biol. Chem. 272, 15587; and Shingledecker et al., 1998. Gene 207, 187). Also, mutation of residues near the intein/extein junctions has been used to alter intein activity, for example, to yield isolated cleavage at one or both of the intein-extein junctions (Chong et al., 1998. J. Biol. Chem. 273, 10567).

Thus, the ability to modulate the function of autoprocessing polypeptides such as inteins has broad potential application, as described above. In the case of protein purification where an autoprocessing polypeptide is used in conjunction with an affinity group to purify a desired target protein (Chong et al., 1997. Gene 192, 271-281; Chong et al., 1998. Nucl. Acids Res. 26, 5109), purification of a target protein is effected by co-expressing the target protein as a fusion protein containing a purification tag in one terminal segment, an internal autoprocessing polypeptide, and a target protein forming the other terminal segment. Such fusion proteins are exposed to affinity purification matrices designed to capture the tagged molecule. The target protein is then selectively released from the purification matrix by inducing autoprocessing polypeptide-mediated auto-cleavage of the peptide bond attaching the target protein to the autoprocessing polypeptide. Such a procedure is advantageous since autoprocessing polypeptide cleavage affects the fusion protein only, and thus non-specifically bound contaminant proteins are not released into the product stream. Furthermore, such a method does not employ contaminating and expensive proteases, such as those used in technologies employing protease-mediated cleavage of purification-tagged target proteins. The aforementioned strategy forms the basis of the protein purification systems such as the commercially available IMPACT-CN system (New England Biolabs, Beverly, Mass.).

However, prior art methods of using such autoprocessing polypeptides for applied uses have numerous drawbacks. In applied systems such as IMPACT-CN, the accessory molecule involved in cleavage of the thioester bond between the intein and the extein following amino terminal cleavage must be effected with a strong thiol-containing nucleophile such as 2-mercaptoethanol or dithiothreitol (DTT), both of which are strong reducing agents which modify the carboxy terminal end of the extein. In such systems, although initial thioester formation is mediated by the intein, the actual cleavage of the extein is effected via non-enzymatic chemical cleavage of a thioester bond by a small nucleophilic molecule, thereby severely limiting the maximal reaction rates achievable. While such systems allow carboxy terminal cleavage, such cleavage has the drawback of resulting in undesirable amino terminal cleavage, thereby requiring the amino terminal fragment to be removed in an additional purification step. Furthermore, despite insights into intein structure and function, modifications often result in unacceptably low activity, poor precursor stability, or insolubility (Derbyshire et al., 1997. Proc. Natl. Acad. Sci. USA. 94, 11466; Chong et al., 1997. Gene 192, 271-281; Shingledecker et al., 1998. Gene 207, 187; Chong et al., 1998. Nucl. Acids Res. 26, 5109).

Thus, all prior art approaches have failed to provide an adequate solution for providing autoprocessing polypeptides optimal for protein engineering applications.

There is thus a widely recognized need for, and it would be highly advantageous to have, autoprocessing polypeptides devoid of the above limitation.

SUMMARY OF THE INVENTION

According to one aspect of the present invention there is provided an chimeric polypeptide comprising an autoprocessing segment having an amino acid sequence set forth by SEQ ID NO: 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105 or 106, the polypeptide being capable of auto-cleavage.

According to another aspect of the present invention there is provided a polynucleotide encoding a chimeric polypeptide comprising an autoprocessing segment having an amino acid sequence set forth by SEQ ID NO: 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105 or 106, the polypeptide being capable of auto-cleavage.

According to further features in preferred embodiments of the invention described below, the chimeric polypeptide further comprises an affinity tag capable of specifically binding a substrate.

According to still further features in preferred embodiments, the substrate is selected from the group consisting of a molecule, a compound, a virus, and a cell.

According to yet another aspect of the present invention there is provided a nucleic acid construct comprising a nucleic acid sequence encoding a chimeric polypeptide comprising an autoprocessing segment having an amino acid sequence set forth by SEQ ID NO: 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105 or 106, the chimeric polypeptide being capable of auto-cleavage.

According to further features in preferred embodiments of the invention described below, the nucleic acid construct further comprises a promoter sequence being for directing expression of the chimeric polypeptide in an expression system.

According to still further features in preferred embodiments, the chimeric polypeptide further comprises an affinity tag capable of specifically binding a specific substrate.

According to still another aspect of the present invention there is provided a method of generating a chimeric polypeptide capable of displaying auto-cleavage, the method comprising generating a chimeric amino acid sequence including an autoprocessing segment, the autoprocessing segment having an amino acid sequence set forth by SEQ ID NO: 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105 or 106, thereby producing the chimeric polypeptide capable of displaying auto-cleavage.

According to further features in preferred embodiments of the invention described below, the chimeric polypeptide includes an affinity tag.

According to a further aspect of the present invention there is provided a method of purifying a protein, the method comprising: (a) generating a chimeric polypeptide including an autoprocessing segment having an amino acid sequence set forth by SEQ ID NO: 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105 or 106, the autoprocessing segment being terminally attached to, or flanked by, an amino acid sequence of the protein, the chimeric polypeptide being capable of auto-cleavage when subjected to suitable conditions to thereby remove the amino acid sequence of the protein from the chimeric polypeptide thereby generating the protein; (b) immobilizing the chimeric polypeptide to a support; and (c) subjecting the chimeric polypeptide to the suitable conditions, thereby purifying the protein.

According to further features in preferred embodiments of the invention described below, the method of purifying a protein further comprises the step of separating the protein from the autoprocessing segment following step (c).

According to still further features in preferred embodiments, the support includes an antibody or antibody fragment capable of specifically binding the autoprocessing segment, and the immobilizing is via the autoprocessing segment.

According to still further features in preferred embodiments, the chimeric polypeptide further includes an affinity tag sequence, and the immobilizing is via the affinity tag sequence.

According to still further features in preferred embodiments, the support includes a specific ligand of the affinity tag sequence, and the immobilizing is via the specific ligand of the affinity tag sequence.

According to still further features in preferred embodiments, the generating the chimeric polypeptide is effected by synthesizing a polynucleotide encoding the chimeric polypeptide and expressing the polynucleotide in an expression system.

According to still further features in preferred embodiments, the expression system is a cellular expression system or a cell-free expression system.

According to still further features in preferred embodiments, the cellular expression system is an *E. coli* cellular expression system.

According to still further features in preferred embodiments, the cell-free expression system is an *E. coli* S30 extract expression system.

According to still further features in preferred embodiments, the polynucleotide comprises a promoter sequence being for directing the expression of the chimeric polypeptide.

According to still further features in preferred embodiments, the promoter sequence is inducible by isopropyl beta-D-thiogalactoside.

According to still further features in preferred embodiments, the auto-cleavage results in auto-splicing.

According to still further features in preferred embodiments, the auto-splicing is auto-splicing of segments of the chimeric polypeptide flanking the autoprocessing segment.

According to a further aspect of the present invention there is provided a method of reversibly attaching a first substrate to a second substrate, the method comprising: (a) providing a chimeric polypeptide including an autoprocessing segment having an amino acid sequence set forth by SEQ ID NO: 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105 or 106 flanked by a first amino acid sequence capable of binding the first substrate and a second amino acid sequence capable of binding the second substrate, the chimeric polypeptide being capable of auto-cleavage when subjected to suitable conditions, to thereby release the first amino acid sequence from the second amino acid sequence; (b) exposing the first substrate and the second substrate to the chimeric polypeptide, thereby generating a complex including the first substrate attached via the chimeric polypeptide to the second substrate; and (c) subjecting the complex to the suitable conditions, thereby detaching the first substrate from the second substrate.

According to further features in preferred embodiments of the invention described below, each of the first and second substrates is independently selected from the group consisting of a molecule, a compound, a virus, and a cell.

According to still further features in preferred embodiments, the molecule is amylose or chitin.

According to still further features in preferred embodiments, the virus is a bacteriophage.

According to still further features in preferred embodiments, the chimeric polypeptide includes an affinity tag sequence, and the binding the first substrate or the binding the second substrate is via the affinity tag sequence.

According to still further features in preferred embodiments, the affinity tag sequence is a maltose-binding domain or a chitin-binding domain.

According to still further features in preferred embodiments, the autoprocessing segment is selected from the group consisting of BIL1_cloth, BIL2_cloth, BIL3_cloth, BIL4_cloth, BIL5_cloth, BIL6_cloth, BIL7_cloth, BIL9_cloth, BIL10_cloth, BIL11_cloth, 3875__87_magma, FhaB_manha, BIL2_neigo, BIL3_neigo, BIL5_neigo, BIL6_neigo, MafB1_neigo, MafB2_neigo, B0369+_neimeB, B0372+_neimeB, B0655+_neimeB, A2115_neime, BIL2_neimeC, BIL3_neimeC, BIL4_neimeC, BIL5_neimeC, BIL6_neimeC, MafB1_neimeC, FhaB1_psefl-PfO-1, FhaB1_psefl-SBW25, FhaB_psesy, SCP1.201_strco, 39__9_thefus, BIL1_gemob, BIL2_gemob, 0709_lepin, 3725_lepin, 3719_lepin, o665_myxxa, o1078_myxxa, o1070_myxxa, BIL1_strav, BIL2_strav, BIL3_strav, BIL1_pirsp, BIL1_chrvi, BIL1_glovi, BIL2_glovi, BIL3_glovi, BIL4_glovi, BIL5_glovi, BIL6_glovi, BIL7_glovi, o649_versp, o5687_versp, o3395_versp, II0519_brume, BIL2_magma, BIL3_magma, BIL4_magma, BIL5_magma, BIL6_magma, 06786_metex, 00126_rhoca, 00199_rhoca, 00459_rhoca, 00460_rhoca, 00746_rhoca, 00949_rhoca, 01216_rhoca, 01374_rhoca, 01523_rhoca, 01524_rhoca, 02710_rhoca, 03530_rhoca, 4825_rhosp, BIL2_rhosp, BIL1_silpo, BIL2_silpo, BIL3_silpo, BIL4_silpo, BIL5_silpo, BIL6_silpo, BIL7_silpo, BIL8_silpo, BIL9_silpo, BIL10_silpo, BIL11_silpo, BIL12_silpo, BIL13_silpo, BIL14_silpo, BIL15_silpo, BIL16_silpo, Bil1_rhile, BIL1_unknwn, and BIL2_unknwn.

According to still further features in preferred embodiments, the autoprocessing segment is derived from a protein of an organism belonging to a genus selected from the group consisting of *Brucella, Clostridium, Magnetospirillum, Mannheimia, Methylobacterium, Neisseria, Pseudomonas, Rhodobacter, Silicibacter, Streptomyces, Thermobifida, Rhizobium, Chromobacterium, Myxococcus, Leptospira, Pirellula, Gemmata, Gloeobacter* and *Verrucomicrobium*.

According to still further features in preferred embodiments, the organism is selected from the group consisting of *Rhodobacter capsulatus, Rhodobacter sphaeroides, Silicibacter pomeroyi, Brucella melitensis, Brucella suis, Magnetospirillum magnetotacticum, Methylobacterium extorquens, Rhizobium leguminosarum, Neisseria meningitidis, Neisseria meningitidis, Neisseria meningitidis, Neisseria gonorrhoeae, Chromobacterium violaceum, Pseudomonas syringae, Pseudomonas fluorescens, Pseudomonas fluorescens, Mannheimia haemolytica, Myxococcus xanthus, Leptospira interrogans, Streptomyces coelicolor, Streptomyces avermitilis, Thermobifida fusca, Clostridium thermocellum, Pirellula* species 1, *Gemmata obscuriglobus, Gloeobacter violaceus*, and *Verrucomicrobium spinosum*.

According to still further features in preferred embodiments, the auto-cleavage results in removal of a segment of the chimeric polypeptide adjacent to an amino terminal end or a carboxy terminal end of the autoprocessing segment.

According to still further features in preferred embodiments, the segment of the chimeric polypeptide adjacent to the autoprocessing segment is an amino terminal segment or a carboxy terminal segment of the chimeric polypeptide.

According to still further features in preferred embodiments, the segment of the chimeric polypeptide adjacent to the carboxy terminal end of the autoprocessing segment includes an amino acid residue comprising a nucleophilic group at an amino terminal end thereof.

According to still further features in preferred embodiments, the nucleophilic group is a hydroxyl group.

According to still further features in preferred embodiments, the amino acid residue is a threonine residue.

According to still further features in preferred embodiments, the segment of the chimeric polypeptide adjacent to the amino terminal end of the autoprocessing segment includes a serine amino acid residue at a carboxy terminal end thereof.

According to still further features in preferred embodiments, the chimeric polypeptide is capable of the auto-cleavage under a condition selected from the group consisting of a temperature selected from a range of 33° C. to 41° C., a pH selected from a range of pH 7.8 to pH 8.2, and a concentration of dithiothreitol selected from a range of 0.1 mM to 20 mM.

The present invention successfully addresses the shortcomings of the presently known configurations by providing novel chimeric polypeptides capable of defined auto-cleaving, including auto-cleaving resulting in defined auto-splicing, polynucleotides suitable for expressing such polypeptides, and methods of using such polypeptides and polynucleotides to purify proteins, affinity-select display phages, and post-translationally ligate proteins together.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1a is a sequence alignment diagram of the amino acid sequences of various Type A BIL domains (SEQ ID NOs: 8-62). The names of the domains and the amino acid sequence coordinates of their amino terminal residues in their host proteins are indicated to the left of the sequence. Numbers indicated in parentheses indicate the amino acid residue length of an intervening amino acid sequence which may have any amino acid sequence. Dashed lines have been inserted to assist in visualizing the alignments.

FIG. 1b is a sequence alignment diagram of the amino acid sequences of various Type B BIL domains (SEQ ID NOs: 63-104). The names of the domains and the amino acid sequence coordinates of their amino terminal residues in their host proteins are indicated to the left of the sequence. Numbers indicated in parentheses indicate the amino acid residue length of an intervening amino acid sequence which may have any amino acid sequence. Dashed lines have been inserted to assist in visualizing the alignments.

FIG. 2a is a sequence diagram depicting an amino acid sequence motif (SEQ ID NO: 105) exclusively defining amino acid sequences of a subset of Type A BIL domains, including: 39_9_thefus, SCP1.201_strco, 3875_87_magma, B0372+_neimeB, B0655+_neimeB, A2115_neime, MafB1_neimeC, BIL2_neimeC, BIL4_neimeC, BIL5_neimeC, BIL6_neimeC, MafB1_neigo, BIL2_neigo, BIL3_neigo, MafB2_neigo, BIL5_neigo, BIL6_neigo, FhaB_psesy, FhaB_manha, FhaB1_psefl-PfO-1, FhaB1_psefl-SBW25, BIL6_cloth, BIL5_cloth, BIL2_cloth, BIL4_cloth, BIL1_cloth, BIL8_cloth, BIL9_cloth, BIL1_gemob, BIL2_gemob, 0709_lepin, 3725_lepin, o1078_myxxa, o1070_myxxa, BIL1_strav, BIL2_strav, BIL3_strav, BIL1_pirsp, BIL1_chrvi, o3395_versp, o5687_versp, o649_versp, BIL1_glovi, BIL2_glovi, BIL3_glovi, and BIL4_glovi. Amino acid residues are indicated in standard single-letter code. X—any amino acid; X(1-100)—any amino acid sequence composed of 1 to 100 amino acid residues.

FIG. 2b is a sequence diagram depicting an amino acid sequence motif (SEQ ID NO: 106) exclusively defining amino acid sequences of a subset of Type B BIL domains, including: 4825_rhosp, BIL2_rhosp, 00588_rhoca, 02710_rhoca, 01524_rhoca, 01523_rhoca, 00126_rhoca, 01216_rhoca, 00949_rhoca, 01374_rhoca, 00459_rhoca, 00460_rhoca, 00746_rhoca, 03530_rhoca, 00199_rhoca, BIL3_magma, BIL4_magma, BIL1_brusu, BIL1_unknwn, BIL2_unknwn, 06786_metex, BIL1_silpo, BIL2_silpo, BIL3_silpo, BIL4_silpo, BIL5_silpo, BIL6_silpo, BIL7_silpo, BIL8_silpo, BIL9_silpo, BIL10_silpo, BIL11_silpo, BIL12_silpo, BIL13_silpo, BIL14_silpo, BIL15_silpo, BIL16_silpo, BIL1_rhile, and II0519_brume. Amino acid residues are indicated in standard single-letter code. X—any amino acid; X(1-100)—any amino acid sequence composed of 1 to 100 amino acid residues.

FIGS. 3a-z are block-logo diagrams depicting conserved amino acids of Hint-like motifs of Type A BIL domains (FIGS. 3a-g) and Type B BIL domains (FIGS. 3h-o) and of homologous Hint motifs of Hog proteins (FIGS. 3p-t) and inteins (FIGS. 3u-z). Unique BIL domain motifs are underlined with hatched lines. Motifs are ordered left to right in the amino to carboxy terminal positions along the protein sequences. Similar motifs are vertically aligned. The motifs are shown as sequence logos in which the heights of amino acid letter designations are proportional to their degree of conservation in each position. Protein splicing active site residues of intein Hint domains are indicated by asterisks. Motifs were identified and are displayed as previously described (Pietrokovski S., 1998. Protein Sci. 7, 64). The BIL domain motifs shown include sequences described in FIGS. 1a-b and Tables 1-2. The intein and hedgehog Hint domain sequences were obtained from previously published sources (Aspock G., 1999. Genome Res. 9, 909; Pietrokovski S., 2001. Trends Genet. 17, 465). The amino acid residue position shown forming the carboxy terminal end of the motif depicted in FIG. 3z actually represents the amino acid residue forming the amino terminal end of the carboxy terminal extein. Only intein and hedgehog motifs common to Hint domains are shown.

In FIG. 5a, molecular weights ("mw" lane) were further estimated using unlabeled protein markers (dotted lines). In FIG. 5b [MBP-CBD]' and [MBP]' indicate splicing and amino terminal cleavage products derived from MBP-RspBIL2-CBD. These fragments migrated at molecular weights greater than those the corresponding control fragments due to their containing residual BIL2_rhosp-flanking amino acid residues as a result of the pC2C-RspBIL2 cloning scheme described under Materials and Methods. Expected molecular weights of identified fragments are indicated in parentheses. The expected molecular weights of MBP-PsyBIL-CBD and of its carboxy terminal cleavage product MBP-PsyBIL, and its MBP-CBD splicing product were 66.3 and 59.1, and 50.6 kDa, respectively.

FIG. 5c is a diagram of the amino acid sequence of FhaB_psesy (SEQ ID NO: 107) depicting the putative protein splicing motifs (underlined) and catalytic residues (double-underlined) responsible for auto-cleavage/-splicing activity by this Type A BIL domain.

FIG. 6a depicts Coomassie Blue staining of chitin (lane 2) or amylose (lane 3) affinity column separated protein. Lane 4 is a control showing protein from E. coli transformed with pC2C to overexpress MBP-CBD ("MC" lane) chimeric protein. Fragments corresponding to the MBP-PsyBIL carboxy terminal auto-cleavage product and the MBP-CBD auto-splicing product of the chimera are indicated. FIG. 6b is an autoradiograph depicting Western immunoblotting analysis of separated protein following purification on chitin beads. Both chitin purified samples from E. coli transformed with pC2C-PsyBIL or control plasmid pC2C to overexpress MBP-PsyBIL-CBD or MBP-CBD chimeric proteins, respectively, were separated in duplicate lanes and blotted onto a single nitrocellulose membrane. The membrane was cut in half and each sample was reacted in duplicate with either anti-MBP (anti-M) or anti-CBD (anti-C) antibodies. Both anti-M and anti-C antibodies reacted with the protein band corresponding to the mass of the MBP-CBD product. Protein bands corresponding to MBP-PsyBIL and MBP products, that appear following purification on chitin beads result from non specific binding by excess amounts of overexpressed protein. Expected molecular weights of identified fragments are indicated in parentheses. The expected molecular weights of MBP-PsyBIL-CBD and of its carboxy terminal cleavage product MBP-PsyBIL, and its MBP-CBD splicing product were 66.3 and 59.1, and 50.6 kDa, respectively.

FIG. 7 is an amino acid sequence diagram depicting positioning of peptide sequences identified by MALDI peptide mass mapping analysis within the amino acid sequence of the MBP-CBD splicing product (SEQ ID NO: 108). Twenty-five tryptic peptide masses (underlined) were assigned to the amino acid sequence of the MBP-CBD protein, corresponding to 49% coverage of the MBP-CBD sequence. Lettering in non-bold/italic font indicates the amino acid sequence of the MBP tag, and the amino acid sequence of the CBD tag (amino acids 394-461) is indicated in bold+italic font. The peptide corresponding to amino acids 388-396 contains the BIL domain splice site between amino acids Ser393 and Thr394.

FIG. 8 is an amino acid sequence diagram depicting MALDI peptide mapping of the 59.3 kDa MBP-PsyBIL carboxy terminal cleavage product (SEQ ID NO: 109). Underlined sequences correspond to peptides detected by MALDI. Lettering in non-bold/italic font indicates the amino acid sequence of the MBP tag and that in bold/italic font indicates the amino acid sequence of the PsyBIL domain. The carboxy terminal end of the protein, asparagine N541 represents the carboxy terminal of the PsyBIL domain. The expected molecular weights of MBP-PsyBIL-CBD and of its carboxy terminal cleavage product MBP-PsyBIL, and its MBP-CBD splicing product were 66.3 and 59.1, and 50.6 kDa, respectively.

FIG. 10a is a photograph of a Coomassie blue stained electrophoretic separation of in-vivo expressed MBP-RspBIL2a-CBD chimera affinity purified on amylose depicting C-terminal cleavage activity ("MB" product). FIG. 10b is a photograph of a Western immunoblotting analysis depicting C-terminal cleavage activity ("MB" product) using anti-MBP antibodies (anti-M). FIG. 10c is an autoradiograph of an SDS-PAGE separation of the in-vitro translated, [$^{35}$S]-methionine-labeled chimera depicting C-terminal cleavage activity ("MB" product). M-MBP specific fragment, MB-MBP-BIL specific fragment, MBC-intact chimera.

FIG. 11a is a photograph of a Coomassie blue stained electrophoretic separation of chimera protein products depicting N-terminal cleavage activity of protein products affinity purified on chitin ("BC" product) and affinity purified on amylose ("M" product). FIG. 11b is a photograph of a Western immunoblotting analysis depicting N-terminal cleavage activity using anti-CBD antibody as a probe ("BC" product) and anti-MBP antibody as a probe ("M" product). BC-BIL-CBD specific fragment, M-MBP specific fragment, MB-MBP-BIL specific fragment, MBC-intact chimera.

FIGS. 12a-c are electrophoretic analyses depicting autoprocessing and by in-vivo expressed MBP-BIL4_cloth-CBD chimera. FIG. 12a is a photograph of a Western immunoblotting analysis of amylose (lane "A") or chitin (lane "C") purified protein products depicting auto-splicing activity using anti-CBD antibody as a probe ("MC" product). FIG. 12b is a photograph of a Western immunoblotting analysis of amylose (lane "A") or chitin (lane "C") purified protein products depicting auto-splicing activity ("MC" product). FIG. 12b also shows carboxy terminal auto-cleavage of protein products affinity purified via amylose based affinity chromatography (lane "A", "MB" product). FIG. 12c is a photograph of a Coomassie blue stained electrophoretic separation of protein products isolated via amylose based (lane "A") or chitin based (lane "C") affinity chromatography depicting auto-splicing activity ("MC" species). FIG. 12c also shows carboxy terminal auto-cleavage of protein products affinity purified via amylose based affinity chromatography (lane "A", "MB" species). Note the very small amounts of the uncleaved precursor (lane "C", "MBC" species) suggesting very efficient autoprocessing activity by this chimera. M-MBP specific fragment, MB-MBP-BIL specific fragment, MBC-intact chimera.

DESCRIPTION OF THE PREFERRED EMBODIMENTS

Figure 4A:
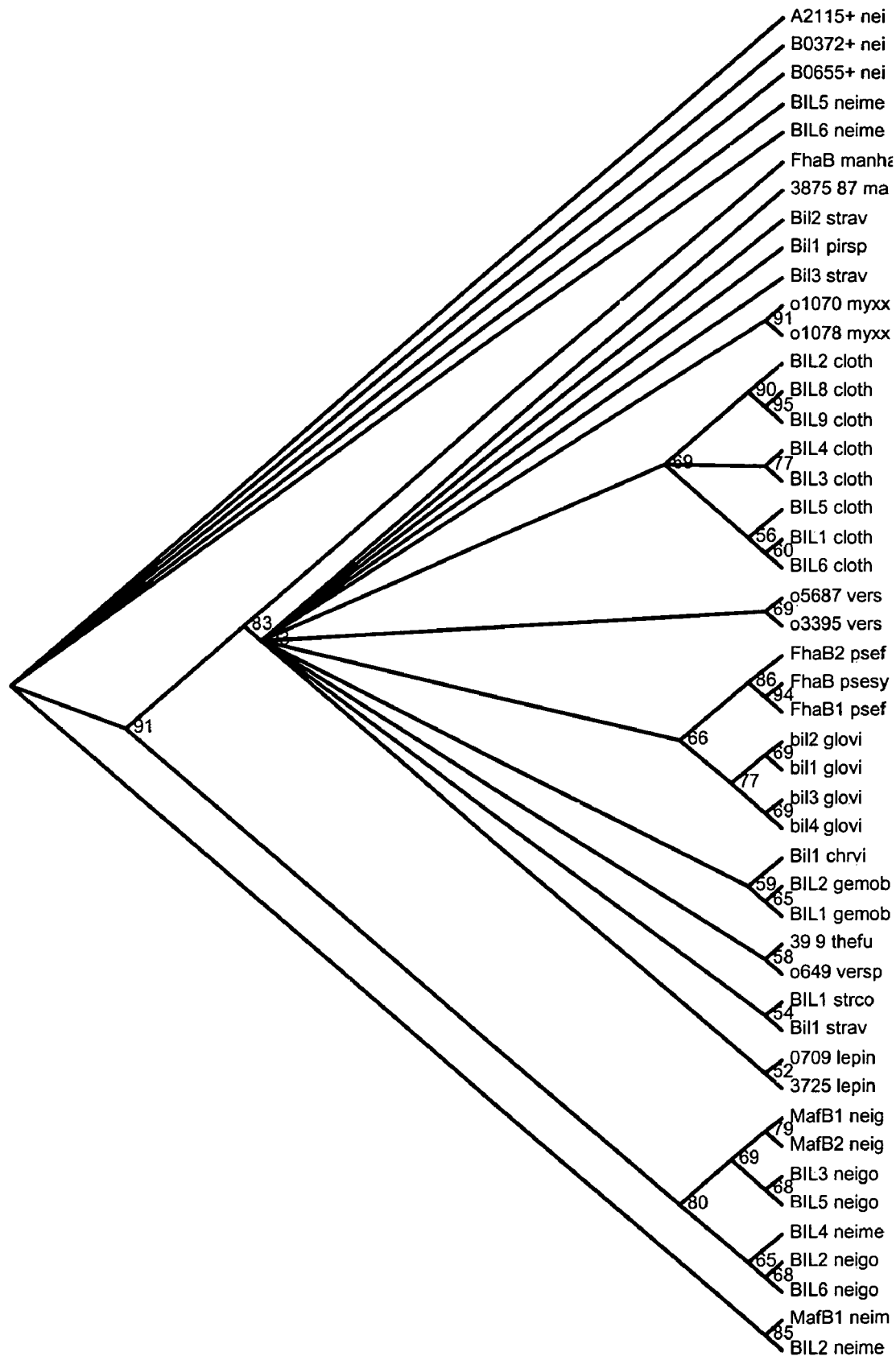
FIGS. 4a-b are dendrograms depicting phylogenetic relationships of Type A and Type B BIL domains, respectively.

The present invention is of chimeric autoprocessing polypeptides, polynucleotides encoding such polypeptides, and uses of such polypeptides and polynucleotides for reversibly binding proteins to specific substrates, reversibly binding specific substrates to each other, and auto-splicing amino acid sequences. Specifically, the present invention can be used to purify proteins, to affinity-select display phages, and to post-translationally ligate proteins together.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Autoprocessing polypeptides, polypeptides having the capacity to post-translationally auto-cleave and/or auto-splice, can be used to greatly facilitate various industrially and scientifically important biochemical procedures, as described above. For example, such autoprocessing polypeptides can be used in applications which involve reversible binding of proteins to specific substrates, such as protein purification, and reversible binding of specific substrates to each other, such as affinity-selection of display phages.

Various chimeric autoprocessing polypeptides and methods of using such have been described in the prior art (reviewed in: Perler and Adam, 2000. Curr Opin Biotechnol. 11, 377-83; Paulus H., 2000. Annu Rev Biochem. 69, 447).

However, all such prior art chimeric autoprocessing polypeptides suffer from various drawbacks. As described above, these drawbacks include suboptimal activity, poor stability, insolubility, requirement for strong auxiliary nucleophiles causing undesirable modifications at carboxy termini of cleaved amino terminal fragments, and undesirable amino terminal cleavages.

Thus, all prior art approaches have failed to provide optimal chimeric autoprocessing polypeptides for use in protein engineering.

While reducing the present invention to practice it was uncovered that the chimeric polypeptides of the present invention display efficient auto-cleavage, including autocleavage resulting in auto-splicing.

The chimeric polypeptides of the present invention comprise novel autoprocessing domains characterized by unique amino acid sequences, unique host protein/organism type origins, and unique natural biological capacities. Thus, the chimeric polypeptides of the present invention are highly novel and significantly enlarge and enhance the prior art spectrum of available types of chimeric autoprocessing polypeptides and their possible applications.

Thus, according to one aspect of the present invention, there are provided chimeric polypeptides having efficient auto-cleavage activity and comprising an autoprocessing segment having an amino acid sequence set forth by SEQ ID NO: 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105 or 106.

Preferably, the amino acid sequence of the autoprocessing segment is set forth by SEQ ID NO: 12, 31, 76, or 77.

As used herein, the phrase "auto-cleavage activity" refers to cleavage of a polypeptide of the present invention in a region adjacent to the autoprocessing segment. Auto-cleavage occurs following exposure of the polypeptide of the present invention to suitable conditions in the absence of any other protein. Suitable auto-cleavage conditions are described hereinbelow.

Depending on the purpose, application and configuration, the polypeptides of the present invention may display different types of auto-cleavage activity.

Preferably, the auto-cleavage activity of the polypeptides of the present invention results in removal of a segment of the polypeptide adjacent to the amino terminal end or the carboxy terminal end of the autoprocessing segment.

Preferably, the segment of the polypeptide adjacent to the autoprocessing segment is an amino terminal segment or a carboxy terminal segment of the polypeptide.

According to one embodiment, the polypeptides of the present invention may comprise the autoprocessing domain as an amino terminal segment thereof. In this configuration, the polypeptides of the present invention may display removal of the segment thereof adjacent to the carboxy terminal end of the autoprocessing segment, i.e., the segment removed is the carboxy terminal segment of the polypeptide.

According to further embodiments, the polypeptides of the present invention may comprise the autoprocessing domain as a carboxy terminal segment thereof. In this configuration, the polypeptides of the present invention may display removal of the segment thereof adjacent to the amino terminal end of the autoprocessing segment, i.e., the segment removed is the amino terminal segment of the polypeptide.

According to yet further embodiments, the polypeptides of the present invention may comprise the autoprocessing domain as an internal segment of the polypeptide. In this configuration, the polypeptides of the present invention may display one or more of the following: removal of a segment adjacent to the amino terminal end of the autoprocessing segment, (i.e., the amino terminal segment of the polypeptide); removal of a segment adjacent to the carboxy terminal end thereof (i.e., the carboxy terminal segment of the polypeptide); removal of both the carboxy and amino terminal segments.

In some cases, removal of both segments may result in subsequent covalent fusion between the removed segments and, as such, auto-splicing of the polypeptide.

As used herein, the term "auto-splicing" refers to covalent bond formation between the amino acid residue forming the carboxy terminal end of a segment of the polypeptide adjacent to the amino terminal end of the autoprocessing domain and the amino acid residue forming the amino terminal end of a segment of the polypeptide adjacent to the carboxy terminal end of the autoprocessing domain.

As is illustrated in the Examples section which follows, the polypeptides of the present invention demonstrate such auto-splicing activity.

The polypeptides of the present invention may be advantageously used to post-translationally ligate essentially any protein to essentially any other protein via formation of a covalent bond between amino acid residues forming complementary terminal ends thereof. This may be effected by using a polypeptide of the present invention comprising the proteins to be ligated in the configuration described hereinabove enabling auto-splicing to yield the desired ligation product.

Preferably, the covalent bond is a peptide bond. Alternately, as described above, the covalent bond may be an ester bond, such as the ester bond formed during auto-cleavage of prior art autoprocessing polypeptides.

Depending on the application and purpose, auto-cleavage of the polypeptide may be specifically induced under suitable conditions, preferably a specific temperature, pH, or concentration of dithiothreitol (DTT).

Preferably, the temperature is in the range of 33 to 41° C., more preferably the temperature is in the range of 34 to 40° C., more preferably the temperature is in the range of 35 to 39° C., more preferably the temperature is in the range of 36 to 38° C., more preferably the temperature is in the range of 36.5 to 37.5° C., and most preferably the temperature is 37.0° C.

Preferably, the pH is in the range of pH 7.8 to 8.2, more preferably the pH is in the range of pH 7.9 to 8.1, and most preferably the pH is 8.0.

Preferably, the concentration of dithiothreitol is in the range of 0.1-20 millimolar, more preferably the concentration of dithiothreitol is in the range of 0.2-10 millimolar, more preferably the concentration of dithiothreitol is in the range of 0.5-5 millimolar, and most preferably the concentration of dithiothreitol is in the range of 1.0-2.0 millimolar.

Without being bound to a paradigm, the present inventors are of the opinion that auto-cleavage activity, in addition to being governed by the amino acid sequence of the autoprocessing segment, is also influenced by the amino acid sequence of the segments adjacent to the autoprocessing segment.

For example, the present inventors are of the opinion that in configurations in which the polypeptide comprises a carboxy terminal segment adjacent to the carboxy terminal end of the autoprocessing segment, the efficiency of cleavage may be enhanced if such a carboxy terminal segment includes at its amino terminal end, an amino acid residue comprising a nucleophilic group such as a sulfhydryl group, or more preferably a hydroxyl group.

As such, in cases wherein the polypeptide of the present invention includes a carboxy terminal segment adjacent to the autoprocessing segment, the amino acid residue forming the amino terminal end of such a carboxy terminal segment is preferably cysteine, serine, or more preferably threonine. As is illustrated in the Examples section below, polypeptides of the present invention having such a carboxy terminal segment display auto-cleavage of the carboxy terminal segment, including auto-cleavage resulting in auto-splicing.

In configurations wherein the polypeptide of the present invention includes an amino terminal segment adjacent to the autoprocessing segment, the amino acid residue forming the carboxy terminal end of such an amino terminal segment is preferably serine. As is illustrated in the Examples section below, polypeptides of the present invention having such an amino terminal segment display auto-cleavage of the amino terminal segment, including auto-cleavage resulting in auto-splicing.

It is recognized in the art that certain prior art autoprocessing segments lack the capacity to auto-cleave the bond attaching a given terminal end of the autoprocessing segment to particular flanking amino acid residues (Perler and Adam, 2000. Curr Opin Biotechnol. 11, 377-83).

In particular, certain prior art autoprocessing amino acid sequences lack the capacity to auto-cleave the bond attaching their amino terminal end to a flanking serine residue. As is illustrated in the Examples section which follows, and in sharp contrast to polypeptides containing such prior art autoprocessing amino acid sequences, the polypeptides of the present invention possess the capacity to auto-cleave such a bond.

Specific amino acid sequences of autoprocessing domains comprised in the polypeptides of the present invention may be obtained by referring to Table 1, FIGS. 1a-b, and FIGS. 2a-b of the Examples section below. Table 1 provides database coordinates which can be used to retrieve the nucleic acid sequences encoding such amino acid sequences. Such amino acid sequences may easily be determined from such nucleic acid sequences by the ordinarily skilled artisan using a suitable nucleic acid-to-amino acid sequence translation software, such as, for example translation software made publicly available by the National Center for Biotechnology Information (NCBI) or the European Molecular Biology Laboratory (EMBL) on the World Wide Web (WWW). FIGS. 1a-b provide specific amino acid sequences of various autoprocessing domains comprised in the polypeptides of the present invention. FIGS. 2a-b provide amino acid sequence motifs which define autoprocessing domains comprised in the polypeptides of the present invention.

For example, as is shown in the Examples section which follows, polypeptides of the present invention comprising autoprocessing segments FhaB_psesy (SEQ ID NO: 12), BIL4_cloth (SEQ ID NO: 31), 4825_rhosp (SEQ ID NO: 76) or BIL2_rhosp (SEQ ID NO: 77) display auto-cleavage activity, including auto-cleavage activity resulting in auto-splicing.

The polypeptides of the present invention may further comprise at least one affinity tag capable of specifically binding a substrate. As is further described hereinbelow, the affinity tag type depends on the intended use of the polypeptide.

As used herein, the phrase "affinity tag" refers to any moiety (preferably a peptide or polypeptide moiety) which is capable of specifically binding a substrate.

While the substrate can be essentially any substance or particle which can be specifically bound by the affinity tag, the substrate is preferably a molecule, a compound, a virus, or a cell.

The polypeptides of the present invention may comprise essentially any affinity tag.

Examples of peptide/polypeptide affinity tags include streptavidin, His-tags, strep-tags, epitope tags, maltose-binding proteins, and chitin-binding domains.

His-tags (histidine tags) consist of a chain of 2 to 10, most preferably 6, contiguous histidine amino acid residues. His-tags have the capacity to specifically bind substrates including nickel. Ample guidance regarding tagging polypeptides with His-tags is available in the literature of the art (for example, refer to: Sheibani N. 1999. Prep Biochem Biotechnol. 29:77). Purification of molecules comprising histidine tags is routinely effected using nickel-based automatic affinity column purification techniques. A suitable capture ligand for histidine-tagged molecules is the anti histidine tag single chain antibody 3D5 (Kaufmann, M. et al., 2002. J Mol. Biol. 318. 135-47).

Examples of epitope tags include an 11-mer Herpes simplex virus glycoprotein D peptide, and an 11-mer N-terminal bacteriophage t7 peptide, being commercially known as HSVTag and t7Tag, respectively (Novagen, Madison, Wis., USA), and 10- or 9-amino acid c-myc or *Hemophilus influenza* hemagglutinin (HA) peptides, which are recognized by the variable regions of monoclonal antibodies 9E10 and 12Ca5, respectively.

Strep-tags are peptides having the capacity to specifically bind streptavidin. Ample guidance regarding the use of strep-tags is provided in the literature of the art (see, for example: Schmidt, T G M. and Skerra, A. 1993. Protein Eng. 6, 109; Schmidt T G M. et al., 1996. Journal of Molecular Biology 255, 753-766; Skerra A. and Schmidt T G M., 1999. Biomolecular Engineering 16, 79-86; Sano T. and Cantor C R. 2000. Methods Enzymol. 326, 305-11; Sano T. et al., 1998. Journal of Chromatography B 715, 85-91).

Preferably, the affinity tag is a maltose-binding domain or a chitin-binding domain.

Preferably, the maltose-binding domain is malE-encoded maltose-binding protein (MBP). Ample guidance regarding the use of maltose-binding protein as an affinity tag is provided in the Examples section which follows and in the literature of the art (see, for example: Guan M. et al., 2002. Protein Expr Purif. 26, 229-34; Cattoli F. and Sarti G C., 2002. Biotechnol Prog. 18, 94-100).

In cases where the affinity tag is a maltose-binding protein, the substrate is preferably amylose, a specific ligand of such an affinity tag. Alternately, the substrate may be maltose, also a specific ligand of such an affinity tag.

As is shown in the Examples section below, polypeptides of the present invention comprising maltose-binding protein (MBP) can specifically bind a support including amylose.

Preferably, the chitin-binding domain is *B. circulans* cbd-encoded chitin binding domain (CBD). Ample guidance regarding the use of chitin-binding domain as an affinity tag is provided in the Examples section which follows and in the literature of the art (see, for example: Humphries H E. et al., 2002. Protein Expr Purif. 26, 243-8; Chong S. et al., 1997. Gene 192, 271-81).

In cases where the affinity tag is cbd-encoded chitin binding domain (CBD), the substrate is preferably chitin, a specific ligand of such an affinity tag.

As is illustrated in the Examples section which follows, polypeptides of the present invention comprising cbd-encoded chitin-binding domain can specifically bind a support including chitin.

The polypeptides of the present invention can be generated using chemical synthesis approaches or preferably recombinant techniques.

While reducing the present invention to practice, nucleic acid sequences encoding polypeptides having putative autoprocessing segments were identified in nucleic acid sequence databases (see Examples section below for further detail). The sequences were analyzed and the autoprocessing segment encoding regions were identified and used to generate polynucleotides encoding the polypeptides of the present invention.

Thus, according to another aspect of the present invention there is provided a polynucleotide sequence which encodes the auto-cleavable polypeptide of the present invention.

The polynucleotides of the present invention can be assembled from genomic, and/or complementary sequences.

As used herein, the phrase "complementary sequence" refers to a polynucleotide having a nucleic acid sequence resulting from reverse transcription of messenger RNA using a reverse transcriptase or any other RNA dependent DNA polymerase. Such sequences can be subsequently amplified in-vivo or in-vitro using a DNA dependent DNA polymerase.

As used herein, the phrase "genomic sequence" refers to a polynucleotide derived from a chromosome which thus reflects a contiguous portion of a chromosome.

In the case of a polynucleotide of the present invention encoding an autoprocessing domain expressed in a prokaryotic organism, the nucleic acid sequence encoding the autoprocessing domain may be conveniently generated via polymerase chain reaction (PCR) amplification using genomic DNA of the prokaryotic organism as a template.

Alternately, in the case of a polynucleotide of the present invention encoding an autoprocessing domain expressed in a eukaryotic organism, the nucleic acid sequence encoding the autoprocessing domain may be conveniently generated via PCR amplification using a cDNA library derived from the organism as a template.

Suitable oligonucleotide primers for PCR amplifying nucleic acid sequences encoding specific autoprocessing domains comprised in polypeptides of the present invention can be designed using the nucleic acid sequences identified by the database coordinates provided in Table 1 of the Examples section which follows.

For example, as is illustrated in the Examples section below, oligonucleotide primers suitable for PCR amplifying nucleic acid sequences encoding the autoprocessing domains FhaB_psesy, or BIL2_rhosp were derived from nucleic acid sequences retrieved using the relevant database coordinates provided in Table 1 of the Examples section below. The nucleic acid sequences of such primers are set forth by SEQ ID NOs: 4-5, or 6-7, respectively. Ample guidance for determining suitable reaction conditions for amplifying nucleic acid sequences encoding the aforementioned autoprocessing domains is provided in the Examples section which follows. PCR amplification of nucleic acid sequences is a commonly performed procedure and suitable primers and reaction conditions for a broad range of such procedures can generally be routinely determined by one of ordinary skill in the art, for example via suitable software, such as, for example, OLIGO 4.0 (National Biosciences, Plymouth, Minn.).

It will be appreciated that since autoprocessing activity is a characteristic of the amino acid sequence, one of ordinary skill in the art may alternatively use the amino acid sequences provided herein as a template for designing nucleic acid sequences which encode such amino acid sequences, and which take into consideration parameters such as codon usage which may increase the efficiency of expression of such sequences in specific organisms.

As described above, the polypeptides of the present invention may further comprise at least one affinity tag. In order to produce polypeptides of the present invention comprising affinity tags, coding nucleotides are formed comprising nucleic acid sequences encoding such affinity tags.

As described hereinabove, methods of generating nucleic acid sequences encoding affinity tags are well known to one of ordinary skill in the art. For example, nucleic acid sequences encoding affinity tags can be advantageously generated by PCR amplification of nucleic acid sequences encoding such affinity tags.

For example, as described and demonstrated in the Examples section which follows, suitable oligonucleotide primers for amplification of nucleic acid sequences encoding B. circulans cbd-encoded chitin-binding domain are set forth in SEQ ID NOs: 1-2.

Alternately, autoprocessing domains may be conveniently cloned into nucleic acid constructs configured for expressing fusion proteins comprising an affinity tag fused to a polypeptide encoded by a nucleic acid insert cloned into such a construct.

As is shown in the Examples section below, polynucleotides of the present invention comprising nucleic acid sequences encoding the affinity tag maltose-binding protein were assembled by cloning a nucleic acid sequence encoding an autoprocessing domain of the polypeptides of the present invention into the expression construct pMALC2 (New England Biolabs) which is designed to express fusion proteins comprising maltose-binding protein fused to a polypeptide encoded by a cloned insert.

Such nucleic acid constructs can be advantageously used to insert and/or express a chimeric polynucleotide within a host cell.

Thus, according to yet another aspect of the present invention there is provided a nucleic acid construct comprising a polynucleotide of the present invention.

The nucleic acid constructs of the present invention preferably comprise suitable promoter sequences so as to enable efficient expression of the polynucleotide of the present invention in an expression system.

Expression of the polynucleotides of the present invention may be conveniently controlled using an inducible promoter. A suitable inducible promoter is an isopropyl beta-D-thiogalactoside (IPTG)-inducible promoter, such as a T7 promoter. As described in the Examples section which follows, a T7 promoter can be used to drive IPTG-inducible expression of a polynucleotide of the present invention in a suitable cell-free expression system or in a cellular expression system.

IPTG-induced expression of polynucleotides under the regulatory control of T7 promoters is widely practiced in the art by the ordinarily skilled practitioner and ample guidance regarding the use of such promoters is available in the literature of the art (see, for example, Sambrook et al., infra).

The nucleic acid constructs of the present invention can be used to produce the polypeptides of the present invention in a suitable expression system.

Thus, according to still another aspect of the present invention there is provided a method of generating a polypeptide of the present invention.

The method is effected by generating a chimeric amino acid sequence including an autoprocessing segment of the present invention. Preferably the chimeric amino acid sequence is generated by expressing a polynucleotide of the present invention in an expression system suitable for generating the chimeric amino acid sequence from the chimeric polynucleotide.

The nucleic acid constructs of the present invention can be used to express the polypeptides of the present invention in various expression systems, including any cellular or cell-free expression systems suitable for expressing recombinant proteins such as the polypeptides of the present invention.

When used to express the polypeptides of the present invention in a cell-free expression system, the constructs of the present invention may be advantageously expressed in any suitable in-vitro transcription/translation system.

Numerous in-vitro transcription/translation systems are commercially available for expressing recombinant proteins such as the polypeptides of the present invention.

For example, a suitable cell-free expression system for expressing nucleic acid constructs of the present invention is an E. coli S30 extract expression system, as described and as demonstrated in the Examples section below.

Numerous cellular expression systems, including yeast, bacterial, insect, and mammalian cells can be employed to express the nucleic acid constructs of the present invention.

As described and illustrated in the Examples section which follows, the polypeptides of the present invention may be advantageously expressed in E. coli by transforming E. coli with the nucleic acid constructs.

Transformation of E. coli with nucleic acid constructs is a routine procedure widely practiced in the art (see, for example, Sambrook et al., infra).

For example, for expression of the polypeptides of the present invention using the nucleic acid constructs of the present invention in E. coli, competent cells capable of DNA uptake may be prepared from cells harvested in exponential growth phase and rendered competent via the widely practiced $CaCl_2$ method. Addition of $MgCl_2$ or RbCl to the transformation reaction medium may be employed to increase transformation efficiency. Alternative transformation methods include methods such as electroporation or host cell protoplast transformation.

As described hereinabove, the capacities of the polypeptides of the present invention to specifically bind substrates and to auto-cleave can be advantageously used in various practical applications involving reversible binding of substrates, such as protein purification.

Thus, according to a further aspect of the present invention there is provided a method of purifying a protein.

The method is effected by generating a polypeptide of the present invention comprising an autoprocessing segment being terminally attached to, or flanked by, an amino acid sequence of the protein, immobilizing the polypeptide to a support, and subjecting the immobilized polypeptide to suitable conditions for enabling auto-cleavage resulting in removal of the protein from the polypeptide.

According to a preferred embodiment, the polypeptide of the present invention is configured such that one terminal end of the autoprocessing segment is adjacent to a terminal segment of the polypeptide being the protein to be purified and the other terminal end of the autoprocessing segment is adjacent to a terminal segment of the polypeptide comprising an affinity tag.

According to this embodiment, the polypeptide of the present invention is preferably immobilized via a specific binding of the affinity tag to a specific ligand thereof included in the support. Optionally, in cases where auto-cleavage further results in detachment of the autoprocessing segment from the terminal segment of the polypeptide comprising the affinity tag, the method may advantageously further comprise the step of separating the protein from the autoprocessing segment so as to further facilitate purification of the protein. Such separation may be effected as described further hereinbelow.

According to another embodiment, the polypeptide of the present invention consists of a chimera comprising the autoprocessing segment fused to the protein to be purified.

According to this embodiment, the polypeptide of the present invention is preferably immobilized via a specific binding of the autoprocessing segment to a specific ligand of the autoprocessing segment included in the support.

According to yet another embodiment, the polypeptide of the present invention consists of an autoprocessing segment being flanked at its amino terminal end with an amino terminal segment of the amino acid sequence of the protein to be purified, and being flanked at its carboxy terminal end with the carboxy terminal segment of the amino acid sequence of the protein to be purified complementing the amino terminal segment of the amino acid sequence of the protein to be purified.

According to this embodiment, the polypeptide of the present invention is preferably immobilized via a specific binding of the autoprocessing segment to a specific ligand of the autoprocessing segment included in the support, and auto-cleavage results in auto-splicing of the complementary amino and carboxy terminal segments of the protein to be purified to thereby release the protein.

In embodiments in which the polypeptide of the present invention is immobilized via the autoprocessing segment, the specific ligand included in the support is preferably an antibody or antibody fragment capable of specifically binding the autoprocessing segment.

Purification of a protein according to the method of the present invention may be advantageously effected via standard affinity chromatography techniques. For example, a suitable support for immobilizing a polypeptide of the present invention may be an affinity resin coupled to a specific ligand of the polypeptide of the present invention packed in a standard affinity purification column. Following subjecting of the support-bound polypeptide of the present invention to conditions suitable for auto-cleavage thereof, the highly purified protein released from the support-bound autoprocessing segment may be conveniently recovered as a flow-through fraction eluted from the column.

In the case described hereinabove, wherein auto-cleavage further results in detachment of the autoprocessing segment from the support-bound segment of the polypeptide of the present invention, separating the protein from the autoprocessing segment may be effected analogously to the method described hereinabove by using such standard affinity chromatography techniques wherein the affinity resin includes a specific ligand of the autoprocessing segment.

Alternately, various methods suitable for separating such mixtures of polypeptides may be practiced by the ordinarily skilled artisan. Such techniques include, for example high-performance liquid chromatography (HPLC), size-exclusion chromatography, and similar methodologies.

Ample guidance regarding chromatographic isolation of proteins is widely available in the literature of the art (see, for example: Wilchek M. and Chaiken I., 2000. Methods Mol Biol 147, 1-6; Jack G W., 1994. Mol Biotechnol 1, 59-86; Narayanan S R., 1994. Journal of Chromatography A 658, 237-258; Nisnevitch M. and Firer M A., 2001. J Biochem Biophys Methods 49, 467-80; Janson J C. and Kristiansen T. in Packings and Stationary Phases in Chromatography Techniques. Unger K K. (ed.), Marcel Dekker, New York, pp. 747 (1990); Clonis Y D: HPLC of Macromolecules: A Practical Approach, IRL Press, Oxford, pp. 157 (1989); Nilsson J. et al., 1997. Protein Expr Purif. 11, 1-16).

As described in the Examples section which follows, amylose affinity ligand based column chromatography of a polypeptide of the present invention comprising the autoprocessing domain BIL2_rhosp flanked at its amino terminal end with an amino terminal segment including the affinity tag MBP, and flanked at its carboxy terminal end with the amino acid sequence of a protein to be purified resulted in column-retention of a segment of the polypeptide of the present invention lacking the amino acid sequence of the protein to be purified (FIG. 10a), thereby demonstrating the utility of the method of the present invention for purifying proteins.

Figure 11A:
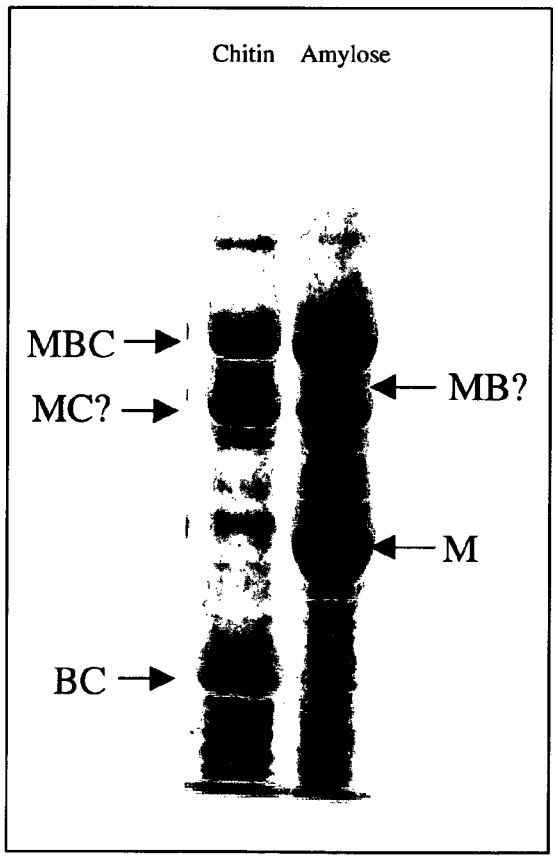
FIGS. 11a-b are electrophoretic analyses depicting N-terminal auto-cleavage by in-vivo expressed MBP-4825rhosp-CBD chimera.
Figure 11B:
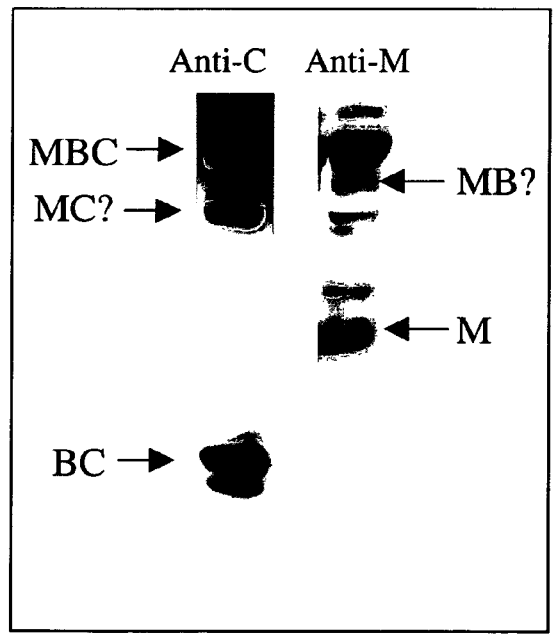

As described in the Examples section which follows, chitin affinity ligand based column chromatography of a polypeptide of the present invention comprising the autoprocessing domain 4825_rhosp flanked at its carboxy terminal end with an carboxy terminal segment including the affinity tag CBD, and flanked at its amino terminal end with the amino acid sequence of a protein to be purified resulted in column-retention of a segment of the polypeptide of the present invention lacking the amino acid sequence of the protein to be purified (FIG. 11b), thereby demonstrating the utility of the method of the present invention for purifying proteins.

According to the teachings of the present invention, the polypeptides of the present invention may include affinity tags flanking the autoprocessing segment.

Thus, according to yet a further aspect of the present invention there is provided a method of reversibly attaching a first substrate to a second substrate.

The first and second substrates may be the same or may be different.

The method is effected using a polypeptide of the present invention in which the autoprocessing segment is flanked by a first amino acid sequence capable of binding the first substrate and a second amino acid sequence capable of binding the second substrate, such that auto-cleavage releases the first amino acid sequence from the second amino acid sequence. Exposing the first substrate and the second substrate to the polypeptide of the present invention generates a complex including the first substrate attached via the polypeptide to the second substrate. Following generation thereof, the complex is subjected to suitable conditions for auto-cleavage, thereby detaching the first substrate from the second substrate.

Complex generation may be effected in various ways, depending on the application and purpose. For example, complex generation may be effected wherein neither, one or both substrates is included in, or consists of, a support specifically binding an affinity tag comprised in the polypeptide of the present invention.

According to a preferred embodiment, the method is used for reversibly attaching a first substrate being a protein displayed by a bacteriophage to a second substrate specifically binding the phage-displayed protein, which substrate being included in a support.

According to this embodiment, the method is effected using a polypeptide of the present invention comprising a first amino acid sequence having the capacity to specifically bind the substrate and a second amino acid sequences having the capacity to bind the phage-displayed protein.

The method according to this aspect of the present invention may be advantageously employed with phage-display libraries for selecting bacteriophages displaying a protein having high affinity to a specific substrate. This may be effected by exposing a phage display library to a support including a substrate being a target molecule to which a high affinity ligand is desired. Elements of the phage display library not being bound with high affinity to the support may be washed and recovery of phages specifically binding the substrate with high affinity via a displayed protein capable of specifically binding the target molecule with high affinity may be conveniently recovered by subjecting the support-bound phages to conditions suitable for auto-cleavage of the polypeptide of the present invention so as to effect the detachment thereof from the support.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Example 1

Bacterial-Intein Like (BIL) Domains

Novel Auto-Cleaving/Auto-Splicing Protein Domains

Autoprocessing polypeptides capable of auto-cleavage have been shown to be uniquely useful in a wide range of protein engineering applications, for example for protein purification without the requirement for proteases. However, all prior art autoprocessing polypeptides suffer from various drawbacks, including suboptimal activity, stability, solubility, and requirement for auxiliary molecules causing undesirable protein modifications. In order to enlarge and enhance the current repertoire of autoprocessing polypeptides, the present inventors have identified, generated and demonstrated the functionality of novel autoprocessing polypeptides, as follows.

Materials and Methods:

In order to identify novel auto-cleaving/-splicing proteins, databases storing genomic sequences of various organisms, including bacterial pathogens were searched for open reading frames (ORFs) coding for protein sequences containing Hint domains. Following identification of protein sequences containing Hint domains, such protein sequences were cloned and tested for auto-cleaving/-splicing activity, as described below.

Data sources: BILs were identified in bacterial genomes by searching the following databases: National Center for Biotechnology Information (NCBI) sequence databases for *Brucella melitensis* (*B. melitensis*) 16M, *Streptomyces coelicolor* (*S. coelicolor*) A3(2), *Neisseria meningitidis* (*N. meningitidis*) MC58, *N. meningitidis* Z2491, *Pseudomonas fluorescens* (*P. fluorescens*) PfO-1, *Leptospira interrogans* (*L. interrogans*) 56601, *Streptomyces avermitilis* (*S. avermitilis*) MA-468, *Pirellula* species 1, and *Chromobacterium violaceum* (*C. violaceum*) ATCC 12472 sequences; Integrated Genomics (http://www.integratedgenomics.com) sequence databases for *Rhodobacter capsulatus* (*R. capsulatus*) SB 1003 genomic sequences (Haselkorn et al., 2001. Photosynthesis Research 70, 43-52) and *Methylobacterium extorquens* (*M. extorquens*) AM1, Joint Genome Institute (http://www-jgi.doe.gov) sequence databases for *Rhodobacter sphaeroides* (*R. sphaeroides*) 2.4.1 (Mackenzie et al., 2001. Proc Natl Acad Sci USA. 99, 2275-2280), *Magnetospirillum magnetotacticum* (*M. magnetotacticum*) MS-1, *Clostridium thermocellum* (*C. thermocellum*) ATCC 27405, and *Thermobifida fusca* (*T. fusca*) YX genomic sequences; The Institute for Genomic Research (http://www.tigr.org) sequence databases for *Pseudomonas syringae* (*P. syringae*) DC3000 (Fouts et al., 2002. Proc Natl Acad Sci USA 99, 2275-2280), *Silicibacter pomeroyi* (*S. pomeroyi*) DSS-3, *Gemmata obscuriglobus* (*G. obscuriglobus*) UQM 2246, *Myxococcus xanthus* (*M.*

*xanthus*) DK1622, and *Verrucomicrobium spinosum* (*V. spinosum*) DSM 4136 sequences; The Sanger Institute (http://www.sanger.ac.uk) sequence databases for *Neisseria meningitidis* (*N. meningitidis*) FAM18, *P. fluorescens* SBW25, and *Rhizobium leguminosarum* (*R. leguminosarum*) bv. viciae 3841 sequences; University of Oklahoma, Advanced Center for Genome Technology (http://www.genome.ou.edu) sequence databases for *Neisseria gonorrhoeae* (*N. gonorrhoeae*) FA1090 genomic sequences; Baylor College of Medicine Human Genome Sequencing Center (http://www.hgsc.bcm.tmc.edu) sequence databases for *Mannheimia haemolytica* (*M. haemolytica*) PHL213 genomic sequences; and Kazusa DNA Research Institute database (Japan; http://www.kazusa.orjp) for *Gloeobacter violaceus* (*G. violaceus*) PCC 7421 sequences.

BIL domain nomenclature: BIL domains were named using the format "a_b" where "b" is an abbreviation of the bacterial species of origin and where "a" is either host protein name (e.g., "FhaB" or "MafB"); an arbitrary BIL# designation; an Integratedgenomics Database (http://ergo.integratedgenomics.com/R_capsulatus.html) number for *R. capsulatus*; a Computational Biology Program at ORNL (http://genome.ornl.gov/microbial/rsph) analysis code for *R. sphaeroides*; or a gene number for *B. melitensis* strain 16M and *N. meningitidis* strains MC58 and Z2491. Available gene identifier accession numbers and further information relevant to identified BIL domains are provided in Table 1, below.

Computational sequence analysis: The BLAST software package of the NCBI was used for sequence-to-sequence searches (Altschul, S F. et al., 1997. Nucleic Acids Res. 25, 3389) of BIL domains with BIL domains and with intein sequences, and the BLIMPS software was employed for block-to-sequence searches (Henikoff S. et al., 1995. Gene 163, GC17). Multiple block sequence alignments were constructed using BLOCKMAKER (Henikoff S. et al., 1995. Gene 163, GC17) and MACAW (Schuler G D. et al., 1991. Structure, Function and Genetics 9, 180) software, as previously described (Pietrokovski S., 1998. Protein Science 7, 64). BIL domains were aligned with other BIL domains having higher scores than with intein sequences and alignments of BIL domains with each other was across their whole, or almost whole, lengths (results not shown). This is also a practical way to classify BIL domains as such. Phylogenetic analysis was performed using the PHYLIP software package (Felsenstein J., 1989. Cladistics 5, 164) version 3.55.

Generation of BIL domain phylogeny dendrograms: BIL domain phylogeny dendrograms were computed from DNA multiple sequence alignment of 49 mostly complete BIL domains aligned across 201 positions, coding for 67 amino acids which could be confidently aligned across BIL domains. Nodes with bootstrap values below 440/1000 were collapsed, and bootstrap values above 800/1000 are shown. Bootstrap values of the nodes grouping all A-type and B-type BILs are 441 and 519, respectively. The *D. melanogaster* Hedgehog Hint domain (Porter J A., et al., 1996. Cell 86, 21) was used as an outgroup to root the tree. The dendrogram was calculated using the DNADIST program (version 3.5) of the PHYLIP software package (Felsenstein J., 1989. Cladistics 5, 164). Results were verified against those obtained using CLUSTALW software (Thompson J D. et al., 1994. Nucl Acid Res. 22, 4673) and from protein multiple sequence alignments obtained using PHYLIP, PROTDIST, and CLUSTALW software.

BIL Functional Activity Assays:

In order to analyze the capacity of BIL domains to auto-cleave/auto-splice flanking sequences, genetic sequences encoding BIL domains and portions of flanking sequences were cloned for expression as chimeric proteins tagged at their amino terminal ends with the malE gene-encoded maltose-binding protein (MBP) affinity tag, and at the carboxy terminal end with the *B. circulans* cbd gene-encoded chitin-binding domain (CBD) affinity tag. These chimeras were expressed in an in-vitro transcription/translation system, or overexpressed in-vivo in *E. coli*, and resulting protein products were analyzed for evidence of BIL domain-mediated autoprocessing activity.

Such chimeras were cloned using BIL domain genetic sequences encoding:

(i) the Type A BIL domain FhaB_psesy (Table 1, FIG. 1a) and its downstream-flanking threonine residue to generate the chimera "MBP-PsyBIL-CBD"; and (ii) the Type B BIL domain BIL2_rhosp (Table 1, FIG. 1b) including 32 amino terminal-flanking and 11 carboxy terminal-flanking amino acids to generate the chimera "MBP-RspBIL2-CBD".

Constructs: *B. circulans* cbd gene sequences encoding CBD were cloned by PCR from expression vector pTYB2 (New England Biolabs, Beverly, Mass.) using the primers 5'-AAATGTCGACTGCGGTGGCCTGACC-3' (SEQ ID NO: 1) and 5'-TGTCGTATTGCTTCCTTTCGGGCTT-3' (SEQ ID NO: 2), and inserted, including the upstream linker 5'-TGCGGTGGCCTGACCGGTCTGAACTCAGGCCTC-3' (SEQ ID NO: 3), into the SalI/PstI linearized, isopropyl beta-D-thiogalactoside (IPTG)-inducible MBP-fusion protein expression construct pMALC2 to generate the MBP-CBD fusion protein expression construct pC2C. Construct pC2C was used in functional assays as a positive control for expression of MBP-CBD.

For MBP-PsyBIL-CBD expression, genetic sequences encoding PsyBIL and flanking sequences were PCR amplified from *P. syringae* DC3000 strain genomic DNA (kindly provided by Dr. G. Sessa, Tel-Aviv University) using the primers 5'-AAAAGGATCCTGCTTTGCGGCCG-GAACGA-3' (SEQ ID NO: 4) and 5'-AAAATCTAGAGG-TATTATGCACCCATGTCTTG-3' (SEQ ID NO: 5), and cloned in BamHI/XbaI linearized pC2C, between the malE MBP-encoding sequences and the CBD expressing cbd sequences to generate the MBP-PsyBIL-CBD expression construct pC2C-PsyBIL.

For MBP-RspBIL2-CBD expression, genetic sequences encoding RspBIL2 and flanking sequences were PCR-amplified from *R. sphaeroides* 2.4.1 strain genomic DNA (supplied by Dr. Steven L. Porter, Department of Biochemistry, University of Oxford) using the primers 5'-GAATTCGGTGAT-TCATCCTTGGGGCGA-3' (SEQ ID NO: 6) and 5'-TCTA-GAAAAACACGGCAAGGGCGAGCGG-3' (SEQ ID NO: 7), and cloned in EcoRI/XbaI linearized pC2C, between the MBP-encoding malE sequences and the CBD-encoding cbd sequences to generate the MBP-RspBIL2-CBD expression construct pC2C-RspBIL2.

The MBP-BIL4Cloth-CBD Expression Construct pC2C-BIL4Cloth.

Polymerase chain reactions were performed using a Biometra thermal cycler in a 50 µl reaction mixture containing Taq polymerase buffer (Sigma, St. Louis, Mich.), 1 µl Taq DNA polymerase, 200 mM dNTP, 10 mM of each primer and 100 ng genomic DNA The chimeras were constructed such that carboxy terminal or amino terminal cleavage thereof was expected to generate [MBP-BIL+CBD] or [MBP+BIL-CBD] specific protein products, respectively. The MBP- or CBD-containing protein products were expected to vary in size according to the size of the BIL domain flanking sequences included in the BIL sequences cloned in the chimeric proteins. Auto-splicing by the chimeras was expected to generate MBP-CBD protein products having a molecular weight varying according to the size of the BIL domain flanking sequences included in the cloned BIL segment.

Chimeras were expressed and analyzed for evidence of BIL processing activity, as described below.

In-vitro BIL protein expression and activity assays: In-vitro transcription-translation of MBP-BIL-CBD and MBP-CBD chimeric proteins was achieved using chimera expression constructs pC2C-RspBIL2 and pC2C-RspBIL2a, and expression construct pC2C as DNA templates, respectively, using E. coli S30 extract for circular DNA system (Promega Kit #L1030, Promega, Madison Wis.). Reactions were carried out according to the manufacturer's instructions, using a reaction containing 0.25 mM [$^{35}$S]-methionine, 220 nmol of expression construct DNA as template, 1-2 mM dithiothreitol, and having a pH of about 8.0. Reactions were incubated at 37° C. for 90-120 minutes. Prior to electrophoresis of expressed protein, 5 µl or 10 µl aliquots of reaction mixtures were mixed with four volumes of acetone in order to remove polyethylene glycol. Acetone precipitation was followed by centrifugation at 12,000×g for 5 minutes. The supernatant was discarded and the protein-containing pellet was mixed with gel loading buffer to give a final concentration of 0.06 M Tris-Cl, 2% SDS, 10% (v/v) glycerol, and 0.01% bromophenol blue. Proteins were separated via 7.5% or 10% SDS-PAGE, and the separated proteins were visualized using a phosphor-imaging screen. Phosphor-imaging signals were quantified using NIH IMAGE 1.62 software. Product quantities were derived from values of three independent experiments averaged for each sample together with their standard deviation of the means. The molar percentage of each product was calculated.

The expected molecular weights of MBP-RspBIL2-CBD, and of its splicing product MBP-CBD, its carboxy terminal cleavage product MBP-RspBIL2, and its MBP-containing amino terminal cleavage product are 68.0, 55.1, 60.5 and 46.7 kDa, respectively.

The expected molecular weights of control vector pC2C-expressed MBP-CBD and of its MBP portion were 50.3 and 43.0 kDa, respectively.

In-vivo Type A BIL domain protein expression, purification and activity assay: Competent TB1 E. coli cells (NEB, Beverly, Mass.) were transformed with constructs for expression of MBP-BIL-CBD chimeras. Transformants were plated on LB agar supplemented with ampicillin (100 µg/ml). Single colonies were used to inoculate 3 ml aliquots of LB medium supplemented with ampicillin (100 µg/ml). Following incubation at 37° C. for 16 hours with shaking, 1 ml of culture was used to inoculate a 2 liter flask containing 500 ml of LB supplemented with ampicillin (100 µg/ml). Incubation was continued at 37° C. with shaking until the optical density at 600 nm was 0.6, at which point IPTG was added to a final concentration of 0.3 mM. After further incubation for 3 hours, cells were harvested by centrifugation at 5,000×g for 20 minutes, re-suspended in solution containing 20 mM Tris (pH 7.4), 200 mM NaCl, and protease inhibitor cocktail (Sigma, St. Louis, Mich.), and lysed by sonication. Lysates were centrifuged at 17,000×g for 20 minutes to remove cell debris, and supernatants were harvested for subsequent analyses. Proteins were then affinity purified with either chitin (NEB, Beverly, Mass.) or amylose beads (NEB, Beverly, Mass.) which bind to the CBD or MBP affinity tags included in the chimeric protein. Elution of protein from beads prior to electrophoresis was performed by mixing the protein-bound beads with SDS-PAGE sample loading buffer.

Western immunoblotting assays and protein staining: Products generated by expression of MBP-BIL-CBD chimeras were separated by SDS-PAGE. Briefly, protein samples were mixed with protein loading buffer to give a final concentration of 0.06 M Tris-Cl, 2% SDS, 10% (v/v) glycerol, 0.1 M dithiothreitol, and 0.01% bromophenol blue. All samples were boiled for 3 minutes prior to electrophoresis. Separated proteins were analyzed by Western immunoblotting using either monoclonal mouse anti-MBP (Novus Biologicals, Inc. Littleton, Colo.) antibody for identification of the MBP tag, or polyclonal rabbit anti-CBD (NEB, Beverly, Mass.) for identification of the CBD tag. Secondary antibodies used were HRP conjugated goat anti-mouse IgG or goat anti-rabbit IgG (Jackson ImmunoResearch Laboratories Inc., West Grove, Pa.). Relative apparent molecular weights were calculated using TriChromoRanger (Pierce, Rockford Ill.) prestained markers.

Electrophoretic gels containing separated proteins were fixed in 40% methanol/7% acetic acid and stained with Phast-Gel Blue R stain (Pharmacia Biotech AB, Sweden). Gels were destained in 40% methanol/7% acetic acid and then in deionized water, and visualized protein bands were excised and electroeluted for MALDI mass spectroscopy (MS) analysis.

Electroelution of protein: Protein was electroeluted from gels at 150 volts for 2 hours in GeBAflex tubes (Gene Bio Application Ltd., Israel) using elution buffer containing 0.025% SDS, Tris and Tricine (pH 8.5). Following electroelution SDS was removed from electroeluted protein using cold TCA:acetone precipitation in the presence of 0.5% sodium deoxycholate (NaDOC; T. Mehlman and A. Shainskaya, unpublished).

In-gel proteolysis: Protein bands from PhastGel Blue R stained gels were destained using multiple washes in 50% acetonitrile in 50 mM ammonium bicarbonate. Destained protein bands were subsequently reduced, alkylated and in-gel proteolysed using either bovine trypsin (sequencing grade, Roche Diagnostics, Germany) or chymotrypsin, (Boehringer Mannheim, Germany) by incubation with 12.5 ng/µl protease in 50 mM ammonium bicarbonate at 37° C., as previously described (Shevchenko et al., 1996. Analytical Chemistry 68, 850). Extracted peptide solutions were dried for subsequent MALDI-MS analysis.

Mass Spectrometry: Intact molecular mass measurement and peptide mass mapping were performed using a Bruker Reflex III MALDI time-of-flight (TOF) mass spectrometer (Bruker, Bremen, Germany) equipped with SCOUT source, delayed ion extraction, reflector and a 337 nm nitrogen laser. Each mass spectrum was generated using data accumulated from 200 laser shots. Both external and nearby calibrations for proteins were performed using BSA and myoglobin (Sigma). For peptide mapping, internal calibration with molecular ions of regularly occurring matrix ions and peptides derived from trypsin was additionally performed to consolidate further peptide assignment.

Intact molecular weight measurements by MALDI MS: Gel electroeluted proteins were further purified by cold acetone precipitation. The dried extract from one lane of the gel was re-dissolved in 0.5 ml of 80% formic acid and immediately diluted with water to yield a solution containing 20% formic acid, and 50% of this solution was applied to a target plate.

Peptide mass mapping by MALDI mass spectrometry: Aliquots of one tenth of the extracted peptide mixture volume, dissolved in 0.1% TFA or formic acid/isopropanol/water (1:3:2), were used for MALDI-MS using the fast evaporation or dry droplet method. Matrix surfaces of α-cyano-4-hydroxycinnamic acid (4-HCCA) or 2,5-dihydroxybenzoic acid (DHB) were utilized for the fast evaporation (Jensen O N. et al., 1996. Rapid Commun in Mass Spectrom. 10, 1371; Vorm O. et al., 1994. Analyt Chem. 66, 3281) or dry droplet method (Kussmann K. et al., 1997. J Mass Spectrom. 32, 593), respectively.

Experimental Results:

Identification of two novel bacterial intein-like domains containing Hint-like motifs: Searches of sequence databases of diverse bacterial species for Hint-like motif-containing putative ORFs identified open reading frames coding for proteins comprising two related types of novel intein-like protein domains termed by the present inventors Type A and Type B bacterial intein-like (BIL) domains. Novel type A and B BIL domain sequences identified are shown aligned in FIGS. 1a (SEQ ID NOs: 8-62) and 1b (SEQ ID NOs: 63-104), respectively. The bioinformatic sources used to identify these BIL domains are shown in Table 1.

An amino acid sequence motif (SEQ ID NO: 105) was identified (FIG. 2a) which exclusively defines a subset of Type A BIL domains, including domains: 39_9_thefus, SCP1.201_strco, 3875_87_magma, B0372+_neimeB, B0655+_neimeB, A2115_neime, MafB1_neimeC, BIL2_neimeC, BIL4_neimeC, BIL5_neimeC, BIL6_neimeC, MafB1_neigo, BIL2_neigo, BIL3_neigo, MafB2_neigo, BIL5_neigo, BIL6_neigo, FhaB_psesy, FhaB_manha, FhaB1_psefl-PfO-1, FhaB1_-psefl-SBW25, BIL6_cloth, BIL5_cloth, BIL2_cloth, BIL4_cloth, BIL1_cloth, BIL8_cloth, BIL9_cloth, BIL1_gemob, BIL2_gemob, 0709_lepin, 3725_lepin, o1078_myxxa, o1070_myxxa, BIL1_strav, BIL2_strav, BIL3_strav, BIL1_pirsp, BIL1_chrvi, o3395_versp, o5687_versp, o649_versp, BIL1_glovi, BIL2_glovi, BIL3_glovi, and BIL4_glovi.

An amino acid sequence motif (SEQ ID NO: 106) was identified (FIG. 2b) which exclusively defines a subset of Type. B BIL domains, including: 4825_rhosp, BIL2_rhosp, 00588_rhoca, 02710_rhoca, 01524_rhoca, 01523_rhoca, 00126_rhoca, 01216_rhoca, 00949_rhoca, 01374_rhoca, 00459_rhoca, 00460_rhoca, 00746_rhoca, 03530_rhoca, 00199_rhoca, BIL3_magma, BIL4_magma, BIL1_brusu, BIL1_unknwn, BIL2_unknwn, 06786_metex, BIL1_silpo, BIL2_silpo, BIL3_silpo, BIL4_silpo, BIL5_silpo, BIL6_silpo, BIL7_silpo, BIL8_silpo, BIL9_silpo, BIL10_silpo, BIL11_silpo, BIL12_silpo, BIL13_silpo, BIL14_silpo, BIL15_silpo, BIL16_silpo, BIL1_rhile, and II0519_brume.

This new type of domain appears in non-conserved regions of hyper-variable proteins. Thus, these domains are distinct from the Hint domains of inteins and Hog-proteins by the species and proteins in which they appear. An analysis of amino acid residue conservation within Hint-like motifs of BIL domains and within homologous Hint domain motifs of Hog proteins and inteins is shown in (FIGS. 3a-z). Examination of BLAST sequence alignments (Altschul, S F. et al., 1997. Nucleic Acids Result. 25, 3389) of BIL domains with BIL domains and with intein sequences showed that BIL domains aligned with each other with higher scores than with intein sequences across their whole, or almost whole, lengths (results not shown). Therefore, BIL domains were found to be distinct from inteins by their global sequence features.

TABLE 1

Databases used to identify BIL domains.

| BIL Type | BIL domain name* | Source** | Date*** | Contig/Entry | Coordinates |
|---|---|---|---|---|---|
| A | BIL1_cloth | NCBI | | 23022619 | — |
| A | BIL2_cloth | NCBI | | 28N'aa + 23020813 + 59aa + 23020812 | — |
| A | BIL3_cloth | NCBI | | 23022239 + 14N'aa | — |
| A | BIL4_cloth | NCBI | | 23020817 + 5N'amino acid/gi\|23020817 | 311-445 |
| A | BIL5_cloth | NCBI | | 23020815 + 13N'aa | — |
| A | BIL6_cloth | NCBI | | 23022237 | — |
| A | BIL7_cloth | NCBI | | 23022587 + 7N'aa | — |
| A | BIL9_cloth | NCBI | | 23022893 + 59aa + 23022892 | — |
| A | BIL10_cloth | NCBI | | 22262017 | 34594-34986 |
| A | BIL11_cloth | NCBI | | 22262176 | 416-728 |
| A | 3875_87_magma | NCBI | | 21614488 | 76532-75165 |
| A | FhaB_manha | BCM | 4 Oct. 2001 | C78-C85 | 11046-20977 |
| A | BIL2_neigo | OU-ACGT | 26 Sep. 2000 | AE004969 | 1563413-1564129 |
| A | BIL3_neigo | OU-ACGT | 26 Sep. 2000 | AE004969 | 1565033-1565809 |
| A | BIL5_neigo | OU-ACGT | 26 Sep. 2000 | AE004969 | 1351509-1350766 |
| A | BIL6_neigo | OU-ACGT | 26 Sep. 2000 | AE004969 | 1349978-1349310 |
| A | MafB1_neigo | OU-ACGT | 26 Sep. 2000 | AE004969 | 1560214-1561941 |
| A | MafB2_neigo | OU-ACGT | 26 Sep. 2000 | AE004969 | 1355876-1354062 |
| A | B0369+_neimeB | NCBI | | 7225591 + 34 N' aa | — |
| A | B0372+_neimeB | NCBI | | 7225594 + 11 N' aa | — |
| A | B0655+_neimeB | NCBI | | 7225882 + 14 N' aa | — |
| A | BIL2_neimeC | Sanger | 15 May 2002 | NmC | 1836857-1837573 |
| A | BIL3_neimeC | Sanger | 15 May 2002 | NmC | 1838418-1838981 |
| A | BIL4_neimeC | Sanger | 15 May 2002 | NmC | 1839771-1840439 |
| A | BIL5_neimeC | Sanger | 15 May 2002 | NmC | 627204-627920 |

TABLE 1-continued

Databases used to identify BIL domains.

| BIL Type | BIL domain name* | Source** | Date*** | Contig/Entry | Coordinates |
|---|---|---|---|---|---|
| A | BIL6_neimeC | Sanger | 15 May 2002 | NmC | 628395-629102 |
| A | MafB1_neimeC | Sanger | 15 May 2002 | NmC | 1833717-1835480 |
| A | FhaB1_psefl-PfO-1 | NCBI-TIGR | | 205922-575 | 3-6313 |
| A | FhaB1_psefl-SBW25 | Sanger | 2 Sep. 2002 | Pflu552a01 | 41728-29387 |
| A | FhaB_psesy | TIGR | 30 Aug. 2002 | 5668 | 5148986-5149429 |
| A | SCP1.201_strco | NCBI | | 13620683 + 32 N' aa | |
| A | 39_9_thefus | JGI | 1 Nov 2000 | 39 | 13655-15508 |
| A | BIL1_gemob | TIGR | 23 Sep. 2002 | 14 | 32-20392 |
| A | BIL2_gemob | TIGR | 14 Feb. 2003 | 354 | 16692-11734 |
| A | 0709_lepin | NCBI | 10 Nov. 2002 | 24213409 | — |
| A | 3725_lepin | NCBI | 10 Nov. 2002 | 24216424 | — |
| A | 3719_lepin | NCBI | 10 Nov. 2002 | 24197710 | — |
| A | o665_myxxa | TIGR | 23 Apr. 2003 | 168 | 495-3704 |
| A | o1078_myxxa | TIGR | 23 Apr. 2003 | 157 | 103477-106710 |
| A | o1070_myxxa | TIGR | 23 Apr. 2003 | 168 | 495-3704 |
| A | BIL1_strav | NCBI | 20 Jul. 2003 | 29826740 | — |
| A | BIL2_strav | NCBI | 20 Jul. 2003 | 29826826 | — |
| A | BIL3_strav | NCBI | 20 Jul. 2003 | 29831835 | — |
| A | BIL1_pirsp | NCBI | 20 Jul. 2003 | 32470666 | — |
| A | BIL1_chrvi | NCBI | 07 Sep. 2003 | 34104178 | — |
| A | BIL1_glovi | Kazusa | 04 Sep. 2003 | gll0211 | — |
| A | BIL2_glovi | Kazusa | 04 Sep. 2003 | gll0207 | — |
| A | BIL3_glovi | Kazusa | 04 Sep. 2003 | gll0213 | — |
| A | BIL4_glovi | Kazusa | 04 Sep. 2003 | gll0212 | — |
| A | BIL5_glovi | Kazusa | 04 Sep. 2003 | gll0205 | — |
| A | BIL6_glovi | Kazusa | 04 Sep. 2003 | gll0208 | — |
| A | BIL7_glovi | Kazusa | 04 Sep. 2003 | gsl3615 | — |
| A | o649_versp | TIGR | 02 Sep. 2003 | 65738 | 3-1949 |
| A | o5687_versp | TIGR | 02 Sep. 2003 | 65921 | 18348-1288 |
| A | o3395_versp | TIGR | 02 Sep. 2003 | 65925 | 56853-46669 |
| B | II0519_brume¶ | NCBI | | 17988864 | |
| B | BIL2_magma | NCBI | | 21613062 | 922-1590 |
| B | BIL3_magma | NCBI | | 21614112 | 2449-1475 |
| B | BIL4_magma | NCBI | | 21614173 | 2216-3187 |
| B | BIL5_magma | NCBI | | 21612572 | 3-338 |
| B | BIL6_magma | NCBI | | 21613847 | 2033-1774 |
| B | 06786_metex | IG | June 2002 | 1507 | 6076-7113 |
| B | 00126_rhoca | IG | December 2001 | 2G06-2D11 | 114767-113670 |
| B | 00199_rhoca | IG | December 2001 | 2G06-2D11 | 178648-177806 |
| B | 00459_rhoca | IG | December 2001 | 2G06-2D11 | 434469-435083 |
| B | 00460_rhoca | IG | December 2001 | 2G06-2D11 | 435094-436191 |
| B | 00746_rhoca | IG | December 2001 | 2D10-2D06 | 2243-3079 |
| B | 00949_rhoca | IG | December 2001 | 2A12-2D05 | 325707-326651 |
| B | 01216_rhoca | IG | December 2001 | 2A12-2D05 | 222590-223555 |
| B | 01374_rhoca | IG | December 2001 | 2A12-2D05 | 148470-149462 |
| B | 01523_rhoca | IG | December 2001 | 1A01-1C09 | 279638-280444 |
| B | 01524_rhoca | IG | December 2001 | 1A01-1C09 | 280569-281423 |
| B | 02710_rhoca | IG | December 2001 | 1D09-1F02 | 197288-199588 |
| B | 03530_rhoca | IG | December 2001 | 1A01-1C09 | 521700-521173 |
| B | 4825_rhosp | JGI | 26 Mar. 2001 | 184 | 67785-67165 |
| B | BIL2_rhosp | JGI | 26 Mar. 2001 | 177 | 9673-10194 |
| B | BIL1_silpo | TIGR | 18 Jun. 2002 | 50 | 10679-14440 |
| B | BIL2_silpo | TIGR | 18 Jun. 2002 | 50 | 1-2688 |
| B | BIL3_silpo | TIGR | 18 Jun. 2002 | 4 | 10260-12356 |
| B | BIL4_silpo | TIGR | 18 Jun. 2002 | 290 | 18579-19640 |
| B | BIL5_silpo | TIGR | 18 Jun. 2002 | 11 | 3224-2217 |
| B | BIL6_silpo | TIGR | 18 Jun. 2002 | 199 | 13687-15303 |
| B | BIL7_silpo | TIGR | 18 Jun. 2002 | 199 | 15104-16399 |
| B | BIL8_silpo | TIGR | 18 Jun. 2002 | 32 | 1329-2600 |
| B | BIL9_silpo | TIGR | 18 Jun. 2002 | 32 | 28672-26588 |
| B | BIL10_silpo | TIGR | 18 Jun. 2002 | 60 | 19338-18265 |
| B | BIL11_silpo | TIGR | 18 Jun. 2002 | 89 | 10027-11181 |
| B | BIL12_silpo | TIGR | 18 Jun. 2002 | 126 | 9020-10066 |
| B | BIL13_silpo | TIGR | 18 Jun. 2002 | 110 | 13640-14440 |
| B | BIL14_silpo | TIGR | 18 Jun. 2002 | 125 | 9769-10353 |
| B | BIL15_silpo | TIGR | 18 Jun. 2002 | 129 | 7727-8257 |
| B | BIL16_silpo | TIGR | 18 Jun. 2002 | 195 | 7271-8050 |
| B | Bil1_rhile | Sanger | 14 Jul. 2003 | RHIZ10E3Cb12.slk | — |

TABLE 1-continued

Databases used to identify BIL domains.

| BIL Type | BIL domain name* | Source** | Date*** | Contig/Entry | Coordinates |
|---|---|---|---|---|---|
| B | BIL1_unknwn | TIGR | 13 Mar. 2001 | 14712 | 1124-51 |
| B | BIL2_unknwn | TIGR | 13 Mar. 2001 | 12703 | 2-1369 |

*the bacterial species origin of the BIL domains is identified by the bacterial species code following the underscore in the BIL name (refer to Table 2 below for the code-species correspondance).
**The sources are named as follows JGI—Joint Genome Institute (http://www.jgi.doe.gov), NCBI—(http://www.ncbi.nlm.nih.gov), Sanger—The Sanger Institute (http://www.sanger.ac.uk), OU-ACGT—University of Oklahoma, Advanced Center for Genome Technology (http://www.genome.ou.edu), TIGR—The Institute for Genomic Research (http://www.tigr.org), BCM—Baylor College of Medicine Human Genome Sequencing Center (http://www.hgsc.bcm.tmc.edu), IG—IntegratedGenomics (http://www.integratedgenomics.com), and Kazusa—Kazusa DNA Research Institute database (Japan; http://www.kazusa.or.jp).
***Dates refer to the data release dates used. The NCBI entries were extended as noted. Coordinates of the BIL host protein ORF are given for nucleotide contigs/entries. The positions of BILs within these ORFs are provided in Figures 1a-b.
¶An identical sequence was identified in *Brucella suis*

Conserved motifs in BIL domains, Hog proteins and inteins: Alignments of conserved motifs in Type A BIL domains, Type B BIL domains, Hog proteins, and inteins are shown in FIGS. 3a-g, 3h-o, 3p-t, and 3u-z, respectively. Type A BIL domains were found to share 7 Hint-like consensus sequence motifs (FIGS. 3a-d and 3f-g) and one novel motif (FIG. 3e) having no known Hog or intein counterpart.

Almost all Type A BIL domains were found to comprise apparent functional protein splicing active sites corresponding to those present in inteins (marked by asterisks in FIGS. 3u, 3w and 3z), and several are also flanked at their carboxy terminal ends with serine or threonine amino acid residues, similarly to the carboxy terminal ends of inteins.

Type A BIL domains were found to contain an invariant His-Asn amino acid residue pair adjacent to the carboxy terminal end thereof (FIG. 3g), similarly to the His-Asn amino acid residue pair typically forming the carboxy terminal ends of inteins (FIG. 3z, positions 7-8). Conservation of the Type A BIL domain carboxy terminal end with that of inteins suggests that, similarly to inteins, Type A BILs undergo cyclization of the Asn residue forming the carboxy terminal end thereof. However, the residue at the carboxy terminal end of Type A BIL domains (FIG. 3g, position 8), which corresponds to the residue forming the amino terminal end of polypeptide segments flanking the carboxy terminal ends of inteins which is always Cys, Ser or Thr (FIG. 3z, position 9), is not conserved, since only a few Type A BIL domains have a serine or threonine residue in that position. Other Type A BIL domains have aspartate, glutamate, asparagine, tyrosine or alanine residues in that position, which are not found in any intein.

Type B BIL domains were also found to share 6 Hint-like consensus sequence motifs (FIGS. 3h-i and 3l-o) and two novel motifs (FIGS. 3j-k) having no known Hog protein or intein Hint domain counterpart. Type B BIL domain carboxy terminal ends were found to have a conserved position comprising Cys, Ser or Thr residues (FIG. 3o, position 6), potentially corresponding to the carboxy terminal flanking position of inteins (FIG. 3z, position 9), however this carboxy terminal residue of Type B BIL domains (FIG. 3o, position 7) is not preceded by the His-Asn motif typically found in inteins (FIG. 3z, positions 7-8) and in Type A BIL domains (FIG. 3g, positions 6-7). The —SH/—OH groups on the side chains of the aforementioned Cys, Ser or Thr residues in intein host proteins have been found to be essential for ligation of the intein carboxy and amino flanks in the protein splicing reaction (Xu M Q. and Perler F B., 1996. EMBO J. 15, 5146).

In Type A BIL domains whose carboxy terminal ends are not flanked by Thr or Ser residues, Asn cyclization may nevertheless occur without trans-esterification by the flanking residue. Alternately, trans-esterification may occur by the mildly nucleophilic residues found in this position. In the first case the BIL domain would be cleaved from a segment flanking its carboxy terminal end, and in the second case protein splicing would occur. Since Type B BIL domains do not have any conserved Asn or Gln residue at their carboxy terminal end, cleavage of this end could then proceed by a mechanism different from the Asn and Gln cyclizations of inteins (Paulus H., 2000. Annu Rev Biochem. 69, 447).

Key amino acid residues corresponding to protein splicing active sites (marked by asterisks in FIGS. 3u, 3w, and 3z-position 9) were found to be conserved in Type B BIL domains.

Both Type A and Type B BIL domains were found to be distinct from inteins in having additional unique sequence motifs, in not being integrated in highly conserved sites of essential proteins, and in not comprising endonuclease domains.

Phylogenetic distribution of BIL domains: The phylogenetic distribution of the BIL domains identified is shown in Table 2. BIL domains were identified in 3 evolutionarily distant bacterial types—alpha, beta and gamma proteobacteria (gram-negative bacteria), actinobacteria (high GC gram-positive bacteria), and *Bacillus/Clostridium* group bacteria (low GC gram-positive bacteria).

Both presence and genomic distribution were found to be variable, even in closely related species and strains. For example, 1, 3 and 6 ORFs encoding BIL domains were identified, respectively, in *N. meningitidis* strains whose genomes have been completely or almost completely sequenced; 2 and 14 ORFs encoding BIL domains were identified in 2 different *Rhodobacter* species; and while one such ORF was identified in *P. syringae*, none were found in *P. aeruginosa* and *P. putida*.

BIL domains and inteins were found to coexist in certain species. For example, the genome of *M. magnetotacticum* was found to comprise ORFs encoding both Type A and Type B BIL domains, and that of *T. fusca* was found to comprise ORFs encoding both BIL domains and inteins.

Figure 4B:
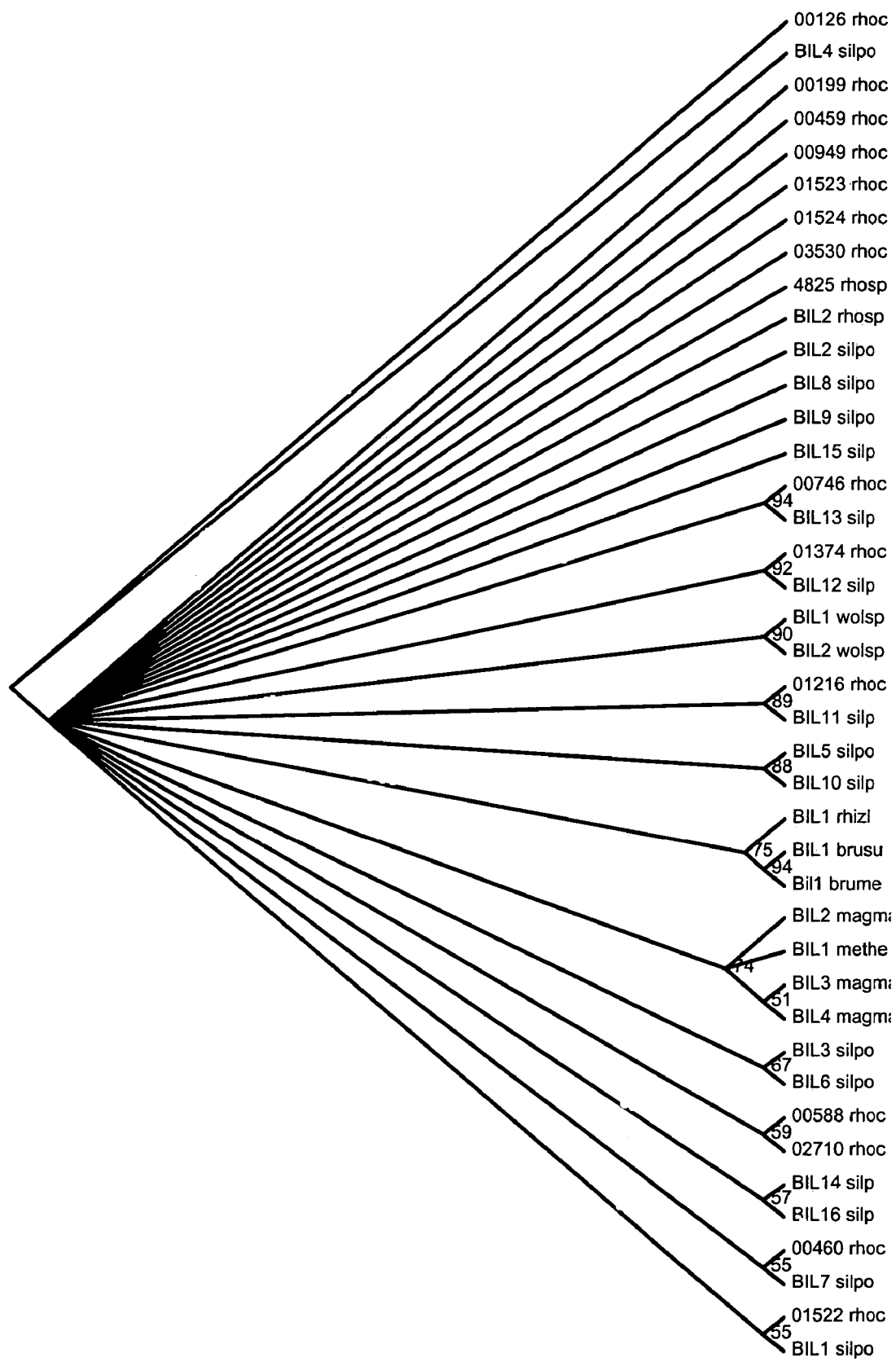

The variability observed in the number of BIL domain ORFs in different species is probably due to gene duplications. As shown in a dendrogram demonstrating phylogenetic relationships of Type A BIL domains (FIG. 4a), all BIL domains derived from *Neisseria* species cluster together, and BIL domains from different species sub-cluster as well, implying that all *Neisseria* BIL domains arose by duplication from a single ancestor and that some are paralogs within different species. The latter is corroborated by the apparent duplication of some gene loci containing BIL domains in these species (not shown). Clustering of BIL domains from the same species was also observed in *C. thermocellum* (FIG. 4a) and *M. Magnetotacticum* (FIG. 4b).

BIL domain host proteins: BIL domains were identified in putative ORFs coding for a few hundred to a few thousand amino acids. Several BIL domains were found to be flanked by domains present in secreted bacterial proteins. In *P. syringae* and *M. haemolytica*, BIL domains were identified near the carboxy terminal end of FhaB-like ORFs. FhaB is a very large *Bordetella* gene coding for a secreted filamentous hemagglutinin protein, which functions as an adhesin important for *B. pertussis* virulence (Smith A M. et al., 2001. FEMS Microbiol Rev. 25, 309). Three of the *R. capsulatus* BIL domain-containing ORFs include RTX repeats—calcium binding repeats found in various secreted bacterial proteins, including many toxins (Coote J G., 1992. FEMS Microbiol Rev. 8, 137). In *N. meningitidis* and *N. gonorrhoeae*, BIL domains were identified in MafB proteins. These are part of multiple adhesin family possibly involved in glycolipid adhesion to cells (Naumann et al., 1999. Curr Opin Microbiol 2, 62-70; Paruchuri et al., 1990. Proc Natl Acad Sci U S A. 87, 333-7). Three other *Neisseria* BIL domains were found to have an HNH nuclease domain in amino acid sequences flanking their carboxy terminal ends. HNH domains are found in various DNase and endonuclease proteins including secreted toxins (Belfort M. and Roberts R J., 1997. Nucleic Acids Res. 25, 3379; James R. et al., 1996. Microbiology 142, 1569). A domain present in the amino acid sequence flanking the carboxy terminal end of a BIL domain in the gram-positive bacterium *T. fusca* is also found in a short, conserved *Salmonella* ORF (GenBank accession NP_454902) and in an amino acid sequence flanking the carboxy terminal end of a *N. meningitidis* FhaB/hemolysin protein (gene NMA0688). Both of these proteins are from gram-negative bacteria and are likely to be secreted.

TABLE 2

Phylogenetic distribution of BIL domains identified.

| Taxonomic group | Species | Species code | BIL type | No. of BIL domains identified in organism |
|---|---|---|---|---|
| alpha proteobacteria | *Rhodobacter capsulatus* SB1003 | rhoca | B | 14* |
| alpha proteobacteria | *Rhodobacter sphaeroides* 2.4.1 | rhosp | B | 2* |
| alpha proteobacteria | *Silicibacter pomeroyi* DSS-3 | silpo | B | 16* |
| alpha proteobacteria | *Brucella melitensis* 16M/*Brucella suis* | brume | B | 1 |
| alpha proteobacteria | *Magnetospirillum magnetotacticum* MS-1 | magma | A | 1 |
| alpha proteobacteria | | | B | 5* |
| alpha proteobacteria | *Methylobacterium extorquens* AM1 | metex | B | 1* |
| alpha proteobacteria | *Rhizobium leguminosarum* bv. *viciae* 3841 | rhile | B | 1 |
| beta proteobacteria | *Neisseria meningitidis* Z2491 | neimeA | A | 1 |
| beta proteobacteria | *Neisseria meningitidis* MC58 | neimeB | A | 3 |
| beta proteobacteria | *Neisseria meningitidis* FAM18 | neimeC | A | 6* |
| beta proteobacteria | *Neisseria gonorrhoeae* FA1090 | neigo | A | 6 |
| beta proteobacteria | *Chromobacterium violaceum* ATCC 12472 | chrvi | A | 1 |
| gamma proteobacteria | *Pseudomonas syringae* DC3000 | psesy | A | 1* |
| gamma proteobacteria | *Pseudomonas fluorescens* PfO-1 | psefl-PfO-1 | A | 1* |
| gamma proteobacteria | *Pseudomonas fluorescens* PfSBW25 | psefl-SBW25 | A | 1* |
| gamma proteobacteria | *Mannheimia haemolytica* PHL213 | manha | A | 1* |
| delta proteobacteria | *Myxococcus xanthus* DK1622 | myxxa | A | 3* |
| spirochaetes | *Leptospira interrogans* 56601 | lepin | A | 3 |
| actinobacteria | *Streptomyces coelicolor* A3(2) | strco | A | 1 |
| actinobacteria | *Streptomyces avermitilis* MA-468 | strav | A | 3 |
| actinobacteria | *Thermobifida fusca* YX | thefu | A | 1* |
| Bacillus/Clostridium group | *Clostridium thermocellum* ATCC 27405 | cloth | A | 10* |
| planctomycetes | *Pirellula* species 1 | pirsp | A | 1 |
| planctomycetes | *Gemmata obscuriglobus* UQM 2246 | gemob | A | 2* |
| cyanobacteria | *Gloeobacter violaceus* PCC 7421 | glovi | A | 7 |
| verrucomicrobium | *Verrucomicrobium spinosum* DSM 4136 | versp | A | 3* |
| unknown | Unknown | | B | 2* |

*Genome not fully sequenced - total number of BILs may be greater.

Figure 5A:
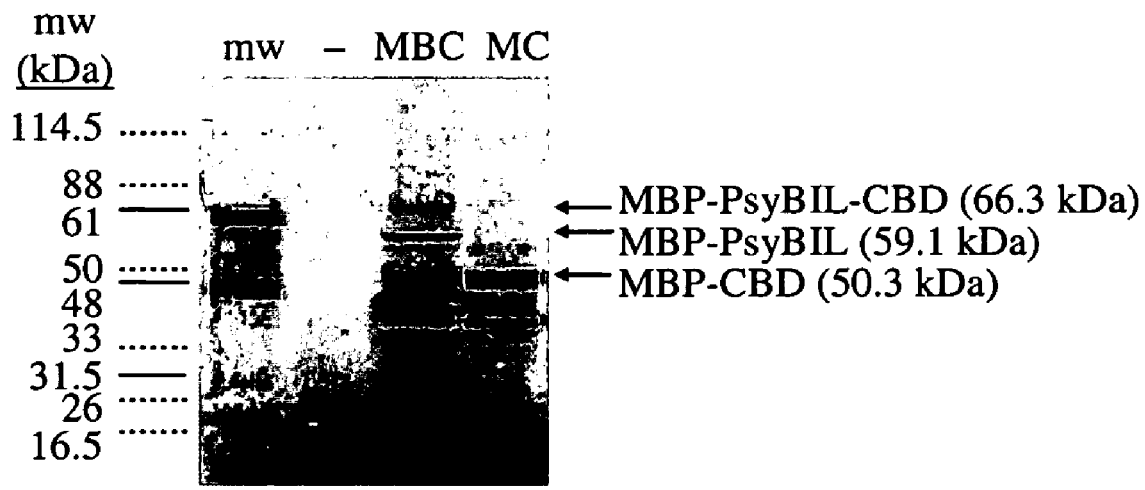
FIGS. 5a-b are autoradiographs depicting SDS-PAGE separation of in-vitro translated, [$^{35}$S]-methionine-labeled, protein products of the MBP-BIL-CBD expression constructs pC2C-PsyBIL, and pC2C-RspBIL2 (FIGS. 5a and 5b, respectively, "MBC" lane). Translation of control constructs pC2C ("MC" lane) was used as a positive control and no DNA template ("-" lane) were used as a negative control. Molecular weights were estimated using translation products of pBESTluc as reference standards.

BIL Domain-Mediated Auto-Cleavage/Auto-Splicing Activity:

Type A BIL domain-mediated auto-cleavage/auto-splicing activity in an in-vitro transcription/translation system: Electrophoretic analysis (FIG. 5a) showed that protein products generated following in-vitro transcription/translation of the MBP-PsyBIL-CBD expression construct pC2C-PsyBIL displayed molecular weights corresponding to the uncleaved precursor MBP-PsyBIL-CBD, the splicing product MBP-CBD, and the carboxy terminal cleavage product MBP-PsyBIL. Two additional protein products displayed molecular weights of 43 and 45 kDa. Control reactions using the MBP-CBD expression construct pC2C as a transcription template produced two protein products, one corresponding in weight to MBP-CBD and the other to the MBP portion thereof. The latter may be observed in chimeric proteins having MBP as an amino terminal tag (refer to: NEB instruction manual "pMAL protein fusion and purification system", Catalog #E8000S). The 43 kDa protein product may represent a premature transcription or translation stop side product unrelated to BIL domain-mediated activity. Appearance of the 45 kDa band, not seen in the control reaction and slightly larger than the expected weight of MBP, may be due to an additional termination point introduced in the BIL domain. As radioactive methionine was used to label the reaction products, and as, unlike the MBP and BIL domains, the CBD domain lacks a methionine residue, its isolated product cannot be visualized according to the protocol employed.

The relative amounts of the MBP-PsyBIL-CBD, MBP-PsyBIL and MBP-CBD protein products were found to be 15%, 57% and 28%, respectively.

These results therefore demonstrated the capacity of Type A BIL domains to auto-cleave and auto-splice flanking sequences.

Figure 5B:
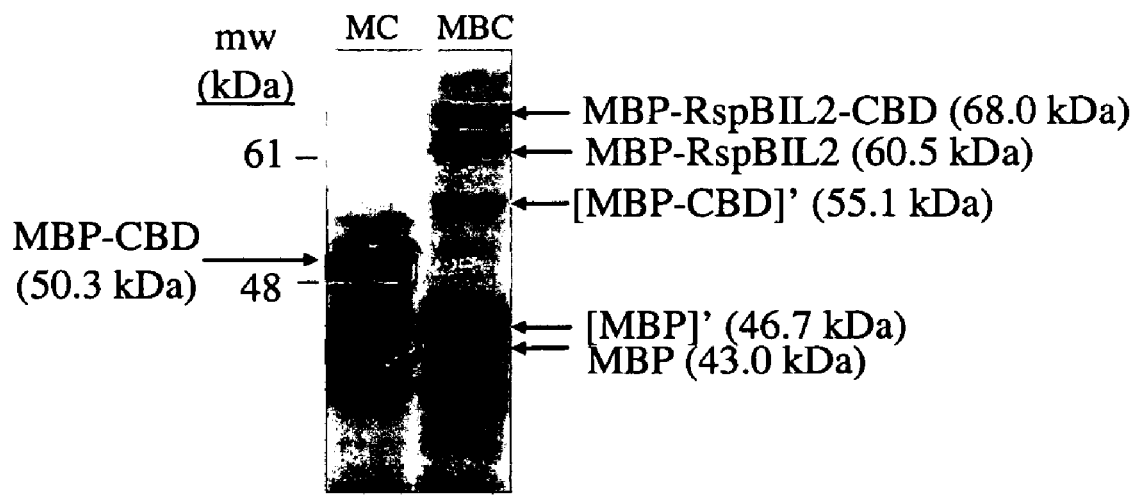

Type B BIL domain-mediated auto-cleavage and auto-splicing activity in an in-vitro transcription/translation system: Electrophoretic analysis (FIG. 5b) showed that protein products generated following in-vitro translation of the MBP-RspBIL2-CBD expression construct pC2C-RspBIL2 included proteins with sizes corresponding to the unprocessed MBP-RspBIL2-CBD precursor, the carboxy terminal cleavage product MBP-RspBIL2, the MBP-containing amino terminal cleavage product, and the splicing product MBP-CBD. Also apparent was a 43 kDa MBP-containing fragment which also appeared in the control reaction, as described above.

These results therefore demonstrated the capacity of Type B BIL domains to auto-cleave and auto-splice flanking sequences. The putative protein splicing motifs and catalytic residues of the FhaB_psesy amino acid sequence responsible for the observed autoprocessing activity are shown in FIG. 5c (SEQ ID NO: 107).

Recombinant BIL domains expressed in-vivo in E. coli display auto-cleavage and auto-splicing activity—mass spectrometric confirmation of BIL-mediated autoprocessing activity: In order to examine the possibility of industrially producing functional recombinant Type A BIL domain, pC2C-PsyBIL was overexpressed in-vivo in E. coli, and the recombinant protein products were analyzed for BIL domain-mediated autoprocessing activity.

Figure 6A:
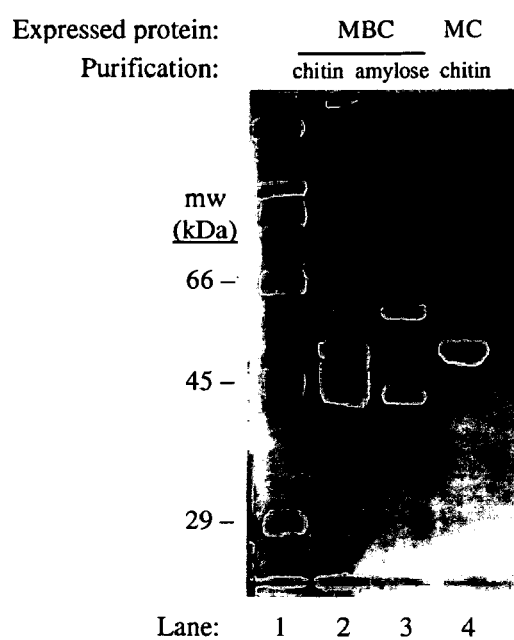
FIGS. 6a-b are photographs depicting SDS-PAGE analysis of autocatalytically processed protein products overexpressed in-vivo in E. coli transformed with the MBP-PsyBIL-CBD ("MBC" lane) expression construct pC2C-PsyBIL.
Figure 6B:
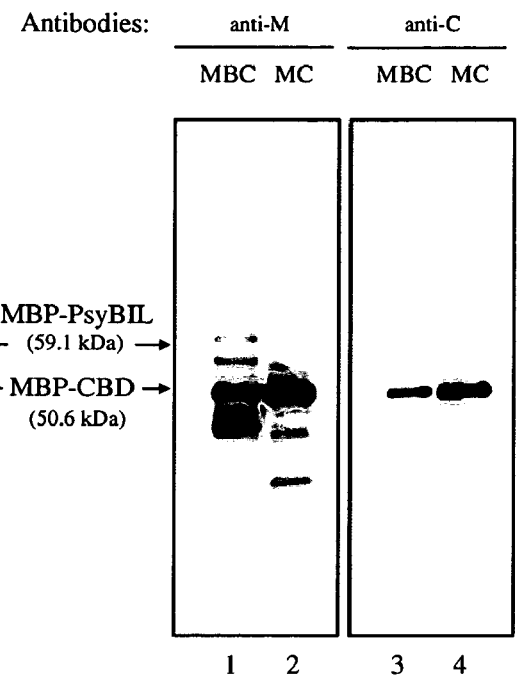

Similarly to the in-vitro results described above, purified protein from E. coli transformed with pC2C-PsyBIL was found to include a protein product having a molecular weight corresponding to the MBP-PsyBIL carboxy terminal cleavage product, as well as a protein product having a molecular weight corresponding to the MBP-CBD auto-splicing product, as determined by both Coomassie Blue staining and Western immunoblotting analysis of SDS-PAGE separated proteins (FIGS. 6a and 6b, respectively). The main product was again observed to be MBP-PsyBIL protein, as displayed by comparing the quantity thereof produced to that of the MBP-CBD protein product when both were purified using amylose beads (FIG. 6a, lane 3).

Figure 6C:
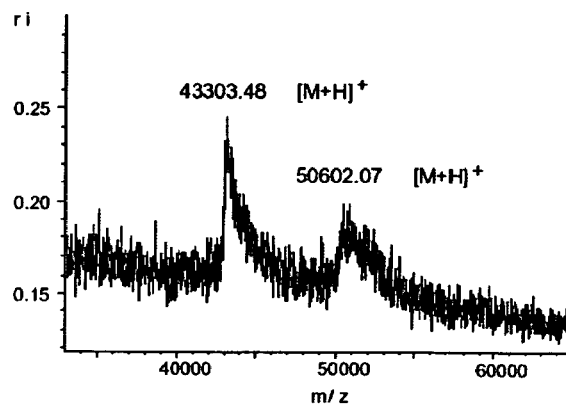
FIGS. 6c-d are data plots depicting MALDI mass spectra of MBP-CBD ligation product (FIG. 6c) and MBP-PsyBIL carboxy terminal cleavage product (FIG. 6d) electroeluted from SDS-PAGE gels. The expected molecular weights of MBP-PsyBIL-CBD and of its carboxy terminal cleavage product MBP-PsyBIL, and its MBP-CBD splicing product were 66.3 and 59.1, and 50.6 kDa, respectively.
Figure 6D:
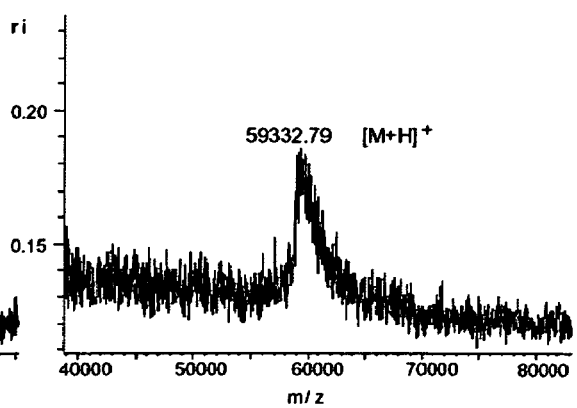

The identities of the PsyBIL reaction products, the MBP-CBD and MBP-BIL protein products were also confirmed by mass spectrometry analysis (FIGS. 6c and 6d, respectively). The measured mass of the MBP-CBD protein (50,602.07 Da) was found to be in close agreement to the expected mass of the unmodified protein (50,266.39 Da). The measured and expected masses of MBP-BIL protein were also found to be in close agreement: 59,332.79 and 59,070.11 Da, respectively. A prominent peak with a mass of 43,303 Da, was also observed in MALDI spectra of electroeluted 50 kDa MBP-CBD protein. Such cross-contamination can be observed in gel purified protein bands (A. Shainskaya, unpublished).

Reactivity of the 43 kDa band with anti MBP tag antibody (FIG. 6b) indicates that this band is a truncated product.

Peptide mass mapping of the 50.1 and 59.3 kDa protein products proteins by MALDI analysis (Tables 3 and 4, respectively) confirmed their assigned identity as MBP-CBD (FIG. 7; SEQ ID NO: 108) and MBP-BIL (FIG. 8; SEQ ID NO: 109), respectively, in particular by identifying the splice junction of the MBP-CBD protein (peptide position 388-396; FIG. 7; Table 3) and the carboxy terminal end of the MBP-BIL protein (peptide position 535-541; FIG. 8; Table 4) with accuracies of 27 and 100 ppm, respectively.

Thus, following extensive experimentation, the splicing junction and cleavage points were found to precisely correspond to those predicted from the sequence similarity of the BIL and intein domains, thereby unambiguously demonstrating BIL domain autoprocessing capacity.

TABLE 3

MALDI identification of peptides of the 50.1 kDa MBP-CBD splicing product of MBP-PsyBIL-CBD.

| Peptide position* | $[M + H]^+$ calculated mass (Da) | $[M + H]^+$ measured mass (Da) | Mass accuracy (ppm) |
| --- | --- | --- | --- |
| 1-2 | 278.1538 | 278.1460 | 28 |
| 3-7 | 563.2677 | 563.2599 | 13 |
| 8-16 | 1057.604 | 1057.596 | 7 |
| 8-26 | 2047.363 | 2047.35 | 6 |
| 27-35 | 1064.532 | 1064.586 | 50 |
| 28-35 | 936.442 | 936.491 | 52 |
| 28-30 | 423.2244 | 423.215 | 22 |
| 90-99 | 1267.647 | 1267.6 | 37 |
| 129-138 | 1201.522 | 1201.602 | 66 |
| 129-141 | 1571.732 | 1571.823 | 57 |
| 191-201 | 1188.642 | 1188.711 | 58 |
| 172-180 | 1129.55 | 1129.57 | 17 |
| 253-274 | 2137.972 | 2138.147 | 81 |
| 279-296 | 2095.812 | 2096.030 | 104 |
| 297-306 | 1010.472 | 1010.612 | 138 |
| 328-345 | 2109.02 | 2109.017 | 1 |
| 356-387 | 3461.516 | 3461.33 | 53 |
| 364-387 | 2576.53 | 2576.41 | 46 |
| 388-396 | 983.48 | 983.55 | 71 |
| 397-435 | 3986.34* | 3986.13 | 52 |
| 397-438 | 4380.80* | 4379.90 | 205 |
| 439-461 | 2634.93* | 2634.72 | 79 |

*mass corresponds to peptide with an alkylated cysteine residue

Figure 9:
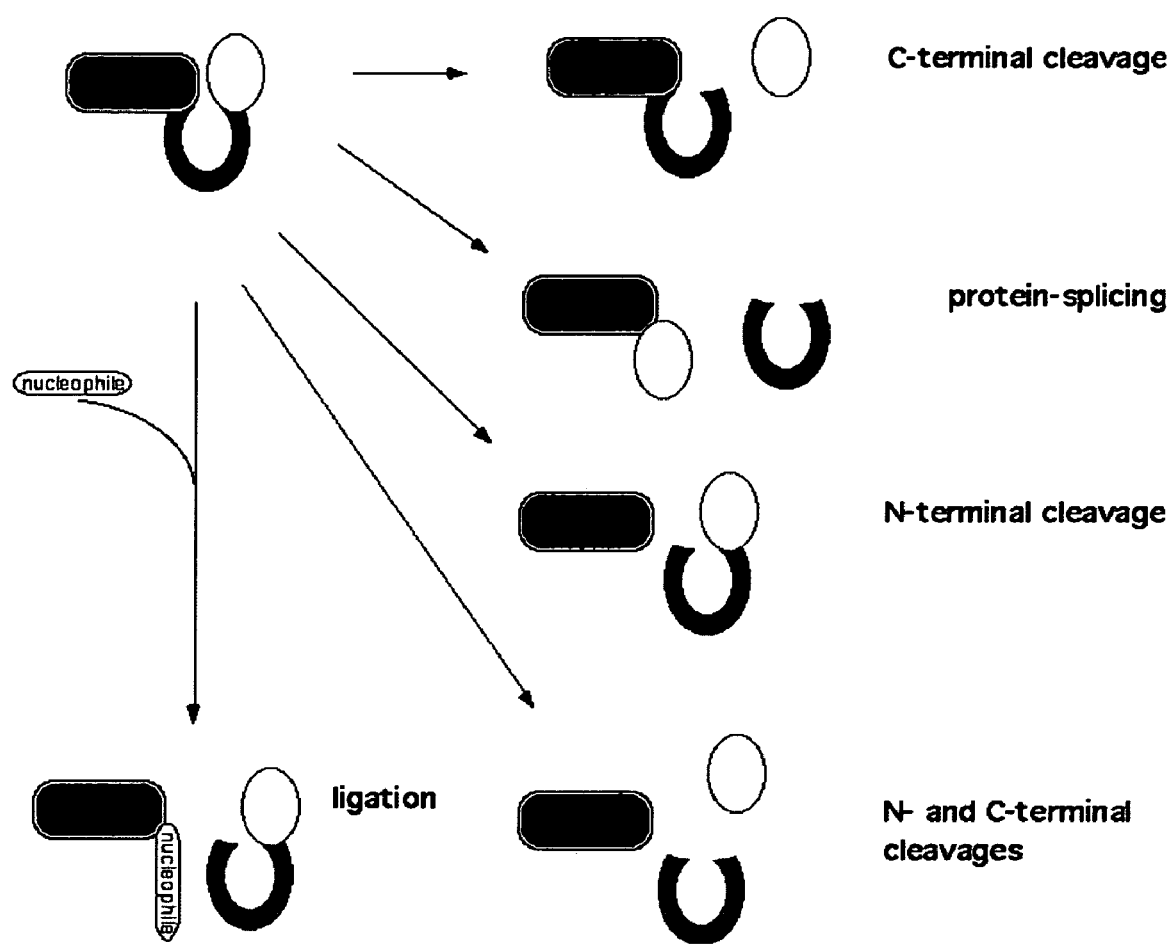
FIG. 9 is a schematic diagram depicting functions of BIL domains. Hint domains are shown as dark gray horseshoes with their flanks as ovals. Proteins are depicted with amino termini positioned on the left.

These results therefore fully and clearly demonstrate the capacity of BIL domains to auto-cleave and auto-splice flanking sequences, similarly to inteins. The presently described BIL domains therefore represent a novel and highly useful class of autoprocessing proteins which can be harnessed for manipulating and modifying proteins, for example as depicted in FIG. 9. These results furthermore demonstrate the suitability of utilizing genetically transformed host cells, such as E. coli, to industrially express chimeric proteins which comprise functional BIL domains.

TABLE 4

MALDI-identification of carboxy terminal peptides of the 59.3 kDa MBP-PsyBIL carboxy terminal cleavage product of MBP-PsyBIL-CBD.

| Peptide position | $[M + H]^+$ calculated mass (Da) | $[M + H]^+$ measured mass (Da) | Mass accuracy (ppm) |
| --- | --- | --- | --- |
| 535-541 | 897.4947 | 897.47 | 27 |
| 537-541 | 656.3156 | 656.25 | 100 |

Discussion: BIL domains are present in several hypervariable bacterial proteins, such as FhaB adhesins and MafB proteins of *Neisseria* strains. Their immediate flanks are the most variable portions of the proteins and they themselves are not always present in these proteins, even in closely related strains of the same species. Some, and perhaps all, proteins with BIL domains seem to be secreted proteins. BIL domains might enhance the variability of secreted proteins by their protein splicing and cleavage activity as detailed below.

As described above, the amino terminal ends of BIL domains, and of Hint domains of inteins and Hog proteins are very similar (FIGS. 3*a-z*). Thus all these domains probably form labile ester bonds on their amino terminal ends. In proteins with BIL domains these ester bonds could be attacked by various nucleophilic molecules, including peptides, proteins and small reactive compounds, such as glutathione or cysteine. Such reactions would ligate the attacking nucleophiles to a carboxy terminal position of the host protein and release the BIL domain and the host protein region downstream to it. This is analogous to Hedgehog protein maturation where the Hint domain mediates the attachment of a cholesterol molecule to the cleaved Hedge domain. In adhesins with BIL domains this putative ligation might serve to covalently attach the bacteria to its adhesion target. Additionally, released BIL and carboxy terminal domains could have a function of their own. For example, in pathogenic bacteria that have such proteins, the released domains could serve as decoys to the immune system.

In *Neisseria* strains, sequences encoding BIL domains appear as either as short open reading frames downstream of MafB genes and in the carboxy terminal ends of these proteins upstream of a variable domain. This suggests that, at least in such *Neisseria* strains, BIL domains function as cassettes which can be fused to genes by genetic rearrangement to promote the variability of the encoded proteins. Other microevolutionary processes in *Neisseria* and *Ralstonia solanacearum*, a plant pathogen bacterium with a wide host range, are known to generate different carboxy terminal ends for surface-exposed and virulence proteins (Parkhill et al., 2000. Nature, 404, 502-506; Salanoubat et al., 2002. Nature 415, 497-502).

Not all species with BIL domains are pathogens and many pathogenic bacteria with fully sequenced genomes do not have BIL domains. BIL domains might be used in different processes not connected with pathogenicity. For example, BIL domain activity might be one way for bacteria to attach to diverse surfaces.

In summary, two novel types of Hint domain-containing proteins, BIL Types A and B, were identified. Both types have the active site sequence features of the Hint domains but also possess sequence features that distinguish them from the known Hint domains and from each other. BIL domains appear in different proteins from diverse bacteria, including pathogenic species of humans and plants, such as *Neisseria meningitidis* and *P. syringae*. These domains are present in variable protein regions and are typically flanked by domains that also appear in secreted proteins such as filamentous hemagglutinin and calcium binding RTX repeats. Phylogenetic and genomic analysis of BIL domain sequences suggests that they were positively selected for in different lineages. Type A and Type B BIL domains were cloned and shown to display auto-cleavage and auto-splicing of flanking polypeptide sequences in an in-vitro transcription/translation system, as well as when overexpressed in *E. coli*, thereby indicating the capacity of BIL domains to autocatalyze post-translational modifications of host proteins.

Conclusion: The above-described experimental results demonstrate the capacity of the autoprocessing polypeptides of the present invention to efficiently auto-cleave and auto-splice flanking sequences. The presently described experimental results furthermore demonstrate the feasibility of utilizing genetically transformed host cells, such as *E. coli*, for efficient industrial production of such autoprocessing polypeptides. Thus, the autoprocessing polypeptides and the polynucleotides encoding such polypeptides of the present invention significantly expand and enhance the available repertoire of available autoprocessing polypeptides having utility in numerous commercially important protein engineering applications, such as protein purification, affinity selection of display phages and post-translational protein ligation.

Example 2

Supplementary Evidence Demonstrating C-Terminal In-Vitro and In-Vivo Autocleavage by Chimeric Protein Including the Type B BIL Domain BIL2_rhosp Materials and Methods:

In order to analyze the capacity of Type B BIL domain BIL2_rhosp (Table 1, FIG. 1*b*) to display autoprocessing activity, genetic sequences encoding this BIL domain including one flanking amino acid residue at each terminus were cloned for expression as a chimeric protein tagged at its amino terminal end with the malE gene-encoded maltose-binding protein (MBP) affinity tag, and at the carboxy terminal end with the *B. circulans* cbd gene-encoded chitin-binding domain (CBD) affinity tag. The resultant "MBP-RspBIL2a-CBD" chimera was expressed in-vivo and in-vitro and resulting protein products were analyzed for evidence of BIL domain-mediated autoprocessing activity according to methods described in Example 1 above.

Figure 10A:
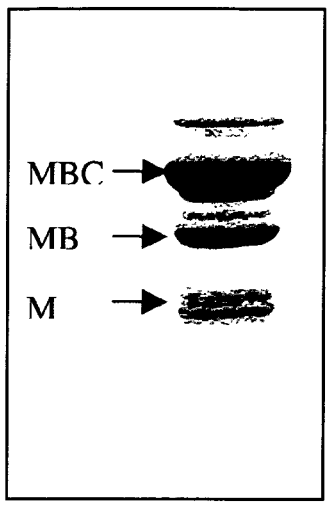
FIGS. 10a-c are electrophoretic analyses depicting C-terminal auto-cleavage by MBP-RspBIL2a-CBD chimera.
Figure 10B:
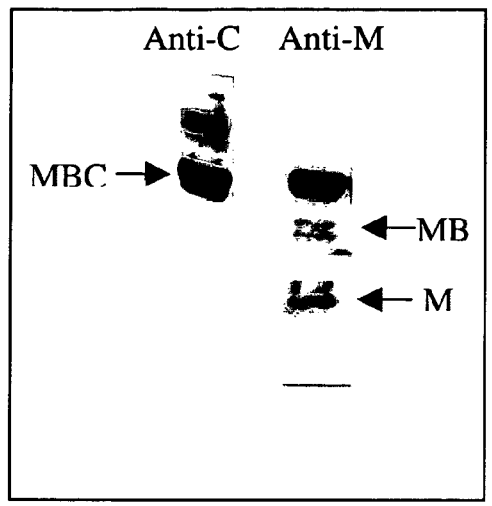
Figure 10C:
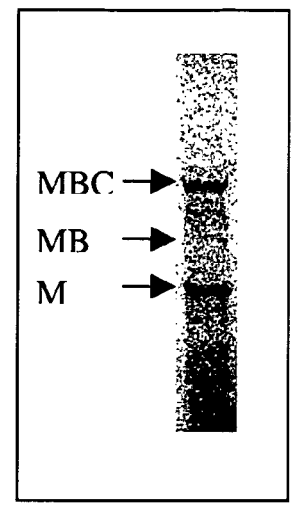

Experimental Results:

The in-vivo expressed MBP-RspBIL2a-CBD chimera was shown to display C-terminal auto-cleavage activity via amylose-based affinity purification, electrophoretic separation, and Coomassie blue staining of the electrophoretically separated proteins (FIG. 10*a*). The in-vivo expressed MBP-RspBIL2a-CBD chimera was also shown to display C-terminal cleavage via Western immunoblotting analysis of SDS-PAGE separated proteins (FIG. 10*b*). The in-vitro expressed MBP-RspBIL2a-CBD chimera was shown to display C-terminal cleavage following [$^{35}$S]-methionine-labeling and autoradiography of electrophoretically separated protein (FIG. 10*c*). Evidence from intact mass mass-spectrometry of the MBP-BIL specific carboxy terminal cleavage product indicates that the C-terminal end of this product is located 6-11 amino acid residues from the predicted carboxy terminal end of the BIL domain towards the N-terminus. Evidence for the MBP-RspBIL2a identity of the cleavage product was obtained from Western Blot, and affinity column analysis. The presence of the protein chaperone DnaK was detected during affinity purification of the BIL products. This chaperone may bind the BIL domain, and may also be involved in its activity.

Conclusion: There is ample evidence that a chimeric protein which comprises the type B BIL domain BIL2_rhosp has the capacity to efficiently display carboxy terminal auto-cleavage activity. Hence, such a BIL domain can therefore be

Example 3

N-Terminal Autocleavage of In-Vivo Expressed Chimeric Polypeptide Comprising the Type B BIL Domain 4825_rhosp Materials and Methods:

In order to analyze the capacity of Type B BIL domain 4825_rhosp (Table 1, FIG. 1*b*) to display autoprocessing activity, genetic sequences encoding this BIL domain with 14 amino terminal-flanking and 51 carboxy terminal-flanking amino acids were cloned for expression as a chimeric protein tagged at its amino terminal end with the malE gene-encoded maltose-binding protein (MBP) affinity tag, and at the carboxy terminal end with the *B. circulans* cbd gene-encoded chitin-binding domain (CBD) affinity tag. The resultant "MBP-4825rhosp-CBD" chimera was expressed in-vivo and resulting protein products were analyzed for evidence of BIL domain-mediated autoprocessing activity according to methods described in Example 1 above.

Experimental Results:

The in-vivo expressed MBP-4825rhosp-CBD chimera was shown to display N-terminal auto-cleavage activity via chitin or amylose based affinity purification of expressed protein and electrophoretic separation, and Coomassie blue staining of electrophoretically separated protein (FIG. 11*a*). The chimera was also shown to display N-terminal cleavage via Western immunoblotting analysis of SDS-PAGE separated proteins using anti-CBD and anti-MBP antibodies (FIG. 11*b*). The cleavage site was found to be located exactly between the predicted N-terminal residue of the BIL domain and the amino terminal flanking sequence as demonstrated by amino terminal end sequencing. Large amounts of the chaperone GroEL were detected during the purification of the protein products when overexpressing the MBP-4825rhosp-CBD chimera the whereas no GroEL was detected when overexpressing control chimera lacking the BIL domain.

Conclusion: A chimeric protein which comprises the type B BIL domain 4825_rhosp has the capacity to efficiently display N-terminal auto-cleavage activity. Hence, such a BIL domain can therefore be advantageously exploited in applications benefiting from an auto-cleaving chimeric protein.

Example 4

Auto-Splicing and C-Terminal Auto-Cleavage of In-Vivo Expressed Chimeric Protein Including the Type A BIL Domain BIL4_cloth Materials and Methods:

In order to analyze the capacity of Type A BIL domain BIL4_cloth (Table 1, FIG. 1*a*) to display autoprocessing activity, genetic sequences encoding this BIL domain were cloned, including one flanking amino acid residue of the host protein at the C-terminal end, for expression as a chimeric protein tagged at its amino terminal end with the malE gene-encoded maltose-binding protein (MBP) affinity tag, and at the carboxy terminal end with the *B. circulans* cbd gene-encoded chitin-binding domain (CBD) affinity tag. The resultant "MBP-BIL4cloth-CBD" chimera was expressed in-vivo and resulting protein products were analyzed for evidence of BIL domain-mediated autoprocessing activity according to methods described in Example 1 above.

Experimental Results:

The in-vivo expressed MBP-BIL4cloth-CBD chimera was shown to display auto-splicing activity (MBP-CBD specific fragment) as shown by Western immunoblotting assay using anti CBD and anti MBP antibody probes (FIGS. 12*a* and 12*b*, respectively), and as shown by Coomassie blue staining of electrophoretically separated protein products isolated via amylose based or chitin based affinity chromatography depicting auto-splicing activity. The identity of the auto-splicing product was verified via mass-spectrometry peptide mapping (data not shown). Carboxy terminal auto-cleavage activity (MBP-BIL domain specific fragment) was also detected by Western immunoblotting assay using an anti MBP antibody probe (FIG. 12*b*) and by Coomassie blue staining of electrophoretically separated protein products isolated via amylose based affinity chromatography (FIG. 12*c*).

Conclusion: A chimeric protein which comprises A type a BIL domain, such as the type A BIL domain BIL4_cloth, has the capacity to efficiently display auto-splicing and carboxy terminal auto-cleaving activity. Hence, such a BIL domain can therefore be advantageously exploited in applications benefiting from an auto-splicing and/or carboxy terminal auto-cleaving chimeric protein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by their accession numbers mentioned in this specification are herein incorporated in their entirety by reference into the specification, to the same extent as if each individual publication, patent, patent application or sequence identified by their accession number was specifically and individually indicated to be incorporated herein by reference. In addition, citation or identification of any reference in this application shall not be construed as an admission that such reference is available as prior art to the present invention.

SEQUENCE LISTING

<160> NUMBER OF SEQ ID NOS: 109

<210> SEQ ID NO 1
<211> LENGTH: 25

```
<212> TYPE: DNA
<213> ORGANISM: artificial sequence
<220> FEATURE:
<223> OTHER INFORMATION: Single strand DNA oligonucleotide

<400> SEQUENCE: 1
aaatgtcgac tgcggtggcc tgacc                                         25

<210> SEQ ID NO 2
<211> LENGTH: 25
<212> TYPE: DNA
<213> ORGANISM: artificial sequence
<220> FEATURE:
<223> OTHER INFORMATION: Single strand DNA oligonucleotide

<400> SEQUENCE: 2
tgtcgtattg cttcctttcg ggctt                                         25

<210> SEQ ID NO 3
<211> LENGTH: 33
<212> TYPE: DNA
<213> ORGANISM: artificial sequence
<220> FEATURE:
<223> OTHER INFORMATION: Single strand DNA oligonucleotide

<400> SEQUENCE: 3
tgcggtggcc tgaccggtct gaactcaggc ctc                                33

<210> SEQ ID NO 4
<211> LENGTH: 29
<212> TYPE: DNA
<213> ORGANISM: artificial sequence
<220> FEATURE:
<223> OTHER INFORMATION: Single strand DNA oligonucleotide

<400> SEQUENCE: 4
aaaaggatcc tgctttgcgg ccggaacga                                     29

<210> SEQ ID NO 5
<211> LENGTH: 32
<212> TYPE: DNA
<213> ORGANISM: artificial sequence
<220> FEATURE:
<223> OTHER INFORMATION: Single strand DNA oligonucleotide

<400> SEQUENCE: 5
aaaatctaga ggtattatgc acccatgtct tg                                 32

<210> SEQ ID NO 6
<211> LENGTH: 27
<212> TYPE: DNA
<213> ORGANISM: artificial sequence
<220> FEATURE:
<223> OTHER INFORMATION: Single strand DNA oligonucleotide

<400> SEQUENCE: 6
gaattcggtg attcatcctt ggggcga                                       27

<210> SEQ ID NO 7
<211> LENGTH: 28
<212> TYPE: DNA
<213> ORGANISM: artificial sequence
<220> FEATURE:
<223> OTHER INFORMATION: Single strand DNA oligonucleotide

<400> SEQUENCE: 7
```
tctagaaaaa cacggcaagg gcgagcgg                                      28

<210> SEQ ID NO 8
<211> LENGTH: 143
<212> TYPE: PRT
<213> ORGANISM: Neisseria meningitidis
<220> FEATURE:
<221> NAME/KEY: misc_feature
<222> LOCATION: (36)..(62)
<223> OTHER INFORMATION: Xaa can be any naturally occurring amino acid
<220> FEATURE:
<221> NAME/KEY: misc_feature
<222> LOCATION: (78)..(80)
<223> OTHER INFORMATION: Xaa can be any naturally occurring amino acid
<220> FEATURE:
<221> NAME/KEY: misc_feature
<222> LOCATION: (110)..(113)
<223> OTHER INFORMATION: Xaa can be any naturally occurring amino acid
<220> FEATURE:
<221> NAME/KEY: misc_feature
<222> LOCATION: (129)..(135)
<223> OTHER INFORMATION: Xaa can be any naturally occurring amino acid

<400> SEQUENCE: 8

Ser Phe His Gly Ser Thr Leu Val Lys Thr Ala Asp Gly Tyr Lys Ala
1               5                   10                  15

Ile Ala His Ile Gln Ala Gly Asp Arg Val Phe Ala Lys Asp Glu Thr
            20                  25                  30

Ser Gly Lys Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Asn Asn
    50                  55                  60

Gln Thr Leu Ile Ser Asn Lys Ile His Pro Phe Tyr Ser Xaa Xaa Xaa
65                  70                  75                  80

Trp Ile Gln Ala Gly Arg Leu Lys Lys Gly Asp Thr Leu Leu Ser Glu
                85                  90                  95

Ser Gly Ala Lys Gln Thr Val Gln Asn Ile Thr Leu Lys Xaa Xaa Xaa
            100                 105                 110

Xaa Lys Ala Tyr Asn Leu Thr Val Ala Asp Trp His Thr Tyr Phe Val
        115                 120                 125

Xaa Xaa Xaa Xaa Xaa Xaa Xaa Glu Gly Val Trp Val His Asn Glu
    130                 135                 140

<210> SEQ ID NO 9
<211> LENGTH: 143
<212> TYPE: PRT
<213> ORGANISM: Neisseria meningitidis (group B)
<220> FEATURE:
<221> NAME/KEY: misc_feature
<222> LOCATION: (36)..(62)
<223> OTHER INFORMATION: Xaa can be any naturally occurring amino acid
<220> FEATURE:
<221> NAME/KEY: misc_feature
<222> LOCATION: (78)..(80)
<223> OTHER INFORMATION: Xaa can be any naturally occurring amino acid
<220> FEATURE:
<221> NAME/KEY: misc_feature
<222> LOCATION: (110)..(113)
<223> OTHER INFORMATION: Xaa can be any naturally occurring amino acid
<220> FEATURE:
<221> NAME/KEY: misc_feature
<222> LOCATION: (129)..(135)
<223> OTHER INFORMATION: Xaa can be any naturally occurring amino acid

<400> SEQUENCE: 9

Ser Phe His Gly Ser Thr Leu Val Lys Thr Ala Asp Gly Tyr Lys Ala
1               5                   10                  15

-continued

```
Ile Ala Arg Ile Arg Thr Gly Asp Arg Val Phe Ala Lys Asp Glu Ala
            20                  25                  30

Ser Gly Lys Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Asn Asn
    50                  55                  60

Gln Thr Leu Ile Ser Asn Lys Ile His Pro Phe Tyr Ser Xaa Xaa Xaa
65                  70                  75                  80

Trp Ile Gln Ala Gly Arg Leu Lys Lys Gly Asp Thr Leu Leu Ser Glu
                85                  90                  95

Ser Gly Ala Lys Gln Thr Val Gln Asn Ile Thr Leu Lys Xaa Xaa Xaa
            100                 105                 110

Xaa Lys Ala Tyr Asn Leu Thr Val Ala Asp Trp His Thr Tyr Phe Val
                115                 120                 125

Xaa Xaa Xaa Xaa Xaa Xaa Xaa Glu Gly Val Trp Val His Asn Asp
            130                 135                 140
```

<210> SEQ ID NO 10
<211> LENGTH: 143
<212> TYPE: PRT
<213> ORGANISM: Neisseria meningitidis (group B)
<220> FEATURE:
<221> NAME/KEY: misc_feature
<222> LOCATION: (36)..(62)
<223> OTHER INFORMATION: Xaa can be any naturally occurring amino acid
<220> FEATURE:
<221> NAME/KEY: misc_feature
<222> LOCATION: (78)..(80)
<223> OTHER INFORMATION: Xaa can be any naturally occurring amino acid
<220> FEATURE:
<221> NAME/KEY: misc_feature
<222> LOCATION: (110)..(113)
<223> OTHER INFORMATION: Xaa can be any naturally occurring amino acid
<220> FEATURE:
<221> NAME/KEY: misc_feature
<222> LOCATION: (129)..(135)
<223> OTHER INFORMATION: Xaa can be any naturally occurring amino acid

<400> SEQUENCE: 10

```
Ser Phe His Gly Ser Thr Leu Val Lys Thr Ala Asp Gly Tyr Lys Ala
1               5                   10                  15

Ile Ala Arg Ile Arg Thr Gly Asp Arg Val Phe Ala Lys Asp Glu Ala
            20                  25                  30

Ser Gly Lys Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Asn Asn
    50                  55                  60

Gln Thr Leu Ile Ser Asn Lys Ile His Pro Phe Tyr Ser Xaa Xaa Xaa
65                  70                  75                  80

Trp Ile Gln Ala Gly Arg Leu Lys Lys Gly Asp Thr Leu Leu Ser Glu
                85                  90                  95

Ser Gly Ala Lys Gln Thr Val Gln Asn Ile Thr Phe Lys Xaa Xaa Xaa
            100                 105                 110

Xaa Lys Ala Tyr Asn Leu Thr Val Ala Asp Trp His Thr Tyr Phe Val
                115                 120                 125

Xaa Xaa Xaa Xaa Xaa Xaa Xaa Glu Gly Val Trp Val His Asn Asp
            130                 135                 140
```

<210> SEQ ID NO 11
<211> LENGTH: 142

```
<212> TYPE: PRT
<213> ORGANISM: Magnetospirillum magnetotacticum
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (37)..(53)
<223> OTHER INFORMATION: Xaa can be any naturally occurring amino acid
<220> FEATURE:
<221> NAME/KEY: misc_feature
<222> LOCATION: (69)..(85)
<223> OTHER INFORMATION: Xaa can be any naturally occurring amino acid
<220> FEATURE:
<221> NAME/KEY: misc_feature
<222> LOCATION: (101)..(119)
<223> OTHER INFORMATION: Xaa can be any naturally occurring amino acid

<400> SEQUENCE: 11

Cys Phe Val Ala Gly Thr Pro Val Arg Met Ala Asp Gly Xaa Glu Lys
 1               5                  10                  15

Ala Ile Glu Thr Val Glu Ile Gly Glu Gln Val Gln Gly Thr Asp Gly
            20                  25                  30

Thr Ile Asn Glu Xaa Xaa Xaa Xaa Xaa Xaa Xaa Xaa Xaa Xaa Xaa Xaa
        35                  40                  45

Xaa Xaa Xaa Xaa Xaa Asn Ser Leu Asp Phe Phe Val Thr Ala Asp His
 50                  55                  60

Pro Phe Leu Thr Xaa Xaa Xaa Xaa Xaa Xaa Xaa Xaa Xaa Xaa Xaa Xaa
 65                  70                  75                  80

Xaa Xaa Xaa Xaa Xaa Ala Leu Asn Val Thr Gln Leu Val Ile Gly Asp
                85                  90                  95

Thr Leu Ile Thr Xaa Xaa Xaa Xaa Xaa Xaa Xaa Xaa Xaa Xaa Xaa Xaa
            100                 105                 110

Xaa Xaa Xaa Xaa Xaa Xaa Xaa Val Val Tyr Asn Leu His Leu Ile Gly
        115                 120                 125

Asn Asn Thr Tyr Val Ala Ser Gly Tyr Tyr Val His Asn Tyr
130                 135                 140

<210> SEQ ID NO 12
<211> LENGTH: 149
<212> TYPE: PRT
<213> ORGANISM: Pseudomonas syringae
<220> FEATURE:
<221> NAME/KEY: misc_feature
<222> LOCATION: (36)..(66)
<223> OTHER INFORMATION: Xaa can be any naturally occurring amino acid
<220> FEATURE:
<221> NAME/KEY: misc_feature
<222> LOCATION: (82)..(86)
<223> OTHER INFORMATION: Xaa can be any naturally occurring amino acid
<220> FEATURE:
<221> NAME/KEY: misc_feature
<222> LOCATION: (102)..(124)
<223> OTHER INFORMATION: Xaa can be any naturally occurring amino acid
<220> FEATURE:
<221> NAME/KEY: misc_feature
<222> LOCATION: (140)..(141)
<223> OTHER INFORMATION: Xaa can be any naturally occurring amino acid

<400> SEQUENCE: 12

Cys Phe Ala Ala Gly Thr Met Val Ser Thr Pro Asp Gly Glu Arg Ala
 1               5                  10                  15

Ile Asp Thr Leu Lys Val Gly Asp Ile Val Trp Ser Lys Pro Glu Gly
            20                  25                  30

Gly Gly Lys Xaa Xaa Xaa Xaa Xaa Xaa Xaa Xaa Xaa Xaa Xaa Xaa Xaa
```

-continued

```
            35                  40                  45
Xaa Xaa Xaa Xaa Xaa Xaa Xaa Xaa Xaa Xaa Xaa Xaa Xaa Xaa
        50                  55                  60

Xaa Xaa Glu Asp Glu Ser Leu Leu Val Thr Pro Gly His Pro Phe Tyr
 65                  70                  75                  80

Val Xaa Xaa Xaa Xaa Xaa Phe Val Pro Val Ile Asp Leu Lys Pro Gly
                85                  90                  95

Asp Arg Leu Gln Ser Xaa Xaa Xaa Xaa Xaa Xaa Xaa Xaa Xaa
                100                 105                 110

Xaa Xaa Xaa Xaa Xaa Xaa Xaa Xaa Xaa Xaa Xaa Lys Thr Tyr Asn
        115                 120                 125

Leu Thr Val Asp Val Gly His Thr Phe Tyr Val Xaa Xaa Leu Lys Thr
130                 135                 140

Trp Val His Asn Thr
145

<210> SEQ ID NO 13
<211> LENGTH: 149
<212> TYPE: PRT
<213> ORGANISM: Pseudomonas fluorescens
<220> FEATURE:
<221> NAME/KEY: misc_feature
<222> LOCATION: (36)..(66)
<223> OTHER INFORMATION: Xaa can be any naturally occurring amino acid
<220> FEATURE:
<221> NAME/KEY: misc_feature
<222> LOCATION: (82)..(86)
<223> OTHER INFORMATION: Xaa can be any naturally occurring amino acid
<220> FEATURE:
<221> NAME/KEY: misc_feature
<222> LOCATION: (102)..(124)
<223> OTHER INFORMATION: Xaa can be any naturally occurring amino acid
<220> FEATURE:
<221> NAME/KEY: misc_feature
<222> LOCATION: (140)..(141)
<223> OTHER INFORMATION: Xaa can be any naturally occurring amino acid

<400> SEQUENCE: 13

Cys Phe Ala Ala Gly Thr Met Val Ala Thr Pro Lys Gly Glu Arg Ala
 1               5                  10                  15

Ile Glu Thr Leu Lys Ile Gly Asp Val Val Trp Ser Lys Pro Glu Gln
                20                  25                  30

Gly Gly Glu Xaa Xaa Xaa Xaa Xaa Xaa Xaa Xaa Xaa Xaa Xaa Xaa
                35                  40                  45

Xaa Xaa Xaa Xaa Xaa Xaa Xaa Xaa Xaa Xaa Xaa Xaa Xaa
        50                  55                  60

Xaa Xaa Ser Ser Glu Thr Leu Glu Val Thr Pro Gly His Pro Phe Tyr
 65                  70                  75                  80

Val Xaa Xaa Xaa Xaa Xaa Phe Val Pro Leu Ile Glu Leu Gln Pro Gly
                85                  90                  95

Asp Arg Leu Gln Ser Xaa Xaa Xaa Xaa Xaa Xaa Xaa Xaa Xaa
                100                 105                 110

Xaa Xaa Xaa Xaa Xaa Xaa Xaa Xaa Xaa Xaa Xaa Arg Thr Tyr Asn
        115                 120                 125

Leu Thr Val Asp Ile Gly His Thr Phe Tyr Val Xaa Xaa Leu Gly Thr
130                 135                 140

Trp Val His Asn Val
145

<210> SEQ ID NO 14
```

```
<211> LENGTH: 149
<212> TYPE: PRT
<213> ORGANISM: Pseudomonas fluorescens
<220> FEATURE:
<221> NAME/KEY: misc_feature
<222> LOCATION: (36)..(66)
<223> OTHER INFORMATION: Xaa can be any naturally occurring amino acid
<220> FEATURE:
<221> NAME/KEY: misc_feature
<222> LOCATION: (82)..(86)
<223> OTHER INFORMATION: Xaa can be any naturally occurring amino acid
<220> FEATURE:
<221> NAME/KEY: misc_feature
<222> LOCATION: (102)..(124)
<223> OTHER INFORMATION: Xaa can be any naturally occurring amino acid
<220> FEATURE:
<221> NAME/KEY: misc_feature
<222> LOCATION: (140)..(141)
<223> OTHER INFORMATION: Xaa can be any naturally occurring amino acid

<400> SEQUENCE: 14

Cys Phe Ala Ala Gly Thr Met Val Ala Thr Pro Ser Gly Asp Arg Ala
1               5                   10                  15

Ile Asp Thr Leu Lys Val Gly Glu Ile Val Trp Ser Lys Pro Glu His
            20                  25                  30

Gly Gly Glu Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Glu Gly Glu Thr Leu Leu Val Thr Pro Ser His Pro Phe Tyr
65                  70                  75                  80

Val Xaa Xaa Xaa Xaa Xaa Phe Val Pro Ala Ile Asn Leu Lys Pro Gly
                85                  90                  95

Asp Leu Leu Gln Ser Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Lys Thr Phe Asn
        115                 120                 125

Leu Thr Val Asp Ile Gly His Thr Phe Tyr Val Xaa Xaa Leu Lys Thr
130                 135                 140

Trp Val His Asn Thr
145

<210> SEQ ID NO 15
<211> LENGTH: 140
<212> TYPE: PRT
<213> ORGANISM: Streptomyces coelicolor
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (37)..(60)
<223> OTHER INFORMATION: Xaa can be any naturally occurring amino acid
<220> FEATURE:
<221> NAME/KEY: misc_feature
<222> LOCATION: (76)..(80)
<223> OTHER INFORMATION: Xaa can be any naturally occurring amino acid
<220> FEATURE:
<221> NAME/KEY: misc_feature
<222> LOCATION: (110)..(113)
<223> OTHER INFORMATION: Xaa can be any naturally occurring amino acid
<220> FEATURE:
<221> NAME/KEY: misc_feature
<222> LOCATION: (129)..(132)
<223> OTHER INFORMATION: Xaa can be any naturally occurring amino acid

<400> SEQUENCE: 15
```

Ser Phe Pro Ala Gly Thr Arg Val Leu Met Ala Asp Gly Xaa Arg Arg
1               5                   10                  15

Ser Ile Glu Gln Ile Glu Ala Gly Asp Leu Val Thr Ala Thr Asp Pro
            20                  25                  30

Thr Thr Gly Glu Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Asp Gly Ser Thr
    50                  55                  60

Leu Thr Ser Thr Thr His His Pro Tyr Trp Ser Xaa Xaa Xaa Xaa Xaa
65                  70                  75                  80

Trp Lys Asn Ala Gly Asp Leu Glu Ala Gly Asp Thr Leu Arg Thr Pro
                85                  90                  95

Gln Asn Thr Ala Val Val Ile Ala Ala Thr His Asp Trp Xaa Xaa Xaa
            100                 105                 110

Xaa Asp Ala Tyr Asp Leu Thr Val Asp Gly Phe His Ser Tyr Tyr Val
        115                 120                 125

Xaa Xaa Xaa Xaa Thr Asp Val Leu Val His Asn Asn
    130                 135                 140

<210> SEQ ID NO 16
<211> LENGTH: 145
<212> TYPE: PRT
<213> ORGANISM: Thermobifida fusca
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (37)..(64)
<223> OTHER INFORMATION: Xaa can be any naturally occurring amino acid
<220> FEATURE:
<221> NAME/KEY: misc_feature
<222> LOCATION: (80)..(84)
<223> OTHER INFORMATION: Xaa can be any naturally occurring amino acid
<220> FEATURE:
<221> NAME/KEY: misc_feature
<222> LOCATION: (114)..(118)
<223> OTHER INFORMATION: Xaa can be any naturally occurring amino acid
<220> FEATURE:
<221> NAME/KEY: misc_feature
<222> LOCATION: (134)..(137)
<223> OTHER INFORMATION: Xaa can be any naturally occurring amino acid

<400> SEQUENCE: 16

Ser Phe Val Pro Gly Thr Leu Val Leu Leu Ala Asp Gly Xaa Tyr Ala
1               5                   10                  15

Pro Ile Glu Thr Ile Thr Val Gly Asp Asp Val Trp Ala Phe Asp Pro
            20                  25                  30

Arg Thr Gly Thr Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

His Gly Gly Val Val Ala Thr Asp Ala His Pro Phe Trp Val Xaa
65                  70                  75                  80

Xaa Xaa Xaa Xaa Trp Val Ala Ala Ile Asp Leu Glu Pro Gly Thr Trp
                85                  90                  95

Leu Arg Thr Ser Ala Gly Thr Trp Val Gln Val Arg Ala Val Ala Val
            100                 105                 110

Arg Xaa Xaa Xaa Xaa Xaa Arg Val His Asn Leu Thr Val Ala Asp Leu
        115                 120                 125

```
His Thr Tyr Tyr Val Xaa Xaa Xaa Xaa Ala Asp Ala Leu Val His Asn
    130                 135                 140

Glu
145

<210> SEQ ID NO 17
<211> LENGTH: 130
<212> TYPE: PRT
<213> ORGANISM: Neisseria gonorrhoeae
<220> FEATURE:
<221> NAME/KEY: misc_feature
<222> LOCATION: (23)..(49)
<223> OTHER INFORMATION: Xaa can be any naturally occurring amino acid
<220> FEATURE:
<221> NAME/KEY: misc_feature
<222> LOCATION: (65)..(67)
<223> OTHER INFORMATION: Xaa can be any naturally occurring amino acid
<220> FEATURE:
<221> NAME/KEY: misc_feature
<222> LOCATION: (97)..(100)
<223> OTHER INFORMATION: Xaa can be any naturally occurring amino acid
<220> FEATURE:
<221> NAME/KEY: misc_feature
<222> LOCATION: (116)..(122)
<223> OTHER INFORMATION: Xaa can be any naturally occurring amino acid

<400> SEQUENCE: 17

Tyr Lys Ala Ile Ala His Ile Gln Ala Gly Asp Arg Val Leu Ser Lys
1               5                   10                  15

Asp Glu Ala Ser Gly Glu Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Asn Ser Gln Thr Leu Ile Ser Asn Arg Ile His Pro Phe Tyr Ser
    50                  55                  60

Xaa Xaa Xaa Trp Ile Lys Ala Glu Asp Leu Lys Ala Gly Ser Arg Leu
65                  70                  75                  80

Leu Ser Glu Ser Gly Lys Thr Gln Thr Val Arg Asn Ile Val Val Lys
                85                  90                  95

Xaa Xaa Xaa Xaa Lys Ala Tyr Asn Leu Thr Val Ala Asp Trp His Thr
            100                 105                 110

Tyr Phe Val Xaa Xaa Xaa Xaa Xaa Xaa Xaa Glu Gly Val Trp Val His
        115                 120                 125

Asn Asp
    130

<210> SEQ ID NO 18
<211> LENGTH: 143
<212> TYPE: PRT
<213> ORGANISM: Neisseria gonorrhoeae
<220> FEATURE:
<221> NAME/KEY: misc_feature
<222> LOCATION: (36)..(62)
<223> OTHER INFORMATION: Xaa can be any naturally occurring amino acid
<220> FEATURE:
<221> NAME/KEY: misc_feature
<222> LOCATION: (78)..(80)
<223> OTHER INFORMATION: Xaa can be any naturally occurring amino acid
<220> FEATURE:
<221> NAME/KEY: misc_feature
<222> LOCATION: (110)..(113)
<223> OTHER INFORMATION: Xaa can be any naturally occurring amino acid
<220> FEATURE:
<221> NAME/KEY: misc_feature
<222> LOCATION: (129)..(135)
<223> OTHER INFORMATION: Xaa can be any naturally occurring amino acid
```

<400> SEQUENCE: 18

```
Pro Phe His Gly Ser Thr Leu Val Lys Thr Ala Asp Gly Tyr Lys Ala
1               5                   10                  15

Ile Ala Arg Ile Arg Val Gly Asp His Val Phe Ala Lys Asp Glu Ala
            20                  25                  30

Ser Gly Glu Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Asn Asn
    50                  55                  60

Gln Thr Leu Ile Ser Asn Arg Ile His Pro Phe Tyr Ser Xaa Xaa Xaa
65                  70                  75                  80

Trp Ile Lys Ala Glu Asp Leu Lys Ala Gly Ser Arg Leu Leu Ser Glu
                85                  90                  95

Ser Gly Arg Thr Gln Thr Val Arg Asn Ile Ile Val Lys Xaa Xaa Xaa
            100                 105                 110

Xaa Lys Ala Tyr Asn Leu Thr Val Ala Asp Trp His Thr Tyr Phe Val
        115                 120                 125

Xaa Xaa Xaa Xaa Xaa Xaa Xaa Glu Gly Val Trp Val His Asn Ala
    130                 135                 140
```

<210> SEQ ID NO 19
<211> LENGTH: 143
<212> TYPE: PRT
<213> ORGANISM: Neisseria gonorrhoeae
<220> FEATURE:
<221> NAME/KEY: misc_feature
<222> LOCATION: (36)..(62)
<223> OTHER INFORMATION: Xaa can be any naturally occurring amino acid
<220> FEATURE:
<221> NAME/KEY: misc_feature
<222> LOCATION: (78)..(80)
<223> OTHER INFORMATION: Xaa can be any naturally occurring amino acid
<220> FEATURE:
<221> NAME/KEY: misc_feature
<222> LOCATION: (110)..(113)
<223> OTHER INFORMATION: Xaa can be any naturally occurring amino acid
<220> FEATURE:
<221> NAME/KEY: misc_feature
<222> LOCATION: (129)..(135)
<223> OTHER INFORMATION: Xaa can be any naturally occurring amino acid

<400> SEQUENCE: 19

```
Ser Phe His Gly Ser Thr Leu Val Arg Thr Ala Asp Gly Tyr Lys Ala
1               5                   10                  15

Ile Ala His Ile Gln Ala Gly Asp Arg Val Leu Ser Lys Asp Glu Ala
            20                  25                  30

Ser Gly Lys Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Asn Ser
    50                  55                  60

Gln Thr Leu Ile Ser Asn Arg Ile His Pro Phe Tyr Ser Xaa Xaa Xaa
65                  70                  75                  80

Trp Ile Lys Ala Glu Asp Leu Lys Ala Gly Asn Arg Leu Phe Ala Glu
                85                  90                  95

Ser Gly Lys Thr Gln Thr Val Arg Asn Ile Val Val Lys Xaa Xaa Xaa
            100                 105                 110

Xaa Lys Ala Tyr Asn Leu Thr Val Ala Asp Trp His Thr Tyr Phe Val
        115                 120                 125

Xaa Xaa Xaa Xaa Xaa Xaa Xaa Glu Gly Val Trp Val His Asn Ser
```

```
                130                 135                 140
```

<210> SEQ ID NO 20
<211> LENGTH: 143
<212> TYPE: PRT
<213> ORGANISM: Neisseria gonorrhoeae
<220> FEATURE:
<221> NAME/KEY: misc_feature
<222> LOCATION: (36)..(62)
<223> OTHER INFORMATION: Xaa can be any naturally occurring amino acid
<220> FEATURE:
<221> NAME/KEY: misc_feature
<222> LOCATION: (78)..(80)
<223> OTHER INFORMATION: Xaa can be any naturally occurring amino acid
<220> FEATURE:
<221> NAME/KEY: misc_feature
<222> LOCATION: (110)..(113)
<223> OTHER INFORMATION: Xaa can be any naturally occurring amino acid
<220> FEATURE:
<221> NAME/KEY: misc_feature
<222> LOCATION: (129)..(135)
<223> OTHER INFORMATION: Xaa can be any naturally occurring amino acid

<400> SEQUENCE: 20

```
Ser Phe His Gly Ser Thr Leu Val Lys Thr Ala Asp Gly Tyr Lys Ala
1               5                   10                  15

Ile Ala His Ile Gln Ala Gly Asp Arg Val Leu Ser Lys Asp Glu Ala
            20                  25                  30

Ser Gly Glu Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Asn Ser
    50                  55                  60

Gln Thr Leu Ile Ser Asn Arg Ile His Pro Phe Tyr Ser Xaa Xaa Xaa
65                  70                  75                  80

Trp Ile Lys Ala Glu Asp Leu Lys Ala Gly Ser Arg Leu Leu Ser Glu
                85                  90                  95

Ser Gly Lys Thr Gln Thr Val Arg Asn Ile Val Val Lys Xaa Xaa Xaa
            100                 105                 110

Xaa Lys Ala Tyr Asn Leu Thr Val Ala Asp Trp His Thr Tyr Phe Val
        115                 120                 125

Xaa Xaa Xaa Xaa Xaa Xaa Xaa Glu Gly Val Trp Val His Asn Asp
    130                 135                 140
```

<210> SEQ ID NO 21
<211> LENGTH: 143
<212> TYPE: PRT
<213> ORGANISM: Neisseria gonorrhoeae
<220> FEATURE:
<221> NAME/KEY: misc_feature
<222> LOCATION: (36)..(62)
<223> OTHER INFORMATION: Xaa can be any naturally occurring amino acid
<220> FEATURE:
<221> NAME/KEY: misc_feature
<222> LOCATION: (78)..(80)
<223> OTHER INFORMATION: Xaa can be any naturally occurring amino acid
<220> FEATURE:
<221> NAME/KEY: misc_feature
<222> LOCATION: (110)..(113)
<223> OTHER INFORMATION: Xaa can be any naturally occurring amino acid
<220> FEATURE:
<221> NAME/KEY: misc_feature
<222> LOCATION: (129)..(135)
<223> OTHER INFORMATION: Xaa can be any naturally occurring amino acid

<400> SEQUENCE: 21

```
Ser Phe His Gly Ser Thr Leu Val Lys Thr Ala Asp Gly Tyr Lys Ala
1               5                   10                  15
```

```
Ile Ala His Ile Gln Ala Gly Asp Arg Val Leu Ser Lys Asp Glu Ala
            20                  25                  30

Ser Gly Glu Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Asn Ser
    50                  55                  60

Gln Thr Leu Ile Ser Asn Arg Ile His Pro Phe Tyr Ser Xaa Xaa Xaa
 65                  70                  75                  80

Trp Ile Lys Ala Glu Asp Leu Lys Ala Gly Ser Arg Leu Phe Ala Glu
                85                  90                  95

Ser Gly Lys Thr Gln Thr Val Arg Asn Ile Ile Val Lys Xaa Xaa Xaa
            100                 105                 110

Xaa Lys Ala Tyr Asn Leu Thr Val Ala Asp Trp His Thr Tyr Phe Val
        115                 120                 125

Xaa Xaa Xaa Xaa Xaa Xaa Xaa Glu Gly Val Trp Val His Asn Asp
    130                 135                 140

<210> SEQ ID NO 22
<211> LENGTH: 143
<212> TYPE: PRT
<213> ORGANISM: Neisseria gonorrhoeae
<220> FEATURE:
<221> NAME/KEY: misc_feature
<222> LOCATION: (36)..(62)
<223> OTHER INFORMATION: Xaa can be any naturally occurring amino acid
<220> FEATURE:
<221> NAME/KEY: misc_feature
<222> LOCATION: (78)..(80)
<223> OTHER INFORMATION: Xaa can be any naturally occurring amino acid
<220> FEATURE:
<221> NAME/KEY: misc_feature
<222> LOCATION: (110)..(113)
<223> OTHER INFORMATION: Xaa can be any naturally occurring amino acid
<220> FEATURE:
<221> NAME/KEY: misc_feature
<222> LOCATION: (129)..(135)
<223> OTHER INFORMATION: Xaa can be any naturally occurring amino acid

<400> SEQUENCE: 22

Pro Phe His Gly Ser Thr Leu Val Lys Thr Ala Asp Gly Tyr Lys Ala
 1               5                  10                  15

Ile Ala His Ile Gln Thr Gly Glu His Val Phe Ala Lys Asp Glu Thr
            20                  25                  30

Ser Gly Lys Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Asn Ser
    50                  55                  60

Gln Thr Leu Ile Ser Asn Arg Ile His Pro Phe Tyr Ser Xaa Xaa Xaa
 65                  70                  75                  80

Trp Ile Lys Ala Glu Asp Leu Lys Ala Gly Ser Arg Leu Leu Ser Glu
                85                  90                  95

Ser Gly Arg Thr Gln Thr Val Arg Asn Thr Val Val Lys Xaa Xaa Xaa
            100                 105                 110

Xaa Lys Ala Tyr Asn Leu Thr Val Ala Asp Trp His Thr Tyr Phe Val
        115                 120                 125

Xaa Xaa Xaa Xaa Xaa Xaa Xaa Glu Gly Val Trp Val His Asn Ser
    130                 135                 140

<210> SEQ ID NO 23
<211> LENGTH: 143
```

```
<212> TYPE: PRT
<213> ORGANISM: Neisseria meningitidis (group C)
<220> FEATURE:
<221> NAME/KEY: misc_feature
<222> LOCATION: (36)..(62)
<223> OTHER INFORMATION: Xaa can be any naturally occurring amino acid
<220> FEATURE:
<221> NAME/KEY: misc_feature
<222> LOCATION: (78)..(80)
<223> OTHER INFORMATION: Xaa can be any naturally occurring amino acid
<220> FEATURE:
<221> NAME/KEY: misc_feature
<222> LOCATION: (110)..(113)
<223> OTHER INFORMATION: Xaa can be any naturally occurring amino acid
<220> FEATURE:
<221> NAME/KEY: misc_feature
<222> LOCATION: (129)..(135)
<223> OTHER INFORMATION: Xaa can be any naturally occurring amino acid

<400> SEQUENCE: 23

Ser Phe His Gly Ser Thr Leu Val Lys Thr Ala Asp Gly Tyr Lys Ala
1               5                   10                  15

Ile Ala His Ile Arg Val Gly Glu Ser Val Phe Ala Lys Asp Glu Thr
            20                  25                  30

Ser Gly Lys Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Asn Ser
    50                  55                  60

Gln Thr Leu Ile Ser Asn Arg Ile His Pro Phe Tyr Ser Xaa Xaa Xaa
65                  70                  75                  80

Trp Ile Gln Ala Gly Arg Leu Lys Lys Gly Asp Thr Leu Leu Ser Glu
                85                  90                  95

Ser Gly Ala Lys Gln Thr Val Gln Asn Ile Thr Leu Lys Xaa Xaa Xaa
            100                 105                 110

Xaa Lys Ala Tyr Asn Leu Thr Val Ala Asp Trp His Thr Tyr Phe Val
        115                 120                 125

Xaa Xaa Xaa Xaa Xaa Xaa Xaa Glu Gly Val Trp Val His Asn Asp
    130                 135                 140

<210> SEQ ID NO 24
<211> LENGTH: 143
<212> TYPE: PRT
<213> ORGANISM: Neisseria meningitidis (group C)
<220> FEATURE:
<221> NAME/KEY: misc_feature
<222> LOCATION: (36)..(62)
<223> OTHER INFOR -continued

```
                35                  40                  45
Xaa Xaa Xaa Xaa Xaa Xaa Xaa Xaa Xaa Xaa Xaa Xaa Xaa Asn Ser
        50                  55                  60

Gln Thr Leu Ile Ser Asn Arg Ile His Pro Phe Tyr Ser Xaa Xaa Xaa
 65                  70                  75                  80

Trp Ile Gln Ala Gly Arg Leu Lys Lys Gly Asp Thr Leu Leu Ser Glu
                85                  90                  95

Ser Gly Ala Lys Gln Thr Val Gln Asn Ile Thr Phe Lys Xaa Xaa Xaa
                100                 105                 110

Xaa Lys Ala Tyr Asn Leu Thr Val Ala Asp Trp His Thr Tyr Phe Val
        115                 120                 125

Xaa Xaa Xaa Xaa Xaa Xaa Xaa Glu Gly Val Trp Val His Asn Ala
        130                 135                 140

<210> SEQ ID NO 25
<211> LENGTH: 143
<212> TYPE: PRT
<213> ORGANISM: Neisseria meningitidis (group C)
<220> FEATURE:
<221> NAME/KEY: misc_feature
<222> LOCATION: (36)..(62)
<223> OTHER INFORMATION: Xaa can be any naturally occurring amino acid
<220> FEATURE:
<221> NAME/KEY: misc_feature
<222> LOCATION: (78)..(80)
<223> OTHER INFORMATION: Xaa can be any naturally occurring amino acid
<220> FEATURE:
<221> NAME/KEY: misc_feature
<222> LOCATION: (110)..(113)
<223> OTHER INFORMATION: Xaa can be any naturally occurring amino acid
<220> FEATURE:
<221> NAME/KEY: misc_feature
<222> LOCATION: (129)..(135)
<223> OTHER INFORMATION: Xaa can be any naturally occurring amino acid

<400> SEQUENCE: 25

Ser Phe His Gly Ser Thr Leu Val Lys Thr Ala Asp Gly Tyr Lys Ala
 1               5                  10                  15

Ile Ala His Ile Arg Val Gly Glu Ser Val Leu Ser Lys Asp Glu Ala
                20                  25                  30

Ser Gly Lys Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Asn Ser
        50                  55                  60

Gln Thr Leu Val Ser Asn Lys Ile His Pro Phe Tyr Ser Xaa Xaa Xaa
 65                  70                  75                  80

Trp Ile Lys Ala Glu Asp Leu Lys Ala Gly Ser Arg Leu Leu Ser Glu
                85                  90                  95

Ser Gly Lys Thr Gln Thr Val Arg Asn Ile Val Val Lys Xaa Xaa Xaa
                100                 105                 110

Xaa Lys Ala Tyr Asn Leu Thr Val Ala Asp Trp His Thr Tyr Phe Val
        115                 120                 125

Xaa Xaa Xaa Xaa Xaa Xaa Xaa Glu Gly Val Trp Val His Asn Ala
        130                 135                 140

<210> SEQ ID NO 26
<211> LENGTH: 143
<212> TYPE: PRT
<213> ORGANISM: Neisseria meningitidis (group C)
<220> FEATURE:
<221> NAME/KEY: misc_feature
<222> LOCATION: (36)..(62)
```

<223> OTHER INFORMATION: Xaa can be any naturally occurring amino acid
<220> FEATURE:
<221> NAME/KEY: misc_feature
<222> LOCATION: (78)..(80)
<223> OTHER INFORMATION: Xaa can be any naturally occurring amino acid
<220> FEATURE:
<221> NAME/KEY: misc_feature
<222> LOCATION: (110)..(113)
<223> OTHER INFORMATION: Xaa can be any naturally occurring amino acid
<220> FEATURE:
<221> NAME/KEY: misc_feature
<222> LOCATION: (129)..(135)
<223> OTHER INFORMATION: Xaa can be any naturally occurring amino acid

<400> SEQUENCE: 26

Ser Phe His Gly Ser Thr Leu Val Lys Thr Ala Asp Gly Tyr Lys Ala
1               5                   10                  15

Ile Ala Arg Ile Arg Thr Gly Asp Arg Val Phe Ala Lys Asp Glu Ala
            20                  25                  30

Ser Gly Lys Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Asn Asn
    50                  55                  60

Gln Thr Leu Ile Ser Asn Lys Ile His Pro Phe Tyr Ser Xaa Xaa Xaa
65                  70                  75                  80

Trp Ile Gln Ala Gly Arg Leu Lys Lys Gly Asp Thr Leu Leu Ser Glu
                85                  90                  95

Ser Gly Ala Lys Gln Thr Val Gln Asn Ile Thr Phe Lys Xaa Xaa Xaa
            100                 105                 110

Xaa Lys Ala Tyr Asn Leu Thr Val Ala Asp Trp His Thr Tyr Phe Val
        115                 120                 125

Xaa Xaa Xaa Xaa Xaa Xaa Xaa Glu Gly Val Trp Val His Asn Ala
    130                 135                 140

<210> SEQ ID NO 27
<211> LENGTH: 143
<212> TYPE: PRT
<213> ORGANISM: Neisseria meningitidis (group C)
<220> FEATURE:
<221> NAME/KEY: misc_feature
<222> LOCATION: (36)..(62)
<223> OTHER INFORMATION: Xaa can be any naturally occurring amino acid
<220> FEATURE:
<221> NAME/KEY: misc_feature
<222> LOCATION: (78)..(80)
<223> OTHER INFORMATION: Xaa can be any naturally occurring amino acid
<220> FEATURE:
<221> NAME/KEY: misc_feature
<222> LOCATION: (110)..(113)
<223> OTHER INFORMATION: Xaa can be any naturally occurring amino acid
<220> FEATURE:
<221> NAME/KEY: misc_feature
<222> LOCATION: (129)..(135)
<223> OTHER INFORMATION: Xaa can be any naturally occurring amino acid

<400> SEQUENCE: 27

Ser Phe His Gly Ser Thr Leu Val Lys Thr Ala Asp Gly Tyr Lys Ala
1               5                   10                  15

Ile Ala His Ile Gln Ala Gly Asp Arg Val Leu Ser Lys Asp Glu Ala
            20                  25                  30

Ser Gly Glu Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Asn Ser
    50                  55                  60

```
Gln Thr Leu Val Ser Asn Lys Ile His Pro Phe Tyr Ser Xaa Xaa Xaa
 65                  70                  75                  80

Trp Ile Gln Ala Gly Arg Leu Lys Lys Gly Asp Thr Leu Leu Ser Glu
                 85                  90                  95

Ser Gly Ala Lys Gln Thr Val Gln Asn Ile Thr Leu Lys Xaa Xaa Xaa
            100                 105                 110

Xaa Lys Ala Tyr Asn Leu Thr Val Ala Asp Trp His Thr Tyr Phe Val
        115                 120                 125

Xaa Xaa Xaa Xaa Xaa Xaa Xaa Glu Gly Val Trp Val His Asn Ser
        130                 135                 140
```

<210> SEQ ID NO 28
<211> LENGTH: 164
<212> TYPE: PRT
<213> ORGANISM: Mannheimia haemolytica
<220> FEATURE:
<221> NAME/KEY: misc_feature
<222> LOCATION: (36)..(62)
<223> OTHER INFORMATION: Xaa can be any naturally occurring amino acid
<220> FEATURE:
<221> NAME/KEY: misc_feature
<222> LOCATION: (78)..(101)
<223> OTHER INFORMATION: Xaa can be any naturally occurring amino acid
<220> FEATURE:
<221> NAME/KEY: misc_feature
<222> LOCATION: (131)..(134)
<223> OTHER INFORMATION: Xaa can be any naturally occurring amino acid
<220> FEATURE:
<221> NAME/KEY: misc_feature
<222> LOCATION: (150)..(156)
<223> OTHER INFORMATION: Xaa can be any naturally occurring amino acid

<400> SEQUENCE: 28

```
Ser Phe His Gly Asp Met Glu Val Lys Thr Asp Lys Gly Tyr Arg Gln
 1               5                  10                  15

Ile Ser Ser Ile Lys Val Gly Asp Lys Val Leu Ala Lys Asn Glu Arg
                20                  25                  30

Thr Gly Ile Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Lys Tyr
        50                  55                  60

His Thr Ile Val Ser Asn Lys Ile His Pro Phe Phe Thr Xaa Xaa Xaa
 65                  70                  75                  80

Xaa Xaa Xaa Xaa Xaa Xaa Xaa Xaa Xaa Xaa Xaa Xaa Xaa Xaa Xaa Xaa
                 85                  90                  95

Xaa Xaa Xaa Xaa Xaa Trp Val Asp Ala Gln His Leu Gln Lys Gly Tyr
            100                 105                 110

Arg Leu Leu Ala Glu Ser Gly Glu Trp Gln Thr Val Thr Lys Val Lys
        115                 120                 125

Ile Lys Xaa Xaa Xaa Xaa Lys Ala Tyr Asn Met Thr Val Glu Lys Asp
        130                 135                 140

His Thr Tyr Phe Ile Xaa Xaa Xaa Xaa Xaa Xaa Xaa Glu Gly Val Trp
145                 150                 155                 160

Val His Asn Asp
```

<210> SEQ ID NO 29
<211> LENGTH: 136
<212> TYPE: PRT
<213> ORGANISM: Clostridium thermocellum
<220> FEATURE:
<221> NAME/KEY: misc_feature
<222> LOCATION: (36)..(57)

<223> OTHER INFORMATION: Xaa can be any naturally occurring amino acid
<220> FEATURE:
<221> NAME/KEY: misc_feature
<222> LOCATION: (73)..(76)
<223> OTHER INFORMATION: Xaa can be any naturally occurring amino acid
<220> FEATURE:
<221> NAME/KEY: misc_feature
<222> LOCATION: (106)..(111)
<223> OTHER INFORMATION: Xaa can be any naturally occurring amino acid
<220> FEATURE:
<221> NAME/KEY: misc_feature
<222> LOCATION: (127)..(128)
<223> OTHER INFORMATION: Xaa can be any naturally occurring amino acid

<400> SEQUENCE: 29

Cys Phe Val Ala Gly Thr Leu Ile Leu Thr Val Ala Gly Leu Val Ala
1               5                   10                  15

Ile Glu Asn Ile Lys Ala Gly Asp Lys Val Ile Ala Thr Asn Leu Glu
            20                  25                  30

Thr Phe Glu Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Asn Gly Glu Val Ile Lys Thr
    50                  55                  60

Thr Phe Glu His Pro Phe Tyr Val Xaa Xaa Xaa Xaa Phe Val Glu Ala
65                  70                  75                  80

Lys Glu Leu Gln Val Gly Asp Lys Leu Leu Asp Ser Lys Gly Asn Val
                85                  90                  95

Leu Val Val Glu Glu Lys Lys Leu Glu Xaa Xaa Xaa Xaa Xaa Xaa Lys
            100                 105                 110

Val Tyr Asn Phe His Val Asp Asp Phe Tyr Thr Tyr His Val Xaa Xaa
        115                 120                 125

Asn Gly Ile Leu Val His Asn Ala
        130                 135

<210> SEQ ID NO 30
<211> LENGTH: 136
<212> TYPE: PRT
<213> ORGANISM: Clostridium thermocellum
<220> FEATURE:
<221> NAME/KEY: misc_feature
<222> LOCATION: (36)..(57)
<223> OTHER INFORMATION: Xaa can be any naturally occurring amino acid
<220> FEATURE:
<221> NAME/KEY: misc_feature
<222> LOCATION: (73)..(76)
<223> OTHER INFORMATION: Xaa can be any naturally occurring amino acid
<220> FEATURE:
<221> NAME/KEY: misc_feature
<222> LOCATION: (106)..(111)
<223> OTHER INFORMATION: Xaa can be any naturally occurring amino acid
<220> FEATURE:
<221> NAME/KEY: misc_feature
<222> LOCATION: (127)..(128)
<223> OTHER INFORMATION: Xaa can be any naturally occurring amino acid

<400> SEQUENCE: 30

Cys Phe Val Ala Gly Thr Met Val Leu Thr Ala Ala Gly Leu Val Ala
1               5                   10                  15

Ile Glu Asn Ile Lys Val Gly Asp Lys Val Ile Ala Ala Asn Pro Glu
            20                  25                  30

Thr Phe Glu Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Gly Gly Glu Val Ile Lys Thr
    50                  55                  60

```
Thr Val Asp His Pro Phe Tyr Val Xaa Xaa Xaa Xaa Phe Val Glu Ala
 65                  70                  75                  80

Val Asn Leu Gln Val Gly Asp Lys Leu Val Asp Ser Lys Gly Asn Val
                 85                  90                  95

Leu Val Val Glu Glu Lys Lys Leu Xaa Xaa Xaa Xaa Xaa Xaa Xaa Lys
            100                 105                 110

Val Tyr Asn Phe Lys Val Asp Asp Phe His Thr Tyr His Val Xaa Xaa
        115                 120                 125

Lys Gly Ile Leu Val His Asn Ala
    130                 135

<210> SEQ ID NO 31
<211> LENGTH: 136
<212> TYPE: PRT
<213> ORGANISM: Clostridium thermocellum
<220> FEATURE:
<221> NAME/KEY: misc_feature
<222> LOCATION: (36)..(57)
<223> OTHER INFORMATION: Xaa can be any naturally occurring amino acid
<220> FEATURE:
<221> NAME/KEY: misc_feature
<222> LOCATION: (73)..(76)
<223> OTHER INFORMATION: Xaa can be any naturally occurring amino acid
<220> FEATURE:
<221> NAME/KEY: misc_feature
<222> LOCATION: (106)..(111)
<223> OTHER INFORMATION: Xaa can be any naturally occurring amino acid
<220> FEATURE:
<221> NAME/KEY: misc_feature
<222> LOCATION: (127)..(128)
<223> OTHER INFORMATION: Xaa can be any naturally occurring amino acid

<400> SEQUENCE: 31

Cys Phe Val Ala Gly Thr Met Ile Leu Thr Ala Thr Gly Leu Val Ala
  1               5                  10                  15

Ile Glu Asn Ile Lys Ala Gly Asp Lys Val Ile Ala Thr Asn Pro Glu
                 20                  25                  30

Thr Phe Glu Xaa Xaa Xaa Xaa Xaa Xaa Xaa Xaa Xaa Xaa Xaa Xaa Xaa
             35                  40                  45

Xaa Xaa Xaa Xaa Xaa Xaa Xaa Xaa Gly Gly Glu Val Ile Lys Thr
 50                  55                  60

Thr Phe Asp His Pro Phe Tyr Val Xaa Xaa Xaa Xaa Phe Val Glu Ala
 65                  70                  75                  80

Gly Lys Leu Gln Val Gly Asp Lys Leu Leu Asp Ser Arg Gly Asn Val
                 85                  90                  95

Leu Val Val Glu Glu Lys Lys Leu Glu Xaa Xaa Xaa Xaa Xaa Xaa Lys
            100                 105                 110

Val Tyr Asn Phe Lys Val Asp Asp Phe His Thr Tyr His Val Xaa Xaa
        115                 120                 125

Asn Glu Val Leu Val His Asn Ala
    130                 135

<210> SEQ ID NO 32
<211> LENGTH: 136
<212> TYPE: PRT
<213> ORGANISM: Clostridium thermocellum
<220> FEATURE:
<221> NAME/KEY: misc_feature
<222> LOCATION: (36)..(57)
<223> OTHER INFORMATION: Xaa can be any naturally occurring amino acid
<220> FEATURE:
<221> NAME/KEY: misc_feature
<222> LOCATION: (73)..(76)
<223> OTHER INFORMATION: Xaa can be any naturally occurring amino acid
```

```
<220> FEATURE:
<221> NAME/KEY: misc_feature
<222> LOCATION: (106)..(111)
<223> OTHER INFORMATION: Xaa can be any naturally occurring amino acid
<220> FEATURE:
<221> NAME/KEY: misc_feature
<222> LOCATION: (127)..(128)
<223> OTHER INFORMATION: Xaa can be any naturally occurring amino acid

<400> SEQUENCE: 32

Cys Phe Val Ala Gly Thr Met Ile Leu Thr Thr Gly Leu Val Ala
1               5                   10                  15

Ile Glu Asn Ile Lys Ala Gly Asp Lys Val Ile Ala Thr Asn Pro Glu
        20                  25                  30

Thr Phe Glu Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Gly Gly Glu Val Ile Lys Thr
    50                  55                  60

Thr Phe Asp His Pro Phe Tyr Val Xaa Xaa Xaa Phe Val Glu Ala
65              70                  75                  80

Lys Gln Leu His Val Gly Asp Lys Leu Leu Asp Ser Lys Gly Asn Val
                85                  90                  95

Leu Val Val Glu Asp Lys Lys Ile Lys Xaa Xaa Xaa Xaa Xaa Lys
                100                 105                 110

Val Tyr Asn Phe Gln Val Ala Asp Phe His Thr Tyr His Val Xaa Xaa
            115                 120                 125

Asn Gly Val Leu Val His Asn Val
        130                 135

<210> SEQ ID NO 33
<211> LENGTH: 136
<212> TYPE: PRT
<213> ORGANISM: Clostridium thermocellum
<220> FEATURE:
<221> NAME/KEY: misc_feature
<222> LOCATION: (36)..(57)
<223> OTHER INFORMATION: Xaa can be any naturally occurring amino acid
<220> FEATURE:
<221> NAME/KEY: misc_feature
<222> LOCATION: (73)..(76)
<223> OTHER INFORMATION: Xaa can be any naturally occurring amino acid
<220> FEATURE:
<221> NAME/KEY: misc_feature
<222> LOCATION: (106)..(111)
<223> OTHER INFORMATION: Xaa can be any naturally occurring amino acid
<220> FEATURE:
<221> NAME/KEY: misc_feature
<222> LOCATION: (127)..(128)
<223> OTHER INFORMATION: Xaa can be any naturally occurring amino acid

<400> SEQUENCE: 33

Cys Phe Val Ala Gly Thr Met Ile Leu Thr Val Ala Gly Leu Val Ala
1               5                   10                  15

Ile Glu Asn Ile Lys Ala Gly Asp Lys Val Ile Ala Thr Asn Pro Glu
        20                  25                  30

Thr Phe Glu Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Asn Gly Asp Val Ile Lys Thr
    50                  55                  60

Thr Phe Glu His Leu Phe Tyr Ala Xaa Xaa Xaa Phe Val Glu Ala
65              70                  75                  80

Lys Glu Leu Gln Val Gly Asp Lys Leu Leu Asp Ser Lys Gly Asn Val
                85                  90                  95
```

-continued

```
Leu Val Val Glu Asp Lys Lys Ile Lys Xaa Xaa Xaa Xaa Xaa Xaa Lys
                100                 105                 110

Val Tyr Asn Phe Gln Val Asp Asp Phe His Thr Tyr His Val Xaa Xaa
            115                 120                 125

Asn Gly Val Leu Val His Asn Val
        130                 135

<210> SEQ ID NO 34
<211> LENGTH: 136
<212> TYPE: PRT
<213> ORGANISM: Clostridium thermocellum
<220> FEATURE:
<221> NAME/KEY: misc_feature
<222> LOCATION: (36)..(57)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (73)..(76)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid
<220> FEATURE:
<221> NAME/KEY: misc_feature
<222> LOCATION: (106)..(111)
<223> OTHER INFORMATION: Xaa can be any naturally occurring amino acid
<220> FEATURE:
<221> NAME/KEY: misc_feature
<222> LOCATION: (127)..(128)
<223> OTHER INFORMATION: Xaa can be any naturally occurring amino acid

<400> SEQUENCE: 34

Cys Phe Val Ala Gly Thr Met Ile Leu Thr Ala Thr Gly Leu Val Ala
1               5                   10                  15

Ile Glu Asn Ile Lys Ala Gly Asp Lys Val Ile Ala Thr Asn Pro Glu
            20                  25                  30

Thr Phe Glu Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Gly Xaa Glu Ile Ile Lys Thr
    50                  55                  60

Thr Leu Gly His Leu Phe Tyr Val Xaa Xaa Xaa Xaa Phe Val Glu Ala
65                  70                  75                  80

Val Lys Leu Gln Pro Thr Asp Lys Leu Val Asp Ser Gly Gly Asn Val
                85                  90                  95

Leu Val Val Glu Xaa Lys Lys Phe Glu Xaa Xaa Xaa Xaa Xaa Xaa Lys
                100                 105                 110

Val Tyr Asn Phe Lys Val Asn Asp Phe Tyr Thr Tyr His Val Xaa Xaa
            115                 120                 125

Asn Gly Ile Leu Val His Asn Val
        130                 135

<210> SEQ ID NO 35
<211> LENGTH: 136
<212> TYPE: PRT
<213> ORGANISM: Clostridium thermocellum
<220> FEATURE:
<221> NAME/KEY: misc_feature
<222> LOCATION: (36)..(57)
<223> OTHER INFORMATION: Xaa can be any naturally occurring amino acid
<220> FEATURE:
```

```
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (73)..(76)
<223> OTHER INFORMATION: Xaa can be any naturally occurring amino acid
<220> FEATURE:
<221> NAME/KEY: misc_feature
<222> LOCATION: (101)..(101)
<223> OTHER INFORMATION: Xaa can be any naturally occurring amino acid
<220> FEATURE:
<221> NAME/KEY: misc_feature
<222> LOCATION: (106)..(111)
<223> OTHER INFORMATION: Xaa can be any naturally occurring amino acid
<220> FEATURE:
<221> NAME/KEY: misc_feature
<222> LOCATION: (127)..(128)
<223> OTHER INFORMATION: Xaa can be any naturally occurring amino acid

<400> SEQUENCE: 35

Cys Phe Val Ala Gly Thr Met Ile Leu Thr Ala Thr Gly Leu Val Ala
1               5                   10                  15

Ile Glu Asn Ile Lys Ala Gly Asp Lys Val Ile Ala Thr Asn Pro Glu
            20                  25                  30

Thr Phe Glu Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Gly Xaa Glu Ile Ile Lys Thr
    50                  55                  60

Thr Leu Gly His Leu Phe Tyr Val Xaa Xaa Xaa Xaa Phe Val Glu Ala
65                  70                  75                  80

Val Lys Leu Gln Pro Thr Asp Lys Leu Val Asp Ser Gly Gly Asn Val
                85                  90                  95

Leu Val Val Glu Xaa Lys Lys Phe Glu Xaa Xaa Xaa Xaa Xaa Xaa Lys
            100                 105                 110

Val Tyr Asn Phe Lys Val Asn Asp Phe Tyr Thr Tyr His Val Xaa Xaa
        115                 120                 125

Asn Gly Ile Leu Val His Asn Val
    130                 135

<210> SEQ ID NO 36
<211> LENGTH: 214
<212> TYPE: PRT
<213> ORGANISM: Leptospira interrogans
<220> FEATURE:
<221> NAME/KEY: misc_feature
<222> LOCATION: (36)..(58)
<223> OTHER INFORMATION: Xaa can be any naturally occurring amino acid
<220> FEATURE:
<221> NAME/KEY: misc_feature
<222> LOCATION: (74)..(151)
<223> OTHER INFORMATION: Xaa can be any naturally occurring amino acid
<220> FEATURE:
<221> NAME/KEY: misc_feature
<222> LOCATION: (181)..(185)
<223> OTHER INFORMATION: Xaa can be any naturally occurring amino acid
<220> FEATURE:
<221> NAME/KEY: misc_feature
<222> LOCATION: (201)..(206)
<223> OTHER INFORMATION: Xaa can be any naturally occurring amino acid

<400> SEQUENCE: 36

Cys Phe Thr Ala Gly Ser Lys Val Thr Lys Leu Lys Asn Phe Ala Asn
1               5                   10                  15

Ile Glu Glu Ile Lys Ile Gly Asp Ile Val Arg Ser Trp Asn Glu Asn
            20                  25                  30
```

```
Thr Asn Thr Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Gly Glu Glu Ile His
 50                  55                  60

Thr Thr Trp Asn His Pro Phe Arg Arg Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa
                 85                  90                  95

Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Xaa Xaa Xaa Xaa
            130                 135                 140

Xaa Xaa Xaa Xaa Xaa Xaa Xaa Trp Val Lys Val Glu Asp Leu Arg Leu
145                 150                 155                 160

Lys Asp Gln Val Leu Arg Ser Asp Gly Ser Trp Gly Thr Val Thr Gly
                165                 170                 175

Ile Tyr Tyr Tyr Xaa Xaa Xaa Xaa Lys Val Tyr Asn Leu Glu Val
            180                 185                 190

Glu Asp Asn His Thr Tyr Val Val Xaa Xaa Xaa Xaa Xaa Ile Gly
        195                 200                 205

Tyr Val Val His Asn Tyr
        210

<210> SEQ ID NO 37
<211> LENGTH: 239
<212> TYPE: PRT
<213> ORGANISM: Leptospira interrogans
<220> FEATURE:
<221> NAME/KEY: misc_feature
<222> LOCATION: (14)..(42)
<223> OTHER INFORMATION: Xaa can be any naturally occurring amino acid
<220> FEATURE:
<221> NAME/KEY: misc_feature
<222> LOCATION: (65)..(87)
<223> OTHER INFORMATION: Xaa can be any naturally occurring amino acid
<220> FEATURE:
<221> NAME/KEY: misc_feature
<222> LOCATION: (103)..(176)
<223> OTHER INFORMATION: Xaa can be any naturally occurring amino acid
<220> FEATURE:
<221> NAME/KEY: misc_feature
<222> LOCATION: (206)..(210)
<223> OTHER INFORMATION: Xaa can be any naturally occurring amino acid
<220> FEATURE:
<221> NAME/KEY: misc_feature
<222> LOCATION: (226)..(231)
<223> OTHER INFORMATION: Xaa can be any naturally occurring amino acid

<400> SEQUENCE: 37

Cys Phe Val Ala Gly Ser Lys Val Thr Lys Leu Lys Asn Xaa Xaa Xaa
 1               5                  10                  15

Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Phe Ala Asn Ile Glu Glu
        35                  40                  45

Ile Arg Ile Gly Asp Val Val Arg Ser Trp Asn Glu Asn Thr Asn Thr
         50                  55                  60

Xaa Xaa Xaa Xaa Xaa Xaa Xaa Xaa Xaa Xaa Xaa Xaa Xaa Xaa
 65                  70                  75                  80
```

```
Xaa Xaa Xaa Xaa Xaa Xaa Xaa Gly Glu Glu Glu Ile His Thr Thr Trp
                85                  90                  95

Asn His Pro Phe Arg Arg Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa
            115                 120                 125

Xaa Xaa Xaa Xaa Xaa Xaa Xaa Xaa Xaa Xaa Xaa Xaa Xaa Xaa
            130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa
            165                 170                 175

Trp Val Lys Val Glu Asp Leu Arg Leu Arg Asp Gln Val Leu Arg Ser
            180                 185                 190

Asp Gly Ser Trp Gly Thr Val Thr Gly Ile Tyr Tyr Tyr Xaa Xaa Xaa
            195                 200                 205

Xaa Xaa Lys Val Tyr Asn Leu Glu Val Glu Asp Asn His Thr Tyr Val
210                 215                 220

Val Xaa Xaa Xaa Xaa Xaa Xaa Lys Gly Tyr Val Val His Asn Tyr
225                 230                 235

<210> SEQ ID NO 38
<211> LENGTH: 144
<212> TYPE: PRT
<213> ORGANISM: Gemmata obscuriglobus
<220> FEATURE:
<221> NAME/KEY: misc_feature
<222> LOCATION: (36)..(59)
<223> OTHER INFORMATION: Xaa can be any naturally occurring amino acid
<220> FEATURE:
<221> NAME/KEY: misc_feature
<222> LOCATION: (75)..(78)
<223> OTHER INFORMATION: Xaa can be any naturally occurring amino acid
<220> FEATURE:
<221> NAME/KEY: misc_feature
<222> LOCATION: (94)..(97)
<223> OTHER INFORMATION: Xaa can be any naturally occurring amino acid
<220> FEATURE:
<221> NAME/KEY: misc_feature
<222> LOCATION: (112)..(115)
<223> OTHER INFORMATION: Xaa can be any naturally occurring amino acid
<220> FEATURE:
<221> NAME/KEY: misc_feature
<222> LOCATION: (131)..(136)
<223> OTHER INFORMATION: Xaa can be any naturally occurring amino acid

<400> SEQUENCE: 38

Cys Phe Ala Ala Gly Thr Lys Leu Leu Thr Arg Arg Gly Trp Val Ala
1               5                   10                  15

Val Glu Leu Leu Gly Ile Gly Asp Glu Val Ala Ser Arg Thr Glu His
            20                  25                  30

Asp Leu Thr Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Gly Gly Glu Leu Ile
50                  55                  60

Arg Thr Thr Pro Glu His Pro Phe Trp Val Xaa Xaa Xaa Xaa Trp Thr
65                  70                  75                  80

Ala Ala Gly Ser Leu Ala Ala Gly Asp Arg Ile Ala Thr Xaa Xaa
            85                  90                  95

Xaa Leu Ser Gly Glu Trp Val Pro Ile Ala Glu Val Phe Asp Thr Xaa
            100                 105                 110
```

```
Xaa Xaa Xaa Pro Val Tyr Asn Leu Arg Val Ala Asp His His Thr Tyr
        115                 120                 125

Phe Val Xaa Xaa Xaa Xaa Xaa Phe Ala Ala Trp Ala His Asn Ala
    130                 135                 140
```

<210> SEQ ID NO 39
<211> LENGTH: 139
<212> TYPE: PRT
<213> ORGANISM: Gemmata obscuriglobus
<220> FEATURE:
<221> NAME/KEY: misc_feature
<222> LOCATION: (36)..(58)
<223> OTHER INFORMATION: Xaa can be any naturally occurring amino acid
<220> FEATURE:
<221> NAME/KEY: misc_feature
<222> LOCATION: (74)..(110)
<223> OTHER INFORMATION: Xaa can be any naturally occurring amino acid
<220> FEATURE:
<221> NAME/KEY: misc_feature
<222> LOCATION: (126)..(131)
<223> OTHER INFORMATION: Xaa can be any naturally occurring amino acid

<400> SEQUENCE: 39

```
Cys Phe Ala Ser Gly Thr Pro Met Arg Thr Pro Gly Gly Trp Cys Asn
1               5                   10                  15

Ile Glu Asn Leu Arg Val Gly Asp Phe Val Leu Ser Arg Asp Glu Phe
            20                  25                  30

Ser Pro Glu Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Leu Gly Gln Thr Ile Arg
    50                  55                  60

Ser Thr Asp Glu His Pro Phe Phe Val Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Thr Val
                100                 105                 110

Tyr Asn Phe Arg Val Ala Asp His His Thr Tyr Phe Val Xaa Xaa Xaa
        115                 120                 125

Xaa Xaa Xaa Phe Ser Val Trp Ala His Asn Ile
    130                 135
```

<210> SEQ ID NO 40
<211> LENGTH: 132
<212> TYPE: PRT
<213> ORGANISM: Pirellula sp.
<220> FEATURE:
<221> NAME/KEY: misc_feature
<222> LOCATION: (36)..(57)
<223> OTHER INFORMATION: Xaa can be any naturally occurring amino acid
<220> FEATURE:
<221> NAME/KEY: misc_feature
<222> LOCATION: (73)..(76)
<223> OTHER INFORMATION: Xaa can be any naturally occurring amino acid
<220> FEATURE:
<221> NAME/KEY: misc_feature
<222> LOCATION: (92)..(107)
<223> OTHER INFORMATION: Xaa can be any naturally occurring amino acid
<220> FEATURE:
<221> NAME/KEY: misc_feature
<222> LOCATION: (123)..(124)
<223> OTHER INFORMATION: Xaa can be any naturally occurring amino acid

<400> SEQUENCE: 40

```
Cys Leu Val Ala Gly Thr Leu Val Trp Thr Asp Arg Gly Met Arg Pro
1               5                   10                  15
```

```
Val Glu Ser Leu Arg Leu Gly Asp Gln Val Leu Ser Cys Asp Val Gln
             20                  25                  30

Thr Gly Ser Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Gly Ser Asp Glu Ile Val Ala
     50                  55                  60

Ser Lys Gly His Pro Phe Trp Val Xaa Xaa Xaa Trp Thr Thr Thr
 65                  70                  75                  80

Glu Gln Leu Val Pro Gly Asp Ala Leu His Gly Xaa Xaa Xaa Xaa
                 85                  90                  95

Xaa Xaa Xaa Xaa Xaa Xaa Xaa Xaa Xaa Xaa Lys Thr Tyr Asn Leu
         100                 105                 110

Val Val Glu Gln Thr His Ser Tyr Phe Val Xaa Xaa Ser Arg Ile Leu
             115                 120                 125

Ser His Asp Ala
         130
```

<210> SEQ ID NO 41
<211> LENGTH: 144
<212> TYPE: PRT
<213> ORGANISM: Streptomyces avermitilis
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (37)..(64)
<223> OTHER INFORMATION: Xaa can be any naturally occurring amino acid
<220> FEATURE:
<221> NAME/KEY: misc_feature
<222> LOCATION: (80)..(84)
<223> OTHER INFORMATION: Xaa can be any naturally occurring amino acid
<220> FEATURE:
<221> NAME/KEY: misc_feature
<222> LOCATION: (114)..(117)
<223> OTHER INFORMATION: Xaa can be any naturally occurring amino acid
<220> FEATURE:
<221> NAME/KEY: misc_feature
<222> LOCATION: (133)..(136)
<223> OTHER INFORMATION: Xaa can be any naturally occurring amino acid

<400> SEQUENCE: 41

```
Ser Phe Lys Pro Thr Thr Arg Val Leu Met Lys Asp Gly Xaa Thr Lys
 1               5                  10                  15

Pro Leu Gly Lys Ile Lys Pro Gly Asp Leu Val Glu Ala Ala Asp Pro
             20                  25                  30

Thr Ser Gly His Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Xaa Xaa Xaa
     50                  55                  60

Arg Ile Gln Thr Leu His Thr Thr Ala Arg His Arg Ile Trp Asp Xaa
 65                  70                  75                  80

Xaa Xaa Xaa Xaa Trp Glu Gln Ala Gly Arg Leu Ile Thr Gly His Lys
                 85                  90                  95

Val Asn Thr Ser Gly Asn Gln His Ala Thr Ile Thr Ser Val Leu Ala
             100                 105                 110

Gln Xaa Xaa Xaa Xaa Asp Met Tyr Asp Leu Thr Val Glu Gly Leu His
         115                 120                 125

Thr Tyr Tyr Val Xaa Xaa Xaa Xaa Thr Pro Val Leu Val His Asn Gly
     130                 135                 140
```

```
<210> SEQ ID NO 42
<211> LENGTH: 143
<212> TYPE: PRT
<213> ORGANISM: Streptomyces avermitilis
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (37)..(63)
<223> OTHER INFORMATION: Xaa can be any naturally occurring amino acid
<220> FEATURE:
<221> NAME/KEY: misc_feature
<222> LOCATION: (79)..(83)
<223> OTHER INFORMATION: Xaa can be any naturally occurring amino acid
<220> FEATURE:
<221> NAME/KEY: misc_feature
<222> LOCATION: (113)..(116)
<223> OTHER INFORMATION: Xaa can be any naturally occurring amino acid
<220> FEATURE:
<221> NAME/KEY: misc_feature
<222> LOCATION: (132)..(135)
<223> OTHER INFORMATION: Xaa can be any naturally occurring amino acid

<400> SEQUENCE: 42

Cys Phe Leu Ala Gly Thr Asp Ile Leu Met Ala Asp Gly Xaa Thr Lys
1               5                   10                  15

Asp Ile Glu Glu Val Glu Leu Gly Asp Lys Val Gln Ala Thr Asp Pro
            20                  25                  30

Lys Thr Gly Glu Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Gly
    50                  55                  60

Ala Glu Glu Leu Thr Ala Thr His Glu His Pro Phe Trp Ser Xaa Xaa
65                  70                  75                  80

Xaa Xaa Xaa Trp Ile Thr Ala Gly Ser Leu Glu Pro Gly Met Thr Leu
                85                  90                  95

Leu Thr Asp Asp Gly Asp Thr Val Ile Val Thr Gly Asn Arg Ala Phe
            100                 105                 110

Xaa Xaa Xaa Xaa Thr Thr Tyr Asn Leu Thr Val Asn Asp Leu His Thr
        115                 120                 125

Tyr Tyr Ala Xaa Xaa Xaa Xaa Thr Pro Val Leu Val His Asn Ser
    130                 135                 140

<210> SEQ ID NO 43
<211> LENGTH: 146
<212> TYPE: PRT
<213> ORGANISM: Streptomyces avermitilis
<220> FEATURE:
<221> NAME/KEY: misc_feature
<222> LOCATION: (14)..(15)
<223> OTHER INFORMATION: Xaa can be any naturally occurring amino acid
<220> FEATURE:
<221> NAME/KEY: misc_feature
<222> LOCATION: (38)..(66)
<223> OTHER INFORMATION: Xaa can be any naturally occurring amino acid
<220> FEATURE:
<221> NAME/KEY: misc_feature
<222> LOCATION: (82)..(86)
<223> OTHER INFORMATION: Xaa can be any naturally occurring amino acid
<220> FEATURE:
<221> NAME/KEY: misc_feature
<222> LOCATION: (116)..(119)
<223> OTHER INFORMATION: Xaa can be any naturally occurring amino acid
<220> FEATURE:
<221> NAME/KEY: misc_feature
```

```
<222> LOCATION: (135)..(138)
<223> OTHER INFORMATION: Xaa can be any naturally occurring amino acid

<400> SEQUENCE: 43

Ser Phe Pro Ala Gly Thr Arg Val Leu Met Gly Asp Gly Xaa Xaa Thr
1               5                   10                  15

Leu Pro Ile Glu Gln Ile Thr Val Gly Asp Ser Val Leu Ala Thr Asp
            20                  25                  30

Pro Glu Ala Gly Thr Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Gly Pro Pro Ala Leu Thr Ala Thr Asp Arg His Pro Phe Trp
65                  70                  75                  80

Val Xaa Xaa Xaa Xaa Xaa Trp Ala Asp Ala Arg Asp Leu Asn Ser Gly
                85                  90                  95

Asp Thr Leu Arg Thr Pro Asp Gly Thr Gly Val Arg Ile Asp Lys Val
            100                 105                 110

Thr His Trp Xaa Xaa Xaa Xaa Gly Ala Tyr Asn Leu Thr Val Asn Asp
            115                 120                 125

Leu His Thr Tyr Tyr Val Xaa Xaa Xaa Xaa Val Pro Val Leu Val His
    130                 135                 140

Asn Ala
145

<210> SEQ ID NO 44
<211> LENGTH: 129
<212> TYPE: PRT
<213> ORGANISM: Myxococcus xanthus
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (37)..(58)
<223> OTHER INFORMATION: Xaa can be any naturally occurring amino acid
<220> FEATURE:
<221> NAME/KEY: misc_feature
<222> LOCATION: (74)..(106)
<223> OTHER INFORMATION: Xaa can be any naturally occurring amino acid

<400> SEQUENCE: 44

Cys Val Ala Pro Trp Glu Leu Val Leu Leu Gly Asp Gly Xaa Glu Val
1               5                   10                  15

Pro Ala Glu Met Leu Arg Pro Gly Met Arg Val Leu Thr Met His Glu
            20                  25                  30

His Glu Arg Asp Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Asp Gly Arg Val Leu Val
    50                  55                  60

Val Thr Pro Asp His Arg Trp Arg Thr Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Asp Val Met Arg Ile Thr
            100                 105                 110

Val Arg Phe Ala Met Thr Tyr Ile Val Gln Gly Leu Leu Ala His Asn
            115                 120                 125
```

Leu

<210> SEQ ID NO 45
<211> LENGTH: 131
<212> TYPE: PRT
<213> ORGANISM: Myxococcus xanthus
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (37)..(58)
<223> OTHER INFORMATION: Xaa can be any naturally occurring amino acid
<220> FEATURE:
<221> NAME/KEY: misc_feature
<222> LOCATION: (74)..(108)
<223> OTHER INFORMATION: Xaa can be any naturally occurring amino acid

<400> SEQUENCE: 45

Cys Val Ala Pro Trp Glu Pro Val Leu Leu Ser Asp Gly Xaa Glu Val
1               5                   10                  15

Pro Ala Glu Met Leu Arg Pro Gly Met Lys Val Leu Thr Met His Glu
            20                  25                  30

His Glu Arg Asp Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Asp Gly Arg Ala Val Val
    50                  55                  60

Val Thr Pro Asp His Arg Trp Arg Thr Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Asp Val Met Lys
                100                 105                 110

Ile Ser Val Arg Phe Ala Lys Thr Tyr Val Val Gln Gly Leu Leu Ala
        115                 120                 125

His Asn Leu
    130

<210> SEQ ID NO 46
<211> LENGTH: 137
<212> TYPE: PRT
<213> ORGANISM: Verrucomicrobium spinosum
<220> FEATURE:
<221> NAME/KEY: misc_feature
<222> LOCATION: (36)..(57)
<223> OTHER INFORMATION: Xaa can be any naturally occurring amino acid
<220> FEATURE:
<221> NAME/KEY: misc_feature
<222> LOCATION: (73)..(77)
<223> OTHER INFORMATION: Xaa can be any naturally occurring amino acid
<220> FEATURE:
<221> NAME/KEY: misc_feature
<222> LOCATION: (107)..(112)
<223> OTHER INFORMATION: Xaa can be any naturally occurring amino acid
<220> FEATURE:
<221> NAME/KEY: misc_feature
<222> LOCATION: (128)..(129)
<223> OTHER INFORMATION: Xaa can be any naturally occurring amino acid

<400> SEQUENCE: 46

Cys Phe Pro Ser Gly Thr Met Val Gln Thr Ala Arg Gly Lys Val Ala
1               5                   10                  15

Ile Glu Thr Leu Lys Glu Gly Asp Val Val Leu Ala Tyr Asp Phe Leu
            20                  25                  30

```
Ser Glu Cys Xaa Xaa Xaa Xaa Xaa Xaa Xaa Xaa Xaa Xaa Xaa
        35                  40                  45

Xaa Xaa Xaa Xaa Xaa Xaa Xaa Xaa Gly Asp Ser Lys Ile Ser Ala
    50                  55                  60

Thr Arg Phe His Leu Phe Trp Val Xaa Xaa Xaa Xaa Trp Val Pro
 65              70                  75                  80

Ala Val Asp Leu Gln Pro Gly Met Val Leu Arg Leu Glu Ser Gly Ala
                 85                  90                  95

Leu Thr Val Val Thr Leu Ala Lys Leu Arg Xaa Xaa Xaa Xaa Xaa
            100                 105                 110

Ala Thr His Asn Phe Glu Val Ala Asp Leu His Asn Tyr Phe Val Xaa
            115                 120                 125

Xaa Gln Gly Phe Leu Val His Asn Gly
            130                 135

<210> SEQ ID NO 47
<211> LENGTH: 140
<212> TYPE: PRT
<213> ORGANISM: Verrucomicrobium spinosum
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (37)..(60)
<223> OTHER INFORMATION: Xaa can be any naturally occurring amino acid
<220> FEATURE:
<221> NAME/KEY: misc_feature
<222> LOCATION: (76)..(79)
<223> OTHER INFORMATION: Xaa can be any naturally occurring amino acid
<220> FEATURE:
<221> NAME/KEY: misc_feature
<222> LOCATION: (95)..(113)
<223> OTHER INFORMATION: Xaa can be any naturally occurring amino acid
<220> FEATURE:
<221> NAME/KEY: misc_feature
<222> LOCATION: (129)..(132)
<223> OTHER INFORMATION: Xaa can be any naturally occurring amino acid

<400> SEQUENCE: 47

Cys Phe Pro Ala Gly Thr Met Val Leu Met Ala Asp Gly Xaa Ser Val
 1               5                  10                  15

Pro Ile Glu Gln Val Val Glu Gly Asp Ile Val Leu Ala Ala Glu Pro
                 20                  25                  30

Glu Thr Glu Ser Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Thr Gly Ser Val
    50                  55                  60

Leu Lys Val Thr Gly Glu His Pro Ile Trp Thr Xaa Xaa Xaa Xaa Trp
 65              70                  75                  80

Gln His Ala Asp Asp Leu Val Glu Gly Asp Leu Leu Leu Lys Xaa Xaa
                 85                  90                  95

Xaa Xaa Xaa Xaa Xaa Xaa Xaa Xaa Xaa Xaa Xaa Xaa Xaa Xaa Xaa
            100                 105                 110

Xaa Asp Thr Phe Asn Leu Cys Val Glu Gly Val His Thr Phe Tyr Val
            115                 120                 125

Xaa Xaa Xaa Xaa Asp Ala Val Leu Val His Asn Thr
            130                 135                 140

<210> SEQ ID NO 48
<211> LENGTH: 145
```

-continued

```
<212> TYPE: PRT
<213> ORGANISM: Verrucomicrobium spinosum
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (37)..(66)
<223> OTHER INFORMATION: Xaa can be any naturally occurring amino acid
<220> FEATURE:
<221> NAME/KEY: misc_feature
<222> LOCATION: (82)..(85)
<223> OTHER INFORMATION: Xaa can be any naturally occurring amino acid
<220> FEATURE:
<221> NAME/KEY: misc_feature
<222> LOCATION: (101)..(118)
<223> OTHER INFORMATION: Xaa can be any naturally occurring amino acid
<220> FEATURE:
<221> NAME/KEY: misc_feature
<222> LOCATION: (134)..(137)
<223> OTHER INFORMATION: Xaa can be any naturally occurring amino acid

<400> SEQUENCE: 48

Cys Phe Ala Pro Gly Thr Pro Val Leu Met Gly Asp Gly Xaa Thr Arg
1               5                   10                  15

Pro Val Glu Thr Ile Arg Glu Gly Asp Trp Ile Met Ala Asp Asp Pro
            20                  25                  30

Glu Asp Glu Arg Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Pro Asp Gly Ala Leu Lys Ala Thr Gly Gly His Pro Phe Trp
65                  70                  75                  80

Thr Xaa Xaa Xaa Xaa Trp Ile Lys Val Cys Asn Leu Gln Pro Asn Asp
                85                  90                  95

Ile Leu Ala Asp Xaa Xaa Xaa Xaa Xaa Xaa Xaa Xaa Xaa Xaa Xaa Xaa
            100                 105                 110

Xaa Xaa Xaa Xaa Xaa Xaa Ala Thr Tyr Asn Leu Ser Val Ala Asn Ile
        115                 120                 125

His Thr Phe Phe Val Xaa Xaa Xaa Xaa Val Pro Val Leu Val His Asn
    130                 135                 140

Thr
145

<210> SEQ ID NO 49
<211> LENGTH: 141
<212> TYPE: PRT
<213> ORGANISM: Gloeobacter violaceus
<220> FEATURE:
<221> NAME/KEY: misc_feature
<222> LOCATION: (36)..(64)
<223> OTHER INFORMATION: Xaa can be any naturally occurring amino acid
<220> FEATURE:
<221> NAME/KEY: misc_feature
<222> LOCATION: (80)..(83)
<223> OTHER INFORMATION: Xaa can be any naturally occurring amino acid
<220> FEATURE:
<221> NAME/KEY: misc_feature
<222> LOCATION: (113)..(116)
<223> OTHER INFORMATION: Xaa can be any naturally occurring amino acid
<220> FEATURE:
<221> NAME/KEY: misc_feature
<222> LOCATION: (132)..(133)
<223> OTHER INFORMATION: Xaa can be any naturally occurring amino acid

<400> SEQUENCE: 49
```

Cys Phe Ala Glu Gly Thr Glu Val Gln Thr Glu Thr Gly Thr Lys Ala
1               5                   10                  15

Ile Glu Lys Val Glu Pro Gly Glu Lys Val Leu Ala Arg Asn Glu Lys
                20                  25                  30

Thr Gly Glu Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa Xaa
    50                  55                  60

Glu Arg Asp Thr Leu Thr Val Thr Gly Glu His Pro Phe Phe Leu Xaa
65                  70                  75                  80

Xaa Xaa Xaa Trp Thr Ala Ala Glu Arg Leu Arg Ser Gly Glu Arg Val
                85                  90                  95

Gln Ala Val Asp Gly Lys Trp Leu Arg Val Gly Leu Gln Pro Gln
                100                 105                 110

Xaa Xaa Xaa Xaa Arg Thr Tyr Asn Leu Glu Val Glu Gly Glu His Thr
            115                 120                 125

Phe Phe Val Xaa Xaa Thr Arg Ala Trp Val His Asn Glu
130                 135                 140

<210> SEQ ID NO 50
<211> LENGTH: 141
<212> TYPE: PRT
<213> ORGANISM: Gloeobacter violaceus
<220> FEATURE:
<221> NAME/KEY: misc_feature
<222> LOCATION: (36)..(64)
<223> OTHER INFORMATION: Xaa can be any naturally occurring amino acid
<220> FEATURE:
<221> NAME/KEY: misc_feature
<222> LOCATION: (80)..(83)
<223> OTHER INFORMATION: Xaa can be any naturally occurring amino acid
<220> FEATURE:
<221> NAME/KEY: misc_feature
<222> LOCATION: (113)..(116)
<223> OTHER INFORMATION: Xaa can be any naturally occurring amino acid
<220> FEATURE:
<221> NAME/KEY: misc_feature
<222> LOCATION: (132)..(133)
<223> OTHER INFORMATION: Xaa can be any naturally occurring amino acid

<400> SEQUENCE: 50

Cys Phe Ala Glu Gly Thr Glu Val Gln Thr Glu Thr Gly Ala Lys Pro
1               5                   10                  15

Ile Glu Leu Val Ala Pro Gly Glu Lys Val Leu Ala Arg Asn Glu Gln
                20                  25                  30

Thr Gly Glu Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa Xaa
    50                  55                  60

Asp Arg Asp Val Leu Thr Val Thr Gly Glu His Pro Phe Phe Leu Xaa
65                  70                  75                  80

Xaa Xaa Xaa Trp Thr Ala Ala Asp Lys Leu Gln Val Gly Glu Arg Val
                85                  90                  95

Gln Thr Val Asp Gly Gln Trp Leu Arg Val Ala Gly Leu Gln Ala Gln
                100                 105                 110

Xaa Xaa Xaa Xaa Arg Thr Tyr Asn Leu Glu Val Glu Arg Asp His Thr
            115                 120                 125

Phe Phe Val Xaa Xaa Ser Lys Ala Trp Val His Asn Glu
130                 135                 140

```
<210> SEQ ID NO 51
<211> LENGTH: 141
<212> TYPE: PRT
<213> ORGANISM: Gloeobacter violaceus
<220> FEATURE:
<221> NAME/KEY: misc_feature
<222> LOCATION: (36)..(64)
<223> OTHER INFORMATION: Xaa can be any naturally occurring amino acid
<220> FEATURE:
<221> NAME/KEY: misc_feature
<222> LOCATION: (80)..(83)
<223> OTHER INFORMATION: Xaa can be any naturally occurring amino acid
<220> FEATURE:
<221> NAME/KEY: misc_feature
<222> LOCATION: (113)..(116)
<223> OTHER INFORMATION: Xaa can be any naturally occurring amino acid
<220> FEATURE:
<221> NAME/KEY: misc_feature
<222> LOCATION: (132)..(133)
<223> OTHER INFORMATION: Xaa can be any naturally occurring amino acid

<400> SEQUENCE: 51

Cys Phe Ser Glu Gly Thr Glu Val Gln Thr Glu Ala Gly Ala Lys Pro
1               5                   10                  15

Ile Glu Leu Val Glu Pro Gly Glu Lys Val Leu Ala Arg Asn Glu Gln
            20                  25                  30

Thr Gly Glu Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Glu Arg Asp Thr Leu Thr Val Thr Gly Glu His Pro Phe Phe Leu Xaa
65                  70                  75                  80

Xaa Xaa Xaa Trp Thr Ala Ala Glu Arg Leu Lys Ser Gly Glu Arg Val
                85                  90                  95

Gln Ala Ala Asp Gly Lys Trp Leu Arg Val Ala Gly Leu Glu Ala Gln
            100                 105                 110

Xaa Xaa Xaa Xaa Arg Thr Tyr Asn Leu Glu Val Glu Gly Asp His Thr
        115                 120                 125

Phe Phe Val Xaa Xaa Asn Gln Ala Trp Val His Asn Glu
    130                 135                 140

<210> SEQ ID NO 52
<211> LENGTH: 139
<212> TYPE: PRT
<213> ORGANISM: Chromobacterium violaceum
<220> FEATURE:
<221> NAME/KEY: misc_feature
<222> LOCATION: (36)..(62)
<223> OTHER INFORMATION: Xaa can be any naturally occurring amino acid
<220> FEATURE:
<221> NAME/KEY: misc_feature
<222> LOCATION: (78)..(81)
<223> OTHER INFORMATION: Xaa can be any naturally occurring amino acid
<220> FEATURE:
<221> NAME/KEY: misc_feature
<222> LOCATION: (97)..(114)
<223> OTHER INFORMATION: Xaa can be any naturally occurring amino acid
<220> FEATURE:
<221> NAME/KEY: misc_feature
<222> LOCATION: (130)..(131)
<223> OTHER INFORMATION: Xaa can be any naturally occurring amino acid

<400> SEQUENCE: 52

Cys Phe Val Ala Gly Thr Gln Val Leu Thr Asp Lys Gly Leu Lys Ala
1               5                   10                  15

Ile Glu Thr Phe Val Gly Gly Glu Trp Val Trp Ser Arg Ser Asp Gln
            20                  25                  30
```

Thr Gly Glu Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Arg Gln
        50                  55                  60

Glu Thr Phe Arg Thr Thr Ala Glu His Pro Phe Trp Val Xaa Xaa
65                  70                  75                  80

Xaa Trp Leu Lys Ala Ser Leu Leu Gln Ala Gly Val Ile Leu Val Asp
            85                  90                  95

Xaa Xaa Xaa Xaa Xaa Xaa Xaa Xaa Xaa Xaa Xaa Xaa Xaa Xaa
            100                 105                 110

Xaa Xaa Thr Val Phe Asn Ile Gln Val Ala Glu Phe Gln Thr Tyr His
        115                 120                 125

Val Xaa Xaa Leu Gly Val Trp Val His Asn Ala
        130                 135

<210> SEQ ID NO 53
<211> LENGTH: 141
<212> TYPE: PRT
<213> ORGANISM: Gloeobacter violaceus
<220> FEATURE:
<221> NAME/KEY: misc_feature
<222> LOCATION: (36)..(64)
<223> OTHER INFORMATION: Xaa can be any naturally occurring amino acid
<220> FEATURE:
<221> NAME/KEY: misc_feature
<222> LOCATION: (80)..(83)
<223> OTHER INFORMATION: Xaa can be any naturally occurring amino acid
<220> FEATURE:
<221> NAME/KEY: misc_feature
<222> LOCATION: (113)..(116)
<223> OTHER INFORMATION: Xaa can be any naturally occurring amino acid
<220> FEATURE:
<221> NAME/KEY: misc_feature
<222> LOCATION: (132)..(133)
<223> OTHER INFORMATION: Xaa can be any naturally occurring amino acid

<400> SEQUENCE: 53

Cys Phe Ala Glu Gly Thr Glu Val Gln Thr Glu Thr Gly Thr Lys Ala
1               5                   10                  15

Ile Glu Lys Val Glu Pro Gly Glu Lys Val Leu Ala Arg Asn Glu Lys
                20                  25                  30

Thr Gly Glu Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa
        50                  55                  60

Glu Arg Asp Thr Leu Thr Val Thr Gly Glu His Pro Phe Phe Leu Xaa
65                  70                  75                  80

Xaa Xaa Xaa Trp Thr Ala Ala Asp Lys Leu Gln Ala Gly Asp Arg Val
            85                  90                  95

Gln Ala Val Asp Gly Arg Trp Leu Arg Val Val Gly Leu Ala Ala Gln
            100                 105                 110

Xaa Xaa Xaa Xaa Arg Thr Tyr Asn Leu Glu Ile Glu Gly Glu His Thr
        115                 120                 125

Phe Phe Val Xaa Xaa Asn Gln Ala Trp Val His Asn Glu
        130                 135                 140

<210> SEQ ID NO 54
<211> LENGTH: 93
<212> TYPE: PRT
<213> ORGANISM: Gloeobacter violaceus
<220> FEATURE:

```
<221> NAME/KEY: misc_feature
<222> LOCATION: (36)..(78)
<223> OTHER INFORMATION: Xaa can be any naturally occurring amino acid

<400> SEQUENCE: 54

Cys Phe Gly Glu Gly Thr Ala Val Gln Thr Glu Thr Arg Ala Lys Pro
1               5                   10                  15

Ile Glu Gln Ile Glu Pro Gly Glu Lys Val Leu Ala Arg Ser Glu Arg
            20                  25                  30

Thr Gly Gln Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Glu Arg
65                  70                  75                  80

Asp Thr Ser Thr Val Thr Gly Glu His Pro Phe Tyr Leu
                85                  90

<210> SEQ ID NO 55
<211> LENGTH: 81
<212> TYPE: PRT
<213> ORGANISM: Neisseria meningitidis (group C)
<220> FEATURE:
<221> NAME/KEY: misc_feature
<222> LOCATION: (16)..(18)
<223> OTHER INFORMATION: Xaa can be any naturally occurring amino acid
<220> FEATURE:
<221> NAME/KEY: misc_feature
<222> LOCATION: (48)..(51)
<223> OTHER INFORMATION: Xaa can be any naturally occurring amino acid
<220> FEATURE:
<221> NAME/KEY: misc_feature
<222> LOCATION: (67)..(73)
<223> OTHER INFORMATION: Xaa can be any naturally occurring amino acid

<400> SEQUENCE: 55

Asn Ser Gln Ile Leu Ile Ser Asn Arg Ile His Pro Phe Tyr Ser Xaa
1               5                   10                  15

Xaa Xaa Trp Ile Lys Ala Glu Asp Leu Lys Ala Gly Ser Arg Leu Leu
            20                  25                  30

Ser Glu Ser Gly Lys Thr Gln Thr Val Arg Asn Ile Val Val Lys Xaa
        35                  40                  45

Xaa Xaa Xaa Lys Ala Tyr Asn Leu Thr Val Ala Asp Trp His Thr Tyr
    50                  55                  60

Phe Val Xaa Xaa Xaa Xaa Xaa Xaa Xaa Xaa Glu Gly Val Trp Val His Asn
65                  70                  75                  80

Asp

<210> SEQ ID NO 56
<211> LENGTH: 91
<212> TYPE: PRT
<213> ORGANISM: Clostridium thermocellum
<220> FEATURE:
<221> NAME/KEY: misc_feature
<222> LOCATION: (36)..(57)
<223> OTHER INFORMATION: Xaa can be any naturally occurring amino acid
<220> FEATURE:
<221> NAME/KEY: misc_feature
<222> LOCATION: (73)..(76)
<223> OTHER INFORMATION: Xaa can be any naturally occurring amino acid

<400> SEQUENCE: 56

Cys Phe Val Ala Gly Thr Met Ile Leu Thr Ala Thr Gly Leu Val Ala
1               5                   10                  15
```

```
Ile Glu Asn Ile Lys Ala Gly Asp Lys Val Ile Ala Thr Asn Pro Glu
        20                  25                  30

Thr Phe Glu Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Asn Gly Glu Val Ile Lys Thr
    50                  55                  60

Thr Phe Glu His Pro Phe Tyr Val Xaa Xaa Xaa Phe Val Glu Ala
65                  70                  75                  80

Gly Lys Leu Gln Ile Gly Asp Arg Leu Val Asp
                85                  90

<210> SEQ ID NO 57
<211> LENGTH: 45
<212> TYPE: PRT
<213> ORGANISM: Clostridium thermocellum
<220> FEATURE:
<221> NAME/KEY: misc_feature
<222> LOCATION: (15)..(20)
<223> OTHER INFORMATION: Xaa can be any naturally occurring amino acid
<220> FEATURE:
<221> NAME/KEY: misc_feature
<222> LOCATION: (36)..(37)
<223> OTHER INFORMATION: Xaa can be any naturally occurring amino acid

<400> SEQUENCE: 57

Ser Lys Gly Asn Val Leu Val Val Glu Glu Lys Lys Leu Glu Xaa Xaa
1               5                   10                  15

Xaa Xaa Xaa Xaa Lys Val Tyr Asn Phe Lys Val Asn Asp Phe His Thr
            20                  25                  30

Tyr His Val Xaa Xaa Asp Gly Ile Leu Val His Asn Ala
        35                  40                  45

<210> SEQ ID NO 58
<211> LENGTH: 24
<212> TYPE: PRT
<213> ORGANISM: Clostridium thermocellum
<220> FEATURE:
<221> NAME/KEY: misc_feature
<222> LOCATION: (15)..(16)
<223> OTHER INFORMATION: Xaa can be any naturally occurring amino acid

<400> SEQUENCE: 58

Val Tyr Asn Phe Lys Val Asp Asn Phe His Thr Tyr His Val Xaa Xaa
1               5                   10                  15

Asn Arg Val Leu Val His Asn Ala
            20

<210> SEQ ID NO 59
<211> LENGTH: 39
<212> TYPE: PRT
<213> ORGANISM: Clostridium thermocellum
<220> FEATURE:
<221> NAME/KEY: misc_feature
<222> LOCATION: (16)..(34)
<223> OTHER INFORMATION: Xaa can be any naturally occurring amino acid

<400> SEQUENCE: 59

Phe Val Lys Glu Met Lys Leu Gln Pro Gly Asn Arg Leu Val Asp Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Lys Val Tyr Asn Phe
        35
```

```
<210> SEQ ID NO 60
<211> LENGTH: 63
<212> TYPE: PRT
<213> ORGANISM: Leptospira interrogans
<220> FEATURE:
<221> NAME/KEY: misc_feature
<222> LOCATION: (30)..(34)
<223> OTHER INFORMATION: Xaa can be any naturally occurring amino acid
<220> FEATURE:
<221> NAME/KEY: misc_feature
<222> LOCATION: (50)..(55)
<223> OTHER INFORMATION: Xaa can be any naturally occurring amino acid

<400> SEQUENCE: 60

Trp Val Lys Val Glu Asp Leu Arg Leu Arg Asp Gln Val Leu Arg Ser
1               5                   10                  15

Asp Gly Ser Trp Gly Thr Val Thr Gly Ile Tyr Tyr Tyr Xaa Xaa Xaa
            20                  25                  30

Xaa Xaa Lys Val Tyr Asn Leu Glu Val Glu Asp Asn His Thr Tyr Ile
        35                  40                  45

Val Xaa Xaa Xaa Xaa Xaa Xaa Ile Gly Tyr Val Val His Asn Tyr
    50                  55                  60

<210> SEQ ID NO 61
<211> LENGTH: 10
<212> TYPE: PRT
<213> ORGANISM: Gloeobacter violaceus

<400> SEQUENCE: 61

Cys Phe Ala Glu Gly Thr Glu Val Gln Thr
1               5                   10

<210> SEQ ID NO 62
<211> LENGTH: 15
<212> TYPE: PRT
<213> ORGANISM: Gloeobacter violaceus

<400> SEQUENCE: 62

Trp Thr Ala Ala Glu Arg Leu Glu Pro Gly Asp Arg Val Gln Ala
1               5                   10                  15

<210> SEQ ID NO 63
<211> LENGTH: 153
<212> TYPE: PRT
<213> ORGANISM: Rhodobacter capsulatus
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(56)
<223> OTHER INFORMATION: Xaa can be any naturally occurring amino acid
<220> FEATURE:
<221> NAME/KEY: misc_feature
<222> LOCATION: (67)..(80)
<223> OTHER INFORMATION: Xaa can be any naturally occurring amino acid
<220> FEATURE:
<221> NAME/KEY: misc_feature
<222> LOCATION: (95)..(106)
<223> OTHER INFORMATION: Xaa can be any naturally occurring amino acid
<220> FEATURE:
<221> NAME/KEY: misc_feature
<222> LOCATION: (122)..(129)
<223> OTHER INFORMATION: Xaa can be any naturally occurring amino acid

<400> SEQUENCE: 63
```

```
Cys Phe Thr Pro Gly Thr Leu Ile Asp Thr Pro Ala Gly Pro Arg Pro
1               5                   10                  15

Val Glu Ala Leu Arg Pro Gly Asp Arg Val Ser Thr Arg Asp Xaa Xaa
            20                  25                  30

Xaa Gln Glu Ile Leu Trp Ile Gly Ser Arg Arg Met Xaa Xaa Xaa Xaa
        35                  40                  45

Xaa Xaa Xaa Xaa Xaa Xaa Xaa Pro Val Arg Leu Gly Ala Val Arg
50                      55                  60

Leu Gly Xaa Xaa Xaa Xaa Xaa Xaa Xaa Xaa Xaa Xaa Xaa Xaa
65                  70                  75                  80

Ala Ala Asp Leu Leu Val Ser Pro Gln His Arg Val Leu Val Xaa
                85                  90                  95

Xaa Xaa Xaa Xaa Xaa Xaa Xaa Xaa Xaa Glu Val Leu Val Gln Ala
            100                 105                 110

Cys Asp Leu Val Asp Asp Ala Ala Val Xaa Xaa Xaa Xaa Xaa Xaa
            115                 120                 125

Xaa Val Thr Tyr Leu His Leu Leu Phe Ala Arg His Gln Val Ile Arg
    130                 135                 140

Ala Asn Gly Val Glu Thr Glu Ser Phe
145                 150

<210> SEQ ID NO 64
<211> LENGTH: 141
<212> TYPE: PRT
<213> ORGANISM: Rhodobacter capsulatus
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(56)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (82)..(93)
<223> OTHER INFORMATION: Xaa can be any naturally occurring amino acid
<220> FEATURE:
<221> NAME/KEY: misc_feature
<222> LOCATION: (109)..(116)
<223> OTHER INFORMATION: Xaa can be any naturally occurring amino acid
<220> FEATURE:
<221> NAME/KEY: misc_feature
<222> LOCATION: (134)..(134)
<223> OTHER INFORMATION: Xaa can be any naturally occurring amino acid

<400> SEQUENCE: 64

Gly Phe Tyr Gly Glu Thr Val Leu Gln Thr Ala Arg Gly Leu Arg Arg
1               5                   10                  15

Val Ser Ser Ile Leu Glu Gly Glu Lys Met Arg Thr Phe Thr Xaa Xaa
            20                  25                  30

Xaa Ala Pro Val Leu Ser Ile Glu Arg Phe Ala Leu Xaa Xaa Xaa Xaa
        35                  40                  45

Xaa Xaa Xaa Xaa Xaa Xaa Xaa Xaa Pro Leu Ser Leu Pro Ala Gly Leu
50                      55                  60

Phe Gly Xaa Thr Arg Asn Arg Phe Val Ala Pro Glu Gln Cys Leu Leu
65                  70                  75                  80

Leu Xaa Xaa Xaa Xaa Xaa Xaa Xaa Xaa Xaa Xaa Xaa Leu Leu Leu
            85                  90                  95
```

-continued

```
Val Pro Ala Lys Val Leu Gly Leu Leu Pro Gln Val Xaa Xaa Xaa Xaa
                100                 105                 110

Xaa Xaa Xaa Xaa Ala Val Leu Tyr Arg Leu Leu Phe Glu Arg Pro Glu
        115                 120                 125

Leu Val Val Thr Asp Xaa Gly Ala Val Met Leu Cys Asp
    130                 135                 140

<210> SEQ ID NO 65
<211> LENGTH: 134
<212> TYPE: PRT
<213> ORGANISM: Rhodobacter capsulatus
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(51)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (77)..(88)
<223> OTHER INFORMATION: Xaa can be any naturally occurring amino acid
<220> FEATURE:
<221> NAME/KEY: misc_feature
<222> LOCATION: (104)..(110)
<223> OTHER INFORMATION: Xaa can be any naturally occurring amino acid

<400> SEQUENCE: 65

Gly Phe Ala Ala Gly Thr Arg Val Arg Thr Pro Ala Gly Leu Arg Arg
1               5                   10                  15

Ile Glu Thr Leu Lys Pro Gly Asp Leu Val Glu Thr Gln Glu Xaa Xaa
                20                  25                  30

Xaa Gln Pro Val Val Ala Val Glu Arg Thr Arg Leu Xaa Xaa Xaa Xaa
        35                  40                  45

Xaa Xaa Xaa Pro Ile Arg Phe Ala Ala Gly Ala His Gly Xaa Glu Arg
    50                  55                  60

Pro Val Leu Val Ala Pro Gln Gln Arg Val Leu Val Xaa Xaa Xaa Xaa
65                  70                  75                  80

Xaa Xaa Xaa Xaa Xaa Xaa Xaa Xaa Glu Val Leu Val Ala Ala Arg Thr
                85                  90                  95

Leu Val Asp Gly Glu Met Val Xaa Xaa Xaa Xaa Xaa Xaa Xaa Val Asp
            100                 105                 110

Tyr Val Arg Leu Val Phe Asp Cys Ala His Met Val Phe Ala Glu Gly
        115                 120                 125

Leu Ala Val Glu Cys Phe
    130

<210> SEQ ID NO 66
<211> LENGTH: 135
<212> TYPE: PRT
<213> ORGANISM: Rhodobacter capsulatus
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(51)
<223> OTHER INFORMATION: Xaa can be any naturally occurring amino acid
<220> FEATURE:
```

```
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (77)..(88)
<223> OTHER INFORMATION: Xaa can be any naturally occurring amino acid
<220> FEATURE:
<221> NAME/KEY: misc_feature
<222> LOCATION: (104)..(111)
<223> OTHER INFORMATION: Xaa can be any naturally occurring amino acid

<400> SEQUENCE: 66

Cys Phe Ala Pro Ser Thr Pro Ile Ala Thr Pro Gly Gly Asp Cys Pro
1               5                   10                  15

Ala Ala Ser Leu Lys Ala Gly Asp Leu Val Leu Thr Ala Asp Xaa Xaa
            20                  25                  30

Xaa Gln Pro Ile Leu Trp Ser Gly Arg Ile Ala Leu Xaa Xaa Xaa Xaa
        35                  40                  45

Xaa Xaa Xaa Pro Val Arg Leu Cys Ala Pro Ala Phe Gly Xaa Thr Arg
50                  55                  60

Asp Leu Trp Val Leu Pro Gln His Arg Val Ala Leu Xaa Xaa Xaa Xaa
65                  70                  75                  80

Xaa Xaa Xaa Xaa Xaa Xaa Xaa Xaa Glu Val Leu Val Pro Ala His His
            85                  90                  95

Leu Val Asp Gly Ile Ser Ala Xaa Xaa Xaa Xaa Xaa Xaa Xaa Xaa Leu
            100                 105                 110

Ser Trp His Gly Leu Leu Leu Gln Gly His His Leu Leu Ile Ala Asp
        115                 120                 125

Gly Cys Arg Val Glu Ser Leu
        130                 135

<210> SEQ ID NO 67
<211> LENGTH: 135
<212> TYPE: PRT
<213> ORGANISM: Rhodobacter capsulatus
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(56)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (82)..(86)
<223> OTHER INFORMATION: Xaa can be any naturally occurring amino acid
<220> FEATURE:
<221> NAME/KEY: misc_feature
<222> LOCATION: (102)..(111)
<223> OTHER INFORMATION: Xaa can be any naturally occurring amino acid

<400> SEQUENCE: 67

Cys Phe Thr Ala Gly Thr Leu Ile Glu Thr Pro Arg Gly Pro Val Pro
1               5                   10                  15

Val Glu Ser Leu Arg Ala Gly Asp Leu Val Val Thr Arg Asp Xaa Xaa
            20                  25                  30

Xaa Val Pro Val Leu Trp Ser Gly Gly Arg Ser Leu Xaa Xaa Xaa Xaa
        35                  40                  45

Xaa Xaa Xaa Xaa Xaa Xaa Xaa Xaa Pro Val Ala Ile Arg Glu Asn Ala
```

```
                50                  55                  60
Leu Gly Xaa His Gly Ala Leu Leu Ser Pro Gln His Ala Val Leu
 65                  70                  75                  80

Ala Xaa Xaa Xaa Xaa Xaa Glu Arg Leu Val Arg Ala Arg His Leu Ala
                 85                  90                  95

Gly Leu Asn Asp Pro Xaa Xaa Xaa Xaa Xaa Xaa Xaa Xaa Xaa Val
                100                 105                 110

Ser Tyr His His Ile Leu Leu Glu Arg His Gly Ile Val Thr Ala Asn
            115                 120                 125

Gly Leu Ala Cys Glu Ser Leu
        130                 135

<210> SEQ ID NO 68
<211> LENGTH: 146
<212> TYPE: PRT
<213> ORGANISM: Rhodobacter capsulatus
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(59)
<223> OTHER INFORMATION: Xaa can be any naturally occurring amino acid
<220> FEATURE:
<221> NAME/KEY: misc_feature
<222> LOCATION: (70)..(73)
<223> OTHER INFORMATION: Xaa can be any naturally occurring amino acid
<220> FEATURE:
<221> NAME/KEY: misc_feature
<222> LOCATION: (88)..(99)
<223> OTHER INFORMATION: Xaa can be any naturally occurring amino acid
<220> FEATURE:
<221> NAME/KEY: misc_feature
<222> LOCATION: (115)..(122)
<223> OTHER INFORMATION: Xaa can be any naturally occurring amino acid

<400> SEQUENCE: 68

Ala Leu Ala Arg Gly Ser Val Leu Met Thr Glu Asp Gly Pro Val Ala
 1               5                  10                  15

Ile Glu Asp Leu Gln Pro Gly Gln Gly Val Leu Thr Ala Glu Xaa Xaa
                20                  25                  30

Xaa Glu Arg Val Cys Trp Ile Gly Ser Met Val Ile Xaa Xaa Xaa Xaa
            35                  40                  45

Xaa Xaa Xaa Xaa Xaa Xaa Xaa Xaa Xaa Xaa Xaa Leu Thr Arg Ile Thr
        50                  55                  60

Ala Glu Ala Phe Gly Xaa Xaa Xaa Xaa Ala Leu Asp Leu Val Leu Gly
 65                  70                  75                  80

Pro Arg Ala Arg Leu Cys Leu Xaa Xaa Xaa Xaa Xaa Xaa Xaa Xaa Xaa
                85                  90                  95

Xaa Xaa Xaa Ala Ala Asp Val Pro Ala Arg Ala Phe Leu Asp Gly Ile
            100                 105                 110

Ser Val Xaa Xaa Xaa Xaa Xaa Xaa Xaa Val Thr Val Tyr His Val
        115                 120                 125

Val Leu Glu Gln His Gly Ser Leu Arg Val Ala Gly Leu Glu Val Glu
130                 135                 140

Ala Phe
145

<210> SEQ ID NO 69
<211> LENGTH: 136
<212> TYPE: PRT
```

```
<213> ORGANISM: Rhodobacter capsulatus
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(53)
<223> OTHER INFORMATION: Xaa can be any naturally occurring amino acid
<220> FEATURE:
<221> NAME/KEY: misc_feature
<222> LOCATION: (64)..(67)
<223> OTHER INFORMATION: Xaa can be any naturally occurring amino acid
<220> FEATURE:
<221> NAME/KEY: misc_feature
<222> LOCATION: (82)..(93)
<223> OTHER INFORMATION: Xaa can be any naturally occurring amino acid
<220> FEATURE:
<221> NAME/KEY: misc_feature
<222> LOCATION: (109)..(112)
<223> OTHER INFORMATION: Xaa can be any naturally occurring amino acid

<400> SEQUENCE: 69

Cys Leu Gly Thr Gly Thr Met Ile Ala Thr Ala Glu Gly Pro Ala Pro
1               5                   10                  15

Ile Asp Trp Leu Arg Pro Gly Asp Arg Val Leu Thr Arg Asp Xaa Xaa
            20                  25                  30

Xaa Gln Pro Leu Leu Trp Val Gly Gln His Thr Met Xaa Xaa Xaa Xaa
        35                  40                  45

Xaa Xaa Xaa Xaa Xaa Pro Leu Leu Leu Ser Ala Ala Cys Phe Gly Xaa
    50                  55                      60

Xaa Xaa Xaa Glu Arg Asp Val Leu Leu Ser Pro Gly Thr Gly Val Leu
65                  70                  75                  80

Leu Xaa Xaa Xaa Xaa Xaa Xaa Xaa Xaa Xaa Xaa Xaa Glu Met Phe
                85                  90                  95

Ala Lys Ala Arg His Ala Leu Pro Lys Ala Glu Ala Xaa Xaa Xaa Xaa
            100                 105                 110

Gln Lys Leu Tyr Ser Met Leu Leu Ala Thr Pro Glu Val Val Leu Ala
        115                 120                 125

Glu Gly Met Trp Val Gly Ser Val
        130             135

<210> SEQ ID NO 70
<211> LENGTH: 132
<212> TYPE: PRT
<213> ORGANISM: Rhodobacter capsulatus
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(51)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (77)..(86)
<223> OTHER INFORMATION: Xaa can be any naturally occurring amino acid
<220> FEATURE:
<221> NAME/KEY: misc_feature
<222> LOCATION: (102)..(108)
<223> OTHER INFORMATION: Xaa can be any naturally occurring amino acid

<400> SEQUENCE: 70
```

```
Cys Phe Ala Ala Gly Thr Leu Ile Ala Thr Arg Arg Gly Pro Lys Pro
1               5                   10                  15

Val Glu Asp Leu Gly Pro Glu Asp Arg Leu Gln Thr Ser Asp Xaa Xaa
            20                  25                  30

Xaa Arg Pro Val Gln Trp Val Gly Arg Trp Arg Val Xaa Xaa Xaa Xaa
        35                  40                  45

Xaa Xaa Xaa Pro Val Arg Phe Ala Pro Gly Val Leu Gly Xaa Asp Arg
    50                  55                  60

Ala Leu Phe Leu Ser Gly Gln His Arg Val Leu Ile Xaa Xaa Xaa Xaa
65              70                  75                  80

Xaa Xaa Xaa Xaa Xaa Xaa Glu Val Leu Val Ala Ala Lys Ala Leu Val
                85                  90                  95

Gly Leu Pro Gly Ile Xaa Xaa Xaa Xaa Xaa Xaa Xaa Val Asp Trp Val
            100                 105                 110

His Val Met Met Pro Thr His Glu Val Ile Phe Ala Glu Asn Ala Arg
            115                 120                 125

Ala Glu Thr Met
    130
```

<210> SEQ ID NO 71
<211> LENGTH: 135
<212> TYPE: PRT
<213> ORGANISM: Rhodobacter capsulatus
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (32)..(34)
<223> OTHER INFORMATION: Xaa can be any naturally occurring amino acid
<220> FEATURE:
<221> NAME/KEY: misc_feature
<222> LOCATION: (46)..(52)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (78)..(89)
<223> OTHER INFORMATION: Xaa can be any naturally occurring amino acid
<220> FEATURE:
<221> NAME/KEY: misc_feature
<222> LOCATION: (105)..(111)
<223> OTHER INFORMATION: Xaa can be any naturally occurring amino acid

<400> SEQUENCE: 71

```
Ala Phe Thr Thr Gly Thr Leu Ile Thr Met Ala Gly Gly Xaa Gln Arg
1               5                   10                  15

Pro Ile Glu Thr Leu Ala Pro Gly Asp Arg Val Leu Thr Arg Asp Xaa
            20                  25                  30

Xaa Xaa Gln Pro Val Arg Leu Val Ala Arg Ala Thr Leu Xaa Xaa Xaa
        35                  40                  45

Xaa Xaa Xaa Xaa Pro Val Val Ile Ser Ala Gly Thr Leu Gly Xaa Glu
    50                  55                  60

Ser Asp Leu Val Val Ala Pro His His Arg Val Phe Leu Xaa Xaa Xaa
65              70                  75                  80

Xaa Xaa Xaa Xaa Xaa Xaa Xaa Xaa Glu Ile Leu Val Gln Ala Lys
                85                  90                  95

His Leu Val Asp Gly Glu His Val Xaa Xaa Xaa Xaa Xaa Xaa Xaa Val
            100                 105                 110
```

```
Asp Tyr Phe Ala Leu Val Phe Asp Arg His Glu Ile Val Tyr Ala Glu
            115                 120                 125

Gly Val Pro Val Glu Ser Leu
        130                 135

<210> SEQ ID NO 72
<211> LENGTH: 139
<212> TYPE: PRT
<213> ORGANISM: Rhodobacter capsulatus
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(56)
<223> OTHER INFORMATION: Xaa can be any naturally occurring amino acid
<220> FEATURE:
<221> NAME/KEY: misc_feature
<222> LOCATION: (67)..(70)
<223> OTHER INFORMATION: Xaa can be any naturally occurring amino acid
<220> FEATURE:
<221> NAME/KEY: misc_feature
<222> LOCATION: (85)..(93)
<223> OTHER INFORMATION: Xaa can be any naturally occurring amino acid
<220> FEATURE:
<221> NAME/KEY: misc_feature
<222> LOCATION: (109)..(115)
<223> OTHER INFORMATION: Xaa can be any naturally occurring amino acid

<400> SEQUENCE: 72

Cys Phe Thr Ala Thr Ser Leu Ile Ala Thr Gly Gln Gly Gly Val Pro
1               5                   10                  15

Val Ser Glu Leu Val Pro Gly Ala Arg Val Ile Thr Arg Asp Xaa Xaa
            20                  25                  30

Xaa Gln Glu Leu Leu Trp Val Gly Arg Arg Phe Xaa Xaa Xaa Xaa Xaa
            35                  40                  45

Xaa Xaa Xaa Xaa Xaa Xaa Xaa Pro Val Arg Ile Ala Ala Gly Ala
        50                  55                  60

Leu Gly Xaa Xaa Xaa Xaa Glu Arg Asp Met Leu Val Ser Pro Asn His
65                  70                  75                  80

Arg Phe Leu Thr Xaa Xaa Xaa Xaa Xaa Xaa Xaa Xaa Xaa Glu Arg Leu
            85                  90                  95

Thr Met Ala Arg Asp Leu Val Gly Leu Asp Gly Ile Xaa Xaa Xaa Xaa
            100                 105                 110

Xaa Xaa Xaa Val Asp Tyr Trp Gln Leu Leu Phe Ala His His Glu Leu
            115                 120                 125

Val Leu Ala Asp Gly Ala Trp Ser Glu Ser Phe
        130                 135

<210> SEQ ID NO 73
<211> LENGTH: 142
<212> TYPE: PRT
<213> ORGANISM: Rhodobacter capsulatus
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(56)
<223> OTHER INFORMATION: Xaa can be any naturally occurring amino acid
<220> FEATURE:
<221> NAME/KEY: misc_feature
<222> LOCATION: (67)..(70)
<223> OTHER INFORMATION: Xaa can be any naturally occurring amino acid
```

```
<220> FEATURE:
<221> NAME/KEY: misc_feature
<222> LOCATION: (85)..(96)
<223> OTHER INFORMATION: Xaa can be any naturally occurring amino acid
<220> FEATURE:
<221> NAME/KEY: misc_feature
<222> LOCATION: (112)..(118)
<223> OTHER INFORMATION: Xaa can be any naturally occurring amino acid

<400> SEQUENCE: 73

Cys Leu Thr Pro Gly Thr Leu Ile Glu Thr Lys Arg Gly Gln Val Pro
1               5                   10                  15

Val Glu Lys Leu Arg Pro Gly Asp Arg Val Leu Thr Arg Asp Xaa Xaa
            20                  25                  30

Xaa Gln Pro Ile Arg Trp Ile Gly Arg Arg Leu Xaa Xaa Xaa Xaa
        35                  40                  45

Xaa Xaa Xaa Xaa Xaa Xaa Xaa Xaa Pro Val Arg Ile Ala Ala Gly Ala
    50                  55                  60

Leu Gly Xaa Xaa Xaa Xaa Glu Thr Asp Met Leu Val Ser Pro Gln His
65                  70                  75                  80

Arg Met Leu Ile Xaa Xaa Xaa Xaa Xaa Xaa Xaa Xaa Xaa Xaa Xaa Xaa
                85                  90                  95

Glu Val Leu Ala Ala Ala Leu His Met Leu Gly Gln Pro Gly Ile Xaa
            100                 105                 110

Xaa Xaa Xaa Xaa Xaa Val Thr Tyr Leu His Leu Met Leu Asp Ala
        115                 120                 125

His Glu Ile Ile Arg Ala Asn Gly Ala Trp Thr Glu Ser Phe
    130                 135                 140

<210> SEQ ID NO 74
<211> LENGTH: 136
<212> TYPE: PRT
<213> ORGANISM: Rhodobacter capsulatus
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(56)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (82)..(83)
<223> OTHER INFORMATION: Xaa can be any naturally occurring amino acid
<220> FEATURE:
<221> NAME/KEY: misc_feature
<222> LOCATION: (99)..(112)
<223> OTHER INFORMATION: Xaa can be any naturally occurring amino acid

<400> SEQUENCE: 74

Cys Leu Val Ala Gly Ser Arg Val Ser Thr Pro Arg Gly Pro Val Pro
1               5                   10                  15

Val Glu Asp Leu Arg Pro Glu Asp Leu Val Thr Val Arg Asp Xaa Xaa
            20                  25                  30

Xaa Leu Pro Val Leu Trp Ile Gly Arg Arg Val Xaa Xaa Xaa Xaa
        35                  40                  45

Xaa Xaa Xaa Xaa Xaa Xaa Xaa Xaa Pro Val Glu Ile Gly Ala Gly Arg
    50                  55                  60

Leu Gly Xaa Ala Ala Pro Val Arg Leu Ser Ala Leu His Gly Ile Ala
```

```
                 65                  70                  75                  80
Val Xaa Xaa Gly Phe Leu Ala Arg Ala Gly His Leu Ala Ala Thr Gly
                     85                  90                  95

Trp Gly Xaa Xaa Xaa Xaa Xaa Xaa Xaa Xaa Xaa Xaa Xaa Xaa
            100                 105                 110

Val Leu Tyr Leu His Leu Leu Leu Pro Arg His Ala Leu Leu Ser Val
            115                 120                 125

Glu Gly Leu Trp Val Glu Ser Phe
    130                 135

<210> SEQ ID NO 75
<211> LENGTH: 132
<212> TYPE: PRT
<213> ORGANISM: Rhodobacter capsulatus
<220> FEATURE:
<221> NAME/KEY: misc_feature
<222> LOCATION: (31)..(46)
<223> OTHER INFORMATION: Xaa can be any naturally occurring amino acid
<220> FEATURE:
<221> NAME/KEY: misc_feature
<222> LOCATION: (57)..(60)
<223> OTHER INFORMATION: Xaa can be any naturally occurring amino acid
<220> FEATURE:
<221> NAME/KEY: misc_feature
<222> LOCATION: (75)..(86)
<223> OTHER INFORMATION: Xaa can be any naturally occurring amino acid
<220> FEATURE:
<221> NAME/KEY: misc_feature
<222> LOCATION: (102)..(108)
<223> OTHER INFORMATION: Xaa can be any naturally occurring amino acid

<400> SEQUENCE: 75

Gly Phe Ala Met Gly Ser Arg Val Ala Thr Met Asp Gly Leu Leu Pro
1               5                   10                  15

Val Glu Phe Leu Asn Leu Gly Asp Arg Ile Val Thr Arg Ser Xaa Xaa
            20                  25                  30

Xaa Xaa Xaa Xaa Xaa Xaa Xaa Xaa Xaa Xaa Xaa Xaa Xaa Xaa Leu Val
            35                  40                  45

Gly Ile Ala Pro Gly Ala Leu Gly Xaa Xaa Xaa Xaa Gly Gln Ala Met
    50                  55                  60

Val Leu Gly Ser Gly Thr Gln Val Leu Leu Xaa Xaa Xaa Xaa Xaa Xaa
65                  70                  75                  80

Xaa Xaa Xaa Xaa Xaa Xaa Gln Ala Leu Val Ala Val Glu Arg Leu Ile
                85                  90                  95

Asp Gly Gln Phe Ile Xaa Xaa Xaa Xaa Xaa Xaa Xaa Ile Arg Ile Phe
            100                 105                 110

Ala Leu His Phe Glu Ala Pro Glu Val Ile Tyr Ala Asp Gly Val Glu
            115                 120                 125

Ile Gly Cys Lys
    130

<210> SEQ ID NO 76
<211> LENGTH: 142
<212> TYPE: PRT
<213> ORGANISM: Rhodobacter sphaeroides
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(56)
<223> OTHER INFORMATION: Xaa can be any naturally occurring amino acid
<220> FEATURE:
```

```
<221> NAME/KEY: misc_feature
<222> LOCATION: (67)..(70)
<223> OTHER INFORMATION: Xaa can be any naturally occurring amino acid
<220> FEATURE:
<221> NAME/KEY: misc_feature
<222> LOCATION: (85)..(96)
<223> OTHER INFORMATION: Xaa can be any naturally occurring amino acid
<220> FEATURE:
<221> NAME/KEY: misc_feature
<222> LOCATION: (112)..(118)
<223> OTHER INFORMATION: Xaa can be any naturally occurring amino acid

<400> SEQUENCE: 76

Cys Phe Thr Pro Gly Thr Leu Ile Ala Thr Val Arg Gly Glu Val Ala
1               5                   10                  15

Val Glu Ala Leu Ala Ala Gly Asp Arg Ile Val Thr Arg Asp Xaa Xaa
            20                  25                  30

Xaa Gln Pro Leu Arg Trp Ile Ser Arg Arg Leu Xaa Xaa Xaa Xaa
        35                  40                  45

Xaa Xaa Xaa Xaa Xaa Xaa Xaa Pro Val Leu Ile Glu Lys Gly Ser
    50                  55                  60

Leu Gly Xaa Xaa Xaa Xaa Asp Arg Asp Met Met Val Ser Pro Asn His
65                  70                  75                  80

Arg Ile Leu Val Xaa Xaa Xaa Xaa Xaa Xaa Xaa Xaa Xaa Xaa Xaa
                85                  90                  95

Glu Val Leu Val Ala Ala Lys His Leu Val Gly Pro Arg Gly Ile Xaa
            100                 105                 110

Xaa Xaa Xaa Xaa Xaa Xaa Thr Thr Tyr Leu His Leu Met Phe Asp Arg
        115                 120                 125

His Glu Val Val Leu Ala Asn Gly Ala Trp Thr Glu Ser Phe
    130                 135                 140

<210> SEQ ID NO 77
<211> LENGTH: 133
<212> TYPE: PRT
<213> ORGANISM: Rhodobacter sphaeroides
<220> FEATURE:
<221> NAME/KEY: misc_feature
<222> LOCATION: (31)..(47)
<223> OTHER INFORMATION: Xaa can be any naturally occurring amino acid
<220> FEATURE:
<221> NAME/KEY: misc_feature
<222> LOCATION: (58)..(61)
<223> OTHER INFORMATION: Xaa can be any naturally occurring amino acid
<220> FEATURE:
<221> NAME/KEY: misc_feature
<222> LOCATION: (76)..(87)
<223> OTHER INFORMATION: Xaa can be any naturally occurring amino acid
<220> FEATURE:
<221> NAME/KEY: misc_feature
<222> LOCATION: (103)..(109)
<223> OTHER INFORMATION: Xaa can be any naturally occurring amino acid

<400> SEQUENCE: 77

Ser Leu Thr Ala Gly Thr Pro Val Leu Thr Leu Ala Gly Ile Arg Pro
1               5                   10                  15

Ala Glu Gly Ile Arg Pro Gly Asp Arg Leu Val Ala Arg Ser Xaa Xaa
            20                  25                  30

Xaa Xaa Xaa Xaa Xaa Xaa Xaa Xaa Xaa Xaa Xaa Xaa Xaa Xaa Xaa Met
        35                  40                  45

Val Ala Ile Gly Ala Ser Thr Leu Ala Xaa Xaa Xaa Xaa Asp Glu Thr
    50                  55                  60

Leu Leu Val Pro Ala Asp Gln Pro Leu Leu Xaa Xaa Xaa Xaa Xaa
65                  70                  75                  80
```

```
Xaa Xaa Xaa Xaa Xaa Xaa Xaa Pro Val Val Leu Pro Ala Arg Arg Leu
                85                  90                  95

Val Asp Gly Gln Leu Thr Xaa Xaa Xaa Xaa Xaa Xaa Val Asp Leu
            100                 105                 110

Val Thr Leu Thr Phe Ala Ala Pro Ala Ala Ile Tyr Ala Ser Glu Leu
            115                 120                 125

His Pro Val Thr Arg
    130

<210> SEQ ID NO 78
<211> LENGTH: 132
<212> TYPE: PRT
<213> ORGANISM: Brucella suis
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(56)
<223> OTHER INFORMATION: Xaa can be any naturally occurring amino acid
<220> FEATURE:
<221> NAME/KEY: misc_feature
<222> LOCATION: (67)..(70)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (101)..(108)
<223> OTHER INFORMATION: Xaa can be any naturally occurring amino acid

<400> SEQUENCE: 78

Cys Leu Leu Lys Gly Thr Leu Val Thr Thr Pro Asn Gly Pro Val Ala
1               5                   10                  15

Val Glu Lys Leu Cys Val Gly Asp Leu Val Thr Thr Val Ser Xaa Xaa
            20                  25                  30

Xaa Leu Pro Ile Lys Trp Ile Gly Trp Gln Asn Tyr Xaa Xaa Xaa Xaa
            35                  40                  45

Xaa Xaa Xaa Xaa Xaa Xaa Xaa Pro Ile Arg Val Arg Arg His Ala
        50                  55                  60

Leu Asp Xaa Xaa Xaa Xaa His Arg Asp Leu Tyr Leu Ser Pro Asn His
65                  70                  75                  80

Ala Leu Phe Ile Xaa Gly Val Leu Ile Arg Val Lys Asp Leu Val Asn
                85                  90                  95

Gly Arg Ser Ile Xaa Xaa Xaa Xaa Xaa Xaa Xaa Leu Asp Tyr Tyr
            100                 105                 110

Asn Ile Val Leu Asp Arg His Ala Val Val Leu Ala Glu Gly Ala Ala
            115                 120                 125

Val Glu Thr Phe
    130

<210> SEQ ID NO 79
<211> LENGTH: 132
<212> TYPE: PRT
<213> ORGANISM: Brucella melitensis
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
```

```
<222> LOCATION: (45)..(56)
<223> OTHER INFORMATION: Xaa can be any naturally occurring amino acid
<220> FEATURE:
<221> NAME/KEY: misc_feature
<222> LOCATION: (67)..(70)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (101)..(108)
<223> OTHER INFORMATION: Xaa can be any naturally occurring amino acid

<400> SEQUENCE: 79

Cys Leu Leu Lys Gly Thr Leu Thr Thr Pro Asn Gly Pro Val Ala
1               5                   10                  15

Val Glu Lys Leu Cys Val Gly Asp Leu Val Thr Thr Val Ser Xaa Xaa
            20                  25                  30

Xaa Leu Pro Ile Lys Trp Ile Gly Trp Gln Asn Tyr Xaa Xaa Xaa Xaa
        35                  40                  45

Xaa Xaa Xaa Xaa Xaa Xaa Xaa Xaa Pro Ile Arg Val Arg Arg His Ala
    50                  55                  60

Leu Asp Xaa Xaa Xaa Xaa His Arg Asp Leu Tyr Leu Ser Pro Asn His
65                  70                  75                  80

Ala Leu Phe Ile Xaa Gly Val Leu Ile Arg Val Lys Asp Leu Val Asn
                85                  90                  95

Gly Arg Ser Ile Xaa Xaa Xaa Xaa Xaa Xaa Xaa Leu Asp Tyr Tyr
            100                 105                 110

Asn Ile Val Leu Asp Arg His Ala Val Val Leu Ala Glu Gly Ala Ala
        115                 120                 125

Val Glu Thr Phe
        130

<210> SEQ ID NO 80
<211> LENGTH: 138
<212> TYPE: PRT
<213> ORGANISM: Unknown
<220> FEATURE:
<223> OTHER INFORMATION: BIL1 domain sequence from an unknown origin
<220> FEATURE:
<221> NAME/KEY: misc_feature
<222> LOCATION: (31)..(38)
<223> OTHER INFORMATION: Xaa can be any naturally occurring amino acid
<220> FEATURE:
<221> NAME/KEY: misc_feature
<222> LOCATION: (50)..(62)
<223> OTHER INFORMATION: Xaa can be any naturally occurring amino acid
<220> FEATURE:
<221> NAME/KEY: misc_feature
<222> LOCATION: (73)..(76)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (107)..(114)
<223> OTHER INFORMATION: Xaa can be any naturally occurring amino acid

<400> SEQUENCE: 80

Cys Phe Leu Pro Gly Thr Met Ile Lys Thr Pro Ser Gly Glu Arg Pro
1               5                   10                  15

Val Glu Asp Ile Gln Ile Asn Asp Glu Val Ile Thr Phe Asp Xaa Xaa
            20                  25                  30
```

```
Xaa Xaa Xaa Xaa Xaa Xaa Ser Lys Ile Lys Trp Val Gly Ser Lys Thr
            35                  40                  45

Ile Xaa Xaa Xaa Xaa Xaa Xaa Xaa Xaa Xaa Xaa Xaa Xaa Pro Val
 50                  55                  60

Arg Ile Leu Lys Asn Ala Ile Ser Xaa Xaa Xaa Xaa His Lys Asp Leu
 65                  70                  75                  80

Leu Val Thr Pro Glu His Cys Leu Phe Phe Xaa Gly Lys Phe Ile Pro
                 85                  90                  95

Val Arg Met Leu Val Asn His Gln Thr Ile Xaa Xaa Xaa Xaa Xaa Xaa
            100                 105                 110

Xaa Xaa Tyr Thr Tyr Tyr His Ile Glu Thr Glu Asn His Ser Val Ile
        115                 120                 125

Tyr Ser Asp Gly Met Leu Thr Glu Ser Tyr
130                 135
```

<210> SEQ ID NO 81
<211> LENGTH: 138
<212> TYPE: PRT
<213> ORGANISM: Unknown
<220> FEATURE:
<223> OTHER INFORMATION: BIL2 domain sequence from an unknown origin
<220> FEATURE:
<221> NAME/KEY: misc_feature
<222> LOCATION: (31)..(38)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (50)..(62)
<223> OTHER INFORMATION: Xaa can be any naturally occurring amino acid
<220> FEATURE:
<221> NAME/KEY: misc_feature
<222> LOCATION: (73)..(76)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (107)..(114)
<223> OTHER INFORMATION: Xaa can be any naturally occurring amino acid

<400> SEQUENCE: 81

```
Cys Phe Leu Ser Gly Thr Gln Ile Lys Thr Lys Leu Gly Val Lys Asn
 1               5                  10                  15

Ile Glu Ala Leu Gln Val Gly Asp Phe Val Thr Thr Tyr Asp Xaa Xaa
             20                  25                  30

Xaa Xaa Xaa Xaa Xaa Xaa Arg Glu Val Thr Trp Val Gly Xaa Lys Tyr
        35                  40                  45

Cys Xaa Xaa Xaa Xaa Xaa Xaa Xaa Xaa Xaa Xaa Xaa Pro Val
 50                  55                  60

Arg Ile Val Lys Asp Ala Ile Ala Xaa Xaa Xaa Tyr Lys Asp Leu
 65                  70                  75                  80

Leu Val Thr Ala Glu His Cys Leu Phe Phe Xaa Asp Lys Phe Ile Pro
                 85                  90                  95

Ala Arg Met Leu Val Asn Gly Ser Thr Ile Xaa Xaa Xaa Xaa Xaa Xaa
            100                 105                 110

Xaa Xaa Tyr Glu Tyr Tyr His Leu Glu Thr Gln Asp His Ala Val Ile
        115                 120                 125
```

Ile Ala Asp Gly Val Arg Thr Glu Ser Tyr
    130                 135

<210> SEQ ID NO 82
<211> LENGTH: 138
<212> TYPE: PRT
<213> ORGANISM: Methylobacterium extorquens
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(56)
<223> OTHER INFORMATION: Xaa can be any naturally occurring amino acid
<220> FEATURE:
<221> NAME/KEY: misc_feature
<222> LOCATION: (67)..(70)
<223> OTHER INFORMATION: Xaa can be any naturally occurring amino acid
<220> FEATURE:
<221> NAME/KEY: misc_feature
<222> LOCATION: (85)..(92)
<223> OTHER INFORMATION: Xaa can be any naturally occurring amino acid
<220> FEATURE:
<221> NAME/KEY: misc_feature
<222> LOCATION: (108)..(114)
<223> OTHER INFORMATION: Xaa can be any naturally occurring amino acid

<400> SEQUENCE: 82

Cys Phe Thr Thr Gly Thr Leu Ile Arg Thr Ala Arg Gly Ser Val Ala
1               5                   10                  15

Val Glu Asp Leu Ile Val Gly Asp Leu Ala Val Thr Ala Ser Xaa Xaa
            20                  25                  30

Xaa Arg Pro Ile Thr Trp Ile Gly Asn Arg Ala Leu Xaa Xaa Xaa Xaa
        35                  40                  45

Xaa Xaa Xaa Xaa Xaa Xaa Xaa Xaa Pro Ile Arg Ile Arg Ala Gly Ala
    50                  55                  60

Phe Gly Xaa Xaa Xaa Xaa Ala Arg Asp Leu Arg Leu Ser His Gly His
65                  70                  75                  80

Pro Val Leu Val Xaa Xaa Xaa Xaa Xaa Xaa Xaa Xaa Gly Val Leu Val
                85                  90                  95

Pro Val Met Cys Leu Ile Asn Gly Thr Ser Val Xaa Xaa Xaa Xaa Xaa
            100                 105                 110

Xaa Xaa Val Thr Tyr Trp His Ile Glu Leu Asp Ala His Asp Ile Leu
        115                 120                 125

Leu Ala Glu Gly Leu Ala Ala Glu Ser Tyr
    130                 135

<210> SEQ ID NO 83
<211> LENGTH: 142
<212> TYPE: PRT
<213> ORGANISM: Silicibacter pomeroyi
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(56)
<223> OTHER INFORMATION: Xaa can be any naturally occurring amino acid
<220> FEATURE:
<221> NAME/KEY: misc_feature
<222> LOCATION: (67)..(70)
<223> OTHER INFORMATION: Xaa can be any naturally occurring amino acid
<220> FEATURE:
<221> NAME/KEY: misc_feature
<222> LOCATION: (85)..(96)

```
<223> OTHER INFORMATION: Xaa can be any naturally occurring amino acid
<220> FEATURE:
<221> NAME/KEY: misc_feature
<222> LOCATION: (112)..(118)
<223> OTHER INFORMATION: Xaa can be any naturally occurring amino acid

<400> SEQUENCE: 83

Cys Phe Thr Pro Gly Thr Lys Ile Ala Thr Pro Lys Gly Glu Arg Leu
1               5                   10                  15

Val Glu Asp Leu Glu Val Gly Asp Arg Val Ile Thr Arg Asp Xaa Xaa
            20                  25                  30

Xaa Gln Glu Ile Arg Trp Val Gly Ser Arg Thr Leu Xaa Xaa Xaa Xaa
        35                  40                  45

Xaa Xaa Xaa Xaa Xaa Xaa Xaa Pro Val Leu Ile Arg Gln Gly Ala
    50                  55                  60

Leu Gly Xaa Xaa Xaa Xaa Glu Arg Asp Met Ile Val Ser Pro Asn His
65              70                  75                  80

Arg Ile Leu Val Xaa Xaa Xaa Xaa Xaa Xaa Xaa Xaa Xaa Xaa Xaa
                85                  90                  95

Glu Val Leu Val Ala Ala Lys His Leu Ile Gly Leu Glu Gly Val Xaa
                100                 105                 110

Xaa Xaa Xaa Xaa Xaa Xaa Val Thr Tyr Ile His Phe Met Phe Asp Gln
        115                 120                 125

His Glu Val Val Leu Ser Asp Gly Ala Trp Thr Glu Ser Phe
        130                 135                 140

<210> SEQ ID NO 84
<211> LENGTH: 134
<212> TYPE: PRT
<213> ORGANISM: Silicibacter pomeroyi
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(51)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (77)..(88)
<223> OTHER INFORMATION: Xaa can be any naturally occurring amino acid
<220> FEATURE:
<221> NAME/KEY: misc_feature
<222> LOCATION: (104)..(110)
<223> OTHER INFORMATION: Xaa can be any naturally occurring amino acid

<400> SEQUENCE: 84

Cys Phe Cys Arg Gly Thr Leu Ile Ala Thr Ala Gly Gly Glu Ile Pro
1               5                   10                  15

Val Glu Lys Leu Arg Pro Gly Asp Arg Val Ile Thr Arg Asp Xaa Xaa
            20                  25                  30

Xaa Gln Arg Ile Arg Trp Ile Gly Gly Thr Ser Arg Xaa Xaa Xaa
        35                  40                  45

Xaa Xaa Xaa Pro Ile Arg Ile Arg Thr Gly Val Leu Lys Xaa Thr Arg
    50                  55                  60

Asp Leu Leu Val Ser Pro Asn His Arg Ile Leu Met Xaa Xaa Xaa Xaa
65              70                  75                  80

Xaa Xaa Xaa Xaa Xaa Xaa Xaa Xaa Glu Val Leu Val Ala Ala Lys Phe
```

-continued

```
                85                  90                  95
Leu Val Asp Gly Arg Ala Ile Xaa Xaa Xaa Xaa Xaa Xaa Val Asp
            100                 105                 110

Tyr Tyr His Met Leu Phe Asp Gln His Glu Leu Val Leu Ser Glu Gln
            115                 120                 125

Ala Trp Ser Glu Ser Phe
            130

<210> SEQ ID NO 85
<211> LENGTH: 134
<212> TYPE: PRT
<213> ORGANISM: Silicibacter pomeroyi
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(51)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (77)..(88)
<223> OTHER INFORMATION: Xaa can be any naturally occurring amino acid
<220> FEATURE:
<221> NAME/KEY: misc_feature
<222> LOCATION: (104)..(110)
<223> OTHER INFORMATION: Xaa can be any naturally occurring amino acid

<400> SEQUENCE: 85

Cys Phe Ala Ala Gly Thr Arg Ile Glu Thr Asp Arg Gly Gly Arg Ala
1               5                   10                  15

Ile Glu Asp Ile Ala Val Gly Asp Leu Val Leu Thr Arg Asp Xaa Xaa
            20                  25                  30

Xaa Gln Pro Val Arg Trp Thr Gly Arg Arg Ser Val Xaa Xaa Xaa Xaa
        35                  40                  45

Xaa Xaa Xaa Pro Ile Arg Ile Ala Ser Gly Lys Leu Gly Xaa Leu Arg
    50                  55                  60

Asp Leu Leu Val Ser Pro Gln His Arg Leu Leu Leu Xaa Xaa Xaa Xaa
65                  70                  75                  80

Xaa Xaa Xaa Xaa Xaa Xaa Xaa Xaa Glu Val Leu Ala Ala Ala Val His
                85                  90                  95

Leu Arg Asp Asp Arg His Ile Xaa Xaa Xaa Xaa Xaa Xaa Xaa Val Thr
            100                 105                 110

Tyr Val His Leu Met Phe Asp Arg His Glu Ile Ile Tyr Ala Glu Gly
            115                 120                 125

Val Ala Ser Glu Ser Phe
            130

<210> SEQ ID NO 86
<211> LENGTH: 143
<212> TYPE: PRT
<213> ORGANISM: Silicibacter pomeroyi
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(56)
<223> OTHER INFORMATION: Xaa can be any naturally occurring amino acid
```

```
<220> FEATURE:
<221> NAME/KEY: misc_feature
<222> LOCATION: (67)..(70)
<223> OTHER INFORMATION: Xaa can be any naturally occurring amino acid
<220> FEATURE:
<221> NAME/KEY: misc_feature
<222> LOCATION: (85)..(96)
<223> OTHER INFORMATION: Xaa can be any naturally occurring amino acid
<220> FEATURE:
<221> NAME/KEY: misc_feature
<222> LOCATION: (112)..(119)
<223> OTHER INFORMATION: Xaa can be any naturally occurring amino acid

<400> SEQUENCE: 86

Cys Phe Thr Pro Gly Thr Arg Ile Ala Thr Pro Thr Gly Pro Arg Leu
1               5                   10                  15

Ile Glu Glu Leu Arg Glu Gly Asp Lys Val Gln Thr Arg Asp Xaa Xaa
            20                  25                  30

Xaa Gln Glu Ile Gln Trp Ile Gly Gln Arg Arg Met Xaa Xaa Xaa Xaa
        35                  40                  45

Xaa Xaa Xaa Xaa Xaa Xaa Xaa Xaa Pro Ile Arg Met Arg Val Gly Ala
    50                  55                  60

Leu Gly Xaa Xaa Xaa Xaa Asp Ala Glu Leu Leu Val Ser Pro Glu His
65                  70                  75                  80

Arg Met Leu Leu Xaa Xaa Xaa Xaa Xaa Xaa Xaa Xaa Xaa Xaa Xaa Xaa
                85                  90                  95

Glu Val Leu Val Pro Ala Arg Asp Leu Val Asn Asp Ser Thr Ile Xaa
            100                 105                 110

Xaa Xaa Xaa Xaa Xaa Xaa Xaa Val Thr Tyr Val His Leu Leu Leu Pro
        115                 120                 125

Ser His Gln Ile Leu Trp Ala Asn Gly Ile Glu Thr Glu Ser Phe
    130                 135                 140

<210> SEQ ID NO 87
<211> LENGTH: 134
<212> TYPE: PRT
<213> ORGANISM: Silicibacter pomeroyi
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(51)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (77)..(88)
<223> OTHER INFORMATION: Xaa can be any naturally occurring amino acid
<220> FEATURE:
<221> NAME/KEY: misc_feature
<222> LOCATION: (104)..(110)
<223> OTHER INFORMATION: Xaa can be any naturally occurring amino acid

<400> SEQUENCE: 87

Cys Phe Ala Ala Gly Thr Phe Ile Glu Ile Glu Ser Gly Pro Ile Pro
1               5                   10                  15

Val Glu Thr Leu Arg Pro Gly Asp Leu Val Gln Thr Leu Asp Xaa Xaa
            20                  25                  30

Xaa Gln Pro Leu Leu Gln Leu Ala Lys Thr Thr Val Xaa Xaa Xaa Xaa
        35                  40                  45
```

Xaa Xaa Xaa Pro Val Leu Phe Arg Ala Gly Val Leu Gly Xaa Phe Arg
        50                  55                  60

Asp Leu Tyr Val Ser Gln Gln His Arg Met Leu Ile Xaa Xaa Xaa Xaa
 65                  70                  75                  80

Xaa Xaa Xaa Xaa Xaa Xaa Xaa Xaa Glu Val Phe Val Pro Ala Arg Met
                     85                  90                  95

Leu Val Asn Gly Ser Thr Ile Xaa Xaa Xaa Xaa Xaa Xaa Xaa Leu Thr
            100                 105                 110

Tyr Tyr His Leu Leu Phe Ala Arg His Glu Ile Val Phe Ser Glu Gly
        115                 120                 125

Ile Pro Thr Glu Ser Tyr
        130

<210> SEQ ID NO 88
<211> LENGTH: 134
<212> TYPE: PRT
<213> ORGANISM: Silicibacter pomeroyi
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(51)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (77)..(88)
<223> OTHER INFORMATION: Xaa can be any naturally occurring amino acid
<220> FEATURE:
<221> NAME/KEY: misc_feature
<222> LOCATION: (104)..(110)
<223> OTHER INFORMATION: Xaa can be any naturally occurring amino acid

<400> SEQUENCE: 88

Cys Phe Val Ala Gly Thr Leu Ile Asp Thr Pro Tyr Gly Glu Arg Gln
 1               5                  10                  15

Val Glu Arg Leu Thr Pro Gly Asp Gln Val Phe Thr Arg Asp Xaa Xaa
                 20                  25                  30

Xaa Gln Glu Val Arg Trp Val Gly Glu Arg Thr Val Xaa Xaa Xaa Xaa
        35                  40                  45

Xaa Xaa Xaa Pro Ile Leu Ile Arg Ala Gly Thr Tyr Gly Xaa Gln Arg
        50                  55                  60

Asp Leu Met Val Ser Pro Gln His Arg Ile Leu Ile Xaa Xaa Xaa Xaa
 65                  70                  75                  80

Xaa Xaa Xaa Xaa Xaa Xaa Xaa Xaa Glu Val Leu Val Ala Ala Lys Asp
                     85                  90                  95

Leu Val Asp Gly Arg Arg Val Xaa Xaa Xaa Xaa Xaa Xaa Xaa Ile Thr
            100                 105                 110

Tyr Val His Val Met Phe Asp Ser His Gln Val Ile Tyr Ser Glu Gly
        115                 120                 125

Leu Ala Ser Glu Ser Phe
        130

<210> SEQ ID NO 89
<211> LENGTH: 135
<212> TYPE: PRT
<213> ORGANISM: Silicibacter pomeroyi
<220> FEATURE:

```
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(51)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (77)..(88)
<223> OTHER INFORMATION: Xaa can be any naturally occurring amino acid
<220> FEATURE:
<221> NAME/KEY: misc_feature
<222> LOCATION: (104)..(111)
<223> OTHER INFORMATION: Xaa can be any naturally occurring amino acid

<400> SEQUENCE: 89

Ser Leu His Pro Glu Thr Pro Ile Ala Thr Pro Asp Gly Tyr Arg Pro
1               5                   10                  15

Leu Ser Lys Ile Arg Arg Gly Asp Thr Val Ile Val Ala Ser Xaa Xaa
            20                  25                  30

Xaa Val Pro Val Leu His Arg Val Ser Arg Thr Met Xaa Xaa Xaa Xaa
        35                  40                  45

Xaa Xaa Xaa Pro Leu Thr Ile Arg Arg Pro Tyr Phe Gly Xaa Arg Gln
    50                  55                  60

Asp Ile Gln Ala Ala Pro Ser Gln Arg Leu Leu Leu Xaa Xaa Xaa Xaa
65                  70                  75                  80

Xaa Xaa Xaa Xaa Xaa Xaa Xaa Xaa Ser Val Leu Val Pro Ala Arg His
                85                  90                  95

Leu Thr Gly Gly His Ser Val Xaa Xaa Xaa Xaa Xaa Xaa Xaa Xaa Ala
            100                 105                 110

Thr Tyr Ala Gln Leu Leu Leu Pro Thr Asn Glu Ala Met Ile Thr Ala
        115                 120                 125

Gly Ala Leu Ala Glu Ser Leu
    130                 135

<210> SEQ ID NO 90
<211> LENGTH: 143
<212> TYPE: PRT
<213> ORGANISM: Silicibacter pomeroyi
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(56)
<223> OTHER INFORMATION: Xaa can be any naturally occurring amino acid
<220> FEATURE:
<221> NAME/KEY: misc_feature
<222> LOCATION: (67)..(70)
<223> OTHER INFORMATION: Xaa can be any naturally occurring amino acid
<220> FEATURE:
<221> NAME/KEY: misc_feature
<222> LOCATION: (85)..(96)
<223> OTHER INFORMATION: Xaa can be any naturally occurring amino acid
<220> FEATURE:
<221> NAME/KEY: misc_feature
<222> LOCATION: (112)..(119)
<223> OTHER INFORMATION: Xaa can be any naturally occurring amino acid

<400> SEQUENCE: 90

Cys Phe Val Ala Gly Ser Leu Ile Asp Thr Val Glu Gly Pro Arg Pro
1               5                   10                  15
```

Val Glu Thr Leu Ala Val Gly Asp Leu Val Pro Val Glu Asp Xaa Xaa
            20                  25                  30

Xaa Gln Pro Ile Leu Trp Ile Gly Lys Arg Thr Leu Xaa Xaa Xaa Xaa
        35                  40                  45

Xaa Xaa Xaa Xaa Xaa Xaa Xaa Pro Val Arg Ile Arg Arg Asp Ala
    50                  55                  60

Leu Gly Xaa Xaa Xaa Xaa His Arg Thr Leu Trp Val Ser Pro Gln His
65                  70                  75                  80

Arg Ile Val Leu Xaa Xaa Xaa Xaa Xaa Xaa Xaa Xaa Xaa Xaa Xaa
                85                  90                  95

Gln Val Phe Ala Ala Ala Ile His Leu Thr Asn Asp Asp Thr Ile Xaa
                100                 105                 110

Xaa Xaa Xaa Xaa Xaa Xaa Xaa Val Thr Tyr Tyr His Leu Ala Phe Glu
        115                 120                 125

Arg His Leu Leu Leu Arg Ala His Gly Leu Leu Ser Glu Ser Ile
    130                 135                 140

<210> SEQ ID NO 91
<211> LENGTH: 135
<212> TYPE: PRT
<213> ORGANISM: Silicibacter pomeroyi
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(51)
<223> OTHER INFORMATION: Xaa can be any naturally occurring amino acid
<220> FEATURE:
<221> NAME/KEY: misc_feature
<222> LOCATION: (62)..(63)
<223> OTHER INFORMATION: Xaa can be any naturally occurring amino acid
<220> FEATURE:
<221> NAME/KEY: misc_feature
<222> LOCATION: (78)..(89)
<223> OTHER INFORMATION: Xaa can be any naturally occurring amino acid
<220> FEATURE:
<221> NAME/KEY: misc_feature
<222> LOCATION: (105)..(111)
<223> OTHER INFORMATION: Xaa can be any naturally occurring amino acid

<400> SEQUENCE: 91

Cys Phe Thr Pro Gly Thr Leu Ile Ala Thr Ala His Gly Pro Arg Ala
1               5                   10                  15

Ile Glu Thr Leu Arg Pro Gly Asp Leu Ile Val Thr Arg Asp Xaa Xaa
            20                  25                  30

Xaa Gln Pro Leu Arg Trp Val Gly Ser Arg Thr Val Xaa Xaa Xaa Xaa
        35                  40                  45

Xaa Xaa Xaa Pro Ile Arg Leu Asp Pro Thr Leu Leu Gln Xaa Xaa Ser
    50                  55                  60

Ala Pro Leu Leu Val Ser Pro Gln His Arg Met Leu Trp Xaa Xaa Xaa
65                  70                  75                  80

Xaa Xaa Xaa Xaa Xaa Xaa Xaa Xaa Xaa Glu Val Leu Val Ala Ala Thr
                85                  90                  95

His Leu Leu Gly Ser Pro Ala Ala Xaa Xaa Xaa Xaa Xaa Xaa Xaa Val
                100                 105                 110

Thr Tyr Met His Leu Met Leu Asp Arg His Glu Val Ile Tyr Ala Asn
        115                 120                 125

Asp Ala Ala Thr Glu Ser Phe
    130                 135

<210> SEQ ID NO 92
<211> LENGTH: 134
<212> TYPE: PRT
<213> ORGANISM: Silicibacter pomeroyi
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(51)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (77)..(88)
<223> OTHER INFORMATION: Xaa can be any naturally occurring amino acid
<220> FEATURE:
<221> NAME/KEY: misc_feature
<222> LOCATION: (104)..(110)
<223> OTHER INFORMATION: Xaa can be any naturally occurring amino acid

<400> SEQUENCE: 92

Cys Phe Thr Pro Gly Thr Ile Ile Asp Thr Glu Asp Gly Pro Arg Leu
1               5                   10                  15

Ile Glu Glu Leu Gln Pro Gly Asp Leu Ile Arg Thr Leu Asp Xaa Xaa
            20                  25                  30

Xaa Gln Pro Leu Arg Trp Ile Gly Arg Thr Thr Val Xaa Xaa Xaa Xaa
        35                  40                  45

Xaa Xaa Xaa Pro Val Leu Ile Arg Ala Gly Ala Leu Asp Xaa Arg Arg
    50                  55                  60

Asp Leu Ile Val Ser Pro Gln His Arg Met Leu Ile Xaa Xaa Xaa Xaa
65                  70                  75                  80

Xaa Xaa Xaa Xaa Xaa Xaa Xaa Xaa Gln Ala Leu Val Ala Ala Lys His
                85                  90                  95

Leu Val Asn Ala Arg Asp Ile Xaa Xaa Xaa Xaa Xaa Xaa Xaa Val Thr
            100                 105                 110

Tyr Ile His Leu Leu Phe Asp Arg His Glu Ile Ile Trp Ala Glu Gly
        115                 120                 125

Cys Pro Thr Glu Ser Phe
    130

<210> SEQ ID NO 93
<211> LENGTH: 143
<212> TYPE: PRT
<213> ORGANISM: Silicibacter pomeroyi
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(56)
<223> OTHER INFORMATION: Xaa can be any naturally occurring amino acid
<220> FEATURE:
<221> NAME/KEY: misc_feature
<222> LOCATION: (67)..(70)
<223> OTHER INFORMATION: Xaa can be any naturally occurring amino acid
<220> FEATURE:
<221> NAME/KEY: misc_feature
<222> LOCATION: (85)..(96)
<223> OTHER INFORMATION: Xaa can be any naturally occurring amino acid
<220> FEATURE:
<221> NAME/KEY: misc_feature

```
<222> LOCATION: (112)..(119)
<223> OTHER INFORMATION: Xaa can be any naturally occurring amino acid

<400> SEQUENCE: 93

Cys Phe Ala Ala Gly Thr Arg Ile Ala Thr Pro Lys Gly Ala Arg Pro
1               5                   10                  15

Val Glu Thr Leu Ala Val Gly Asp Leu Val Gln Thr Leu Asp Xaa Xaa
            20                  25                  30

Xaa Gln Pro Ile Arg Trp Ile Gly Thr Arg Arg Val Xaa Xaa Xaa Xaa
        35                  40                  45

Xaa Xaa Xaa Xaa Xaa Xaa Xaa Xaa Pro Val Val Ile Pro Ala His Ser
    50                  55                  60

Phe Ala Xaa Xaa Xaa Xaa Thr His Pro Leu Leu Leu Ser Gln Gln His
65                  70                  75                  80

Arg Val Leu Leu Xaa Xaa Xaa Xaa Xaa Xaa Xaa Xaa Xaa Xaa Xaa Xaa
                85                  90                  95

Glu Ile Leu Ile Ala Ala Arg Arg Leu Thr Gly Leu His Gly Ile Xaa
            100                 105                 110

Xaa Xaa Xaa Xaa Xaa Xaa Xaa Val Arg Tyr Ile His Phe Ala Leu Asp
        115                 120                 125

Arg His Glu Ile Val Phe Ala Asn Gly Leu Pro Ala Glu Thr Leu
    130                 135                 140

<210> SEQ ID NO 94
<211> LENGTH: 135
<212> TYPE: PRT
<213> ORGANISM: Silicibacter pomeroyi
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (32)..(34)
<223> OTHER INFORMATION: Xaa can be any naturally occurring amino acid
<220> FEATURE:
<221> NAME/KEY: misc_feature
<222> LOCATION: (46)..(52)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (78)..(89)
<223> OTHER INFORMATION: Xaa can be any naturally occurring amino acid
<220> FEATURE:
<221> NAME/KEY: misc_feature
<222> LOCATION: (105)..(111)
<223> OTHER INFORMATION: Xaa can be any naturally occurring amino acid

<400> SEQUENCE: 94

Ser Phe Thr Arg Gly Thr His Ile Thr Leu Gly Ser Gly Xaa Gln Val
1               5                   10                  15

Arg Ile Glu Asp Leu Lys Val Gly Asp Arg Val Leu Thr Arg Asp Xaa
            20                  25                  30

Xaa Xaa Arg Glu Val Arg Trp Ile Gly Gln Thr Thr Val Xaa Xaa Xaa
        35                  40                  45

Xaa Xaa Xaa Xaa Pro Ile Val Ile Arg Ala Gly Thr Leu Asn Xaa Glu
    50                  55                  60

Asn Asp Leu Val Val Ser Pro Asp His Arg Leu Phe Val Xaa Xaa Xaa
65                  70                  75                  80
```

```
Xaa Xaa Xaa Xaa Xaa Xaa Xaa Xaa Xaa Glu Leu Leu Lys Ala Arg
                85                  90                  95

His Leu Val Asn Gly Asp Thr Val Xaa Xaa Xaa Xaa Xaa Xaa Val
            100                 105                 110

Asp Tyr Phe Gln Leu Leu Phe Asp Arg His His Ile Ile Tyr Ala Glu
        115                 120                 125

Gly Ile Ala Ala Glu Thr Met
    130                 135

<210> SEQ ID NO 95
<211> LENGTH: 144
<212> TYPE: PRT
<213> ORGANISM: Silicibacter pomeroyi
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(57)
<223> OTHER INFORMATION: Xaa can be any naturally occurring amino acid
<220> FEATURE:
<221> NAME/KEY: misc_feature
<222> LOCATION: (68)..(71)
<223> OTHER INFORMATION: Xaa can be any naturally occurring amino acid
<220> FEATURE:
<221> NAME/KEY: misc_feature
<222> LOCATION: (86)..(97)
<223> OTHER INFORMATION: Xaa can be any naturally occurring amino acid
<220> FEATURE:
<221> NAME/KEY: misc_feature
<222> LOCATION: (113)..(120)
<223> OTHER INFORMATION: Xaa can be any naturally occurring amino acid

<400> SEQUENCE: 95

Ala Phe Ser Arg Gly Ser Leu Ile Asp Thr Asp Cys Gly Pro Met Ala
1               5                   10                  15

Ile Glu Asp Leu Leu Pro Gly Asp Arg Val Ile Thr Gln Asp Xaa Xaa
            20                  25                  30

Xaa Gln Glu Val Val Trp Lys Gly Ser Thr Val Ile Xaa Xaa Xaa Xaa
        35                  40                  45

Xaa Xaa Xaa Xaa Xaa Xaa Xaa Xaa Xaa Leu Thr Arg Ile Met Ala Asp
    50                  55                  60

Ala Phe Gly Xaa Xaa Xaa Xaa Met Ser Gly Val Ile Ala Gly Pro Ser
65                  70                  75                  80

Ala Arg Leu Leu Ala Xaa Xaa Xaa Xaa Xaa Xaa Xaa Xaa Xaa Xaa Xaa
                85                  90                  95

Xaa Pro Met Leu Thr Pro Val Gln His Phe Val Asp Gly Met Gly Ile
            100                 105                 110

Xaa Xaa Xaa Xaa Xaa Xaa Xaa Xaa Ile Glu Val Phe His Ile Cys Leu
        115                 120                 125

Arg Arg His Ala Val Ile Asn Val Asp Gly Leu Gln Phe Glu Thr Tyr
    130                 135                 140

<210> SEQ ID NO 96
<211> LENGTH: 125
<212> TYPE: PRT
<213> ORGANISM: Silicibacter pomeroyi
<220> FEATURE:
<221> NAME/KEY: misc_feature
<222> LOCATION: (31)..(49)
<223> OTHER INFORMATION: Xaa can be any naturally occurring amino acid
<220> FEATURE:
<221> NAME/KEY: misc_feature
<222> LOCATION: (60)..(60)
```

<223> OTHER INFORMATION: Xaa can be any naturally occurring amino acid
<220> FEATURE:
<221> NAME/KEY: misc_feature
<222> LOCATION: (75)..(86)
<223> OTHER INFORMATION: Xaa can be any naturally occurring amino acid
<220> FEATURE:
<221> NAME/KEY: misc_feature
<222> LOCATION: (102)..(108)
<223> OTHER INFORMATION: Xaa can be any naturally occurring amino acid

<400> SEQUENCE: 96

```
Gly Leu Pro Ala Gly Thr Met Leu Glu Thr Glu Ala Gly Trp Ser Pro
1               5                   10                  15

Val Glu Glu Ile Arg Pro Gly Thr Arg Val Ala Thr Ile Asp Xaa Xaa
            20                  25                  30

Xaa Xaa Xaa Xaa Xaa Xaa Xaa Xaa Xaa Xaa Xaa Xaa Xaa Xaa
        35                  40                  45

Xaa Leu Trp Arg Ile Pro Gly Gly Thr Leu Gly Xaa Cys Ser Asp Leu
    50                  55                  60

Leu Leu Pro Glu Gly His Phe Leu Ala Leu Xaa Xaa Xaa Xaa Xaa
65                  70                  75                  80

Xaa Xaa Xaa Xaa Xaa Xaa Thr Val Leu Ala Pro Val Ala Ala Leu Ala
            85                  90                  95

Gly Phe Glu Gly Ile Xaa Xaa Xaa Xaa Xaa Xaa Xaa Leu Pro Ala His
            100                 105                 110

Ser Leu Arg Phe Ala Glu Glu Glu Val Val Trp Ala Gln
        115                 120                 125
```

<210> SEQ ID NO 97
<211> LENGTH: 126
<212> TYPE: PRT
<213> ORGANISM: Silicibacter pomeroyi
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(47)
<223> OTHER INFORMATION: Xaa can be any naturally occurring amino acid
<220> FEATURE:
<221> NAME/KEY: misc_feature
<222> LOCATION: (58)..(61)
<223> OTHER INFORMATION: Xaa can be any naturally occurring amino acid
<220> FEATURE:
<221> NAME/KEY: misc_feature
<222> LOCATION: (76)..(87)
<223> OTHER INFORMATION: Xaa can be any naturally occurring amino acid
<220> FEATURE:
<221> NAME/KEY: misc_feature
<222> LOCATION: (103)..(109)
<223> OTHER INFORMATION: Xaa can be any naturally occurring amino acid

<400> SEQUENCE: 97

```
Gly Phe Leu Ala Gly Thr Ile Leu Leu Thr Gln Asp Gly Glu Met Pro
1               5                   10                  15

Val Glu Phe Leu Ser Pro Gly Asp Arg Ile Ile Thr Arg Asp Xaa Xaa
            20                  25                  30

Xaa Val Pro Leu His His Ile Thr Arg Ala Pro Gln Xaa Xaa Xaa Ala
        35                  40                  45

Ile Arg Ile Ala Ala Gly Ser Leu Gly Xaa Xaa Xaa Xaa Asp Cys Asp
    50                  55                  60

Leu Ile Leu Pro Ala Gly Gln Pro Val Leu Ile Xaa Xaa Xaa Xaa Xaa
65                  70                  75                  80
```

```
Xaa Xaa Xaa Xaa Xaa Xaa Xaa Gln Ala Met Val Arg Ala Asp Ala Leu
                85                  90                  95

Val Asp Gly Glu Phe Ile Xaa Xaa Xaa Xaa Xaa Xaa Met Gln Leu
            100                 105                 110

Phe Gln Leu His Phe Asp Ser Ala His Val Leu Tyr Ala Gly
        115                 120                 125

<210> SEQ ID NO 98
<211> LENGTH: 132
<212> TYPE: PRT
<213> ORGANISM: Silicibacter pomeroyi
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(55)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (81)..(92)
<223> OTHER INFORMATION: Xaa can be any naturally occurring amino acid
<220> FEATURE:
<221> NAME/KEY: misc_feature
<222> LOCATION: (108)..(115)
<223> OTHER INFORMATION: Xaa can be any naturally occurring amino acid

<400> SEQUENCE: 98

Gly Leu Leu Ala Gly Thr Ser Val Ala Ser Asn Phe Gly Trp Gln Pro
1               5                   10                  15

Val Glu Ala Leu Lys Val Gly Asp Lys Val Leu Thr Phe Asp Xaa Xaa
            20                  25                  30

Xaa Gln Thr Val Ala Asp Ile Gln Arg Glu Thr Val Xaa Xaa Xaa Xaa
        35                  40                  45

Xaa Xaa Xaa Xaa Xaa Xaa Xaa Pro Val Arg Leu Pro Glu Gly Val Cys
    50                  55                  60

His Xaa Arg Arg Asp Leu Trp Met Met Pro Asp Gln Gly Leu Leu Val
65                  70                  75                  80

Xaa Xaa Xaa Xaa Xaa Xaa Xaa Xaa Xaa Xaa Xaa Tyr Ala Val Val
                85                  90                  95

Pro Ala Arg Met Leu Arg Gly Tyr Arg Gly Ile Xaa Xaa Xaa Xaa Xaa
            100                 105                 110

Xaa Xaa Xaa Val Glu Val Thr Thr Leu Ala Phe His Gln Asp Glu Val
        115                 120                 125

Ile Tyr Val Glu
    130

<210> SEQ ID NO 99
<211> LENGTH: 134
<212> TYPE: PRT
<213> ORGANISM: Rhizobium leguminosarum
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(56)
<223> OTHER INFORMATION: Xaa can be any naturally occurring amino acid
<220> FEATURE:
<221> NAME/KEY: misc_feature
```

```
<222> LOCATION: (67)..(70)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (101)..(110)
<223> OTHER INFORMATION: Xaa can be any naturally occurring amino acid

<400> SEQUENCE: 99

Cys Phe Leu Arg Gly Thr Ala Ile Leu Thr Asp Cys Gly Glu Lys Pro
1               5                   10                  15

Val Glu Asn Leu Ser Ile Gly Asp Arg Val Ala Leu Pro Asp Xaa Xaa
            20                  25                  30

Xaa Arg Pro Ile Lys Trp Val Gly Arg Gln Ser Phe Xaa Xaa Xaa Xaa
        35                  40                  45

Xaa Xaa Xaa Xaa Xaa Xaa Xaa Xaa Pro Ile Arg Val Ser Arg His Ala
    50                  55                  60

Leu Asp Xaa Xaa Xaa Xaa His Ser Asp Leu Tyr Leu Ser Pro Gly His
65                  70                  75                  80

Ala Leu Tyr Leu Xaa Gly Ile Leu Ile Gln Val Lys Asp Leu Val Asn
                85                  90                  95

Gly Lys Thr Ile Xaa Xaa Xaa Xaa Xaa Xaa Xaa Xaa Xaa Xaa Ile Glu
            100                 105                 110

Tyr Tyr Ala Val Met Leu Asp Thr His Glu Val Ile Leu Ala Gly Gly
        115                 120                 125

Ala Glu Thr Glu Ser Phe
    130

<210> SEQ ID NO 100
<211> LENGTH: 138
<212> TYPE: PRT
<213> ORGANISM: Magnetospirillum magnetotacticum
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(56)
<223> OTHER INFORMATION: Xaa can be any naturally occurring amino acid
<220> FEATURE:
<221> NAME/KEY: misc_feature
<222> LOCATION: (67)..(70)
<223> OTHER INFORMATION: Xaa can be any naturally occurring amino acid
<220> FEATURE:
<221> NAME/KEY: misc_feature
<222> LOCATION: (85)..(92)
<223> OTHER INFORMATION: Xaa can be any naturally occurring amino acid
<220> FEATURE:
<221> NAME/KEY: misc_feature
<222> LOCATION: (108)..(114)
<223> OTHER INFORMATION: Xaa can be any naturally occurring amino acid

<400> SEQUENCE: 100

Cys Tyr Val Thr Gly Thr Arg Ile Arg Thr Glu Arg Gly Glu Ile Ala
1               5                   10                  15

Val Glu Asp Leu Gln Val Gly Asp Phe Ala Val Thr Ala Ser Xaa Xaa
            20                  25                  30

Xaa Arg Pro Ile Thr Trp Ile Gly His Arg Glu Ile Xaa Xaa Xaa Xaa
        35                  40                  45

Xaa Xaa Xaa Xaa Xaa Xaa Xaa Xaa Pro Val Arg Val Arg Ala Gly Ala
    50                  55                  60
```

Phe Gly Xaa Xaa Xaa Val Asn Asp Leu Phe Leu Ser Pro Gly His
65                  70                  75                  80

Pro Val Leu Val Xaa Xaa Xaa Xaa Xaa Xaa Xaa Gly Val Leu Val
                85                  90                  95

Pro Val Met Cys Leu Ile Asn Gly Thr Thr Ile Xaa Xaa Xaa Xaa
            100                 105                 110

Xaa Xaa Val Thr Tyr Trp His Val Glu Leu Asp Ala His Asp Ile Leu
        115                 120                 125

Leu Ala Glu Gly Leu Pro Ala Glu Ser Tyr
    130                 135

<210> SEQ ID NO 101
<211> LENGTH: 138
<212> TYPE: PRT
<213> ORGANISM: Magnetospirillum magnetotacticum
<220> FEATURE:
<221> NAME/KEY: misc_feature
<222> LOCATION: (31)..(33)
<223> OTHER INFORMATION: Xaa can be any naturally occurring amino acid
<220> FEATURE:
<221> NAME/KEY: misc_feature
<222> LOCATION: (45)..(56)
<223> OTHER INFORMATION: Xaa can be any naturally occurring amino acid
<220> FEATURE:
<221> NAME/KEY: misc_feature
<222> LOCATION: (67)..(70)
<223> OTHER INFORMATION: Xaa can be any naturally occurring amino acid
<220> FEATURE:
<221> NAME/KEY: misc_feature
<222> LOCATION: (85)..(92)
<223> OTHER INFORMATION: Xaa can be any naturally occurring amino acid
<220> FEATURE:
<221> NAME/KEY: misc_feature
<222> LOCATION: (108)..(114)
<223> OTHER INFORMATION: Xaa can be any naturally occurring amino acid

<400> SEQUENCE: 101

Cys Phe Val Ser Gly Thr Arg Ile Ser Val Glu Arg Gly Ser Ile Pro
1               5                   10                  15

Val Glu Leu Leu Arg Ile Gly Glu Lys Ala Arg Leu Ala Ser Xaa Xaa
                20                  25                  30

Xaa Arg Thr Ile Thr Trp Ile Gly His Arg Glu Ile Xaa Xaa Xaa Xaa
            35                  40                  45

Xaa Xaa Xaa Xaa Xaa Xaa Xaa Xaa Pro Val Arg Val Arg Ala Gly Ala
        50                  55                  60

Phe Gly Xaa Xaa Xaa Xaa Ala Arg Asp Leu Phe Leu Ser Pro Gly His
65                  70                  75                  80

Pro Val Leu Ile Xaa Xaa Xaa Xaa Xaa Xaa Xaa Gly Val Leu Val
                85                  90                  95

Pro Val Met Cys Leu Ile Asn Gly Thr Ser Ile Xaa Xaa Xaa Xaa Xaa
            100                 105                 110

Xaa Xaa Val Thr Tyr Trp His Val Glu Leu Asp Arg His Asp Ile Leu
        115                 120                 125

Leu Ala Glu Gly Leu Pro Ala Glu Ser Tyr
    130                 135

<210> SEQ ID NO 102
<211> LENGTH: 98
<212> TYPE: PRT
<213> ORGANISM: Magnetospirillum magnetotacticum
<220> FEATURE:
<221> NAME/KEY: misc_feature
<222> LOCATION: (31)..(33)

```
<223> OTHER INFORMATION: Xaa can be any naturally occurring amino acid
<220> FEATURE:
<221> NAME/KEY: misc_feature
<222> LOCATION: (45)..(56)
<223> OTHER INFORMATION: Xaa can be any naturally occurring amino acid
<220> FEATURE:
<221> NAME/KEY: misc_feature
<222> LOCATION: (67)..(70)
<223> OTHER INFORMATION: Xaa can be any naturally occurring amino acid
<220> FEATURE:
<221> NAME/KEY: misc_feature
<222> LOCATION: (85)..(92)
<223> OTHER INFORMATION: Xaa can be any naturally occurring amino acid

<400> SEQUENCE: 102

Cys Phe Val Thr Gly Thr Met Ile Ala Thr Ala Arg Gly Glu Val Ala
1               5                   10                  15

Val Glu Asp Leu Arg Ala Gly Asp Phe Ala Arg Thr Ala Glu Xaa Xaa
            20                  25                  30

Xaa Arg Pro Ile Val Trp Ile Gly His Arg Glu Ile Xaa Xaa Xaa Xaa
        35                  40                  45

Xaa Xaa Xaa Xaa Xaa Xaa Xaa Xaa Pro Val Arg Val Arg Thr Gly Ala
    50                  55                  60

Phe Gly Xaa Xaa Xaa Xaa Ala Arg Asp Leu Tyr Leu Ser Pro Gly His
65                  70                  75                  80

Pro Val Leu Val Xaa Xaa Xaa Xaa Xaa Xaa Xaa Gly Thr Leu Val
                85                  90                  95

Pro Ile

<210> SEQ ID NO 103
<211> LENGTH: 24
<212> TYPE: PRT
<213> ORGANISM: Magnetospirillum magnetotacticum

<400> SEQUENCE: 103

Val Thr Tyr Trp His Val Glu Leu Asp Ala His Asp Ile Leu Leu Ala
1               5                   10                  15

Glu Gly Leu Pro Ala Glu Ser Tyr
            20

<210> SEQ ID NO 104
<211> LENGTH: 7
<212> TYPE: PRT
<213> ORGANISM: Magnetospirillum magnetotacticum

<400> SEQUENCE: 104

Arg Leu Pro Ala Glu Ser Tyr
1               5

<210> SEQ ID NO 105
<211> LENGTH: 57
<212> TYPE: PRT
<213> ORGANISM: artificial sequence
<220> FEATURE:
<223> OTHER INFORMATION: Type B BIL domain consensus sequence
<220> FEATURE:
<221> NAME/KEY: misc_feature
<222> LOCATION: (1)..(1)
<223> OTHER INFORMATION: C, S, or P
<220> FEATURE:
<221> NAME/KEY: misc_feature
<222> LOCATION: (2)..(2)
<223> OTHER INFORMATION: F, L, or V
<220> FEATURE:
<221> NAME/KEY: misc_feature
<222> LOCATION: (3)..(4)
```

```
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: G, S, W, D, or T
<220> FEATURE:
<221> NAME/KEY: misc_feature
<222> LOCATION: (6)..(6)
<223> OTHER INFORMATION: T, E, S, A, or M
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: V, I, L, or M
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: T, M, L, or K
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: G or N
<220> FEATURE:
<221> NAME/KEY: misc_feature
<222> LOCATION: (14)..(14)
<223> OTHER INFORMATION: 0-100 amino acids of any kind
<220> FEATURE:
<221> NAME/KEY: misc_feature
<222> LOCATION: (15)..(15)
<223> OTHER INFORMATION: I, V, A, or L
<220> FEATURE:
<221> NAME/KEY: misc_feature
<222> LOCATION: (16)..(16)
<223> OTHER INFORMATION: E, A, D, G, or S
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: I, L, V, or F
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: D, E, or M
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: V or I
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: A, S, T, or  G
<220> FEATURE:
<221> NAME/KEY: misc_feature
```

```
<222> LOCATION: (27)..(27)
<223> OTHER INFORMATION: 0-100 amino acids of any kind
<220> FEATURE:
<221> NAME/KEY: misc_feature
<222> LOCATION: (28)..(28)
<223> OTHER INFORMATION: L, I, F, or V
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: S, T, V, A, V, or L
<220> FEATURE:
<221> NAME/KEY: misc_feature
<222> LOCATION: (31)..(31)
<223> OTHER INFORMATION: T, N, or S
<220> FEATURE:
<221> NAME/KEY: misc_feature
<222> LOCATION: (32)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: P, L, or R
<220> FEATURE:
<221> NAME/KEY: misc_feature
<222> LOCATION: (36)..(36)
<223> OTHER INFORMATION: F, I, W, Y, or V
<220> FEATURE:
<221> NAME/KEY: misc_feature
<222> LOCATION: (37)..(37)
<223> OTHER INFORMATION: 0-200 amino acids of any kind
<220> FEATURE:
<221> NAME/KEY: misc_feature
<222> LOCATION: (38)..(38)
<223> OTHER INFORMATION: A, V, T, or M
<220> FEATURE:
<221> NAME/KEY: misc_feature
<222> LOCATION: (39)..(39)
<223> OTHER INFORMATION: Y, F, H, or M
<220> FEATURE:
<221> NAME/KEY: misc_feature
<222> LOCATION: (40)..(40)
<223> OTHER INFORMATION: N, D, R, or K
<220> FEATURE:
<221> NAME/KEY: misc_feature
<222> LOCATION: (41)..(41)
<223> OTHER INFORMATION: L, F, I, or M
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: V, I, or L
<220> FEATURE:
<221> NAME/KEY: misc_feature
<222> LOCATION: (44)..(46)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: T, S, N, or E
<220> FEATURE:
<221> NAME/KEY: misc_feature
<222> LOCATION: (48)..(48)
<223> OTHER INFORMATION: T, S, N, or E
<220> FEATURE:
<221> NAME/KEY: misc_feature
<222> LOCATION: (49)..(49)
<223> OTHER INFORMATION: Y, F, or L
<220> FEATURE:
<221> NAME/KEY: misc_feature
<222> LOCATION: (50)..(50)
<223> OTHER INFORMATION: Xaa can be any naturally occurring amino acid
<220> FEATURE:
```

```
<221> NAME/KEY: misc_feature
<222> LOCATION: (51)..(51)
<223> OTHER INFORMATION: V, A, or I
<220> FEATURE:
<221> NAME/KEY: misc_feature
<222> LOCATION: (52)..(52)
<223> OTHER INFORMATION: 0-100 amino acids of any kind
<220> FEATURE:
<221> NAME/KEY: misc_feature
<222> LOCATION: (53)..(53)
<223> OTHER INFORMATION: W, L, V, or Y
<220> FEATURE:
<221> NAME/KEY: misc_feature
<222> LOCATION: (54)..(54)
<223> OTHER INFORMATION: V, A, or S
<220> FEATURE:
<221> NAME/KEY: misc_feature
<222> LOCATION: (56)..(56)
<223> OTHER INFORMATION: N or D
<220> FEATURE:
<221> NAME/KEY: misc_feature
<222> LOCATION: (57)..(57)
<223> OTHER INFORMATION: Xaa can be any naturally occurring amino acid

<400> SEQUENCE: 105

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Gly Xaa Xaa Xaa Xaa Xaa Xaa Xaa Xaa Xaa Xaa Xaa
            20                  25                  30

Xaa His Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa His Xaa Xaa
    50                  55

<210> SEQ ID NO 106
<211> LENGTH: 88
<212> TYPE: PRT
<213> ORGANISM: artificial sequence
<220> FEATURE:
<223> OTHER INFORMATION: Type B BIL domain consensus sequence
<220> FEATURE:
<221> NAME/KEY: misc_feature
<222> LOCATION: (1)..(1)
<223> OTHER INFORMATION: C, G, A or S
<220> FEATURE:
<221> NAME/KEY: misc_feature
<222> LOCATION: (2)..(2)
<223> OTHER INFORMATION: F, L or Y
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: G, E, S or T
<220> FEATURE:
<221> NAME/KEY: misc_feature
<222> LOCATION: (6)..(6)
<223> OTHER INFORMATION: T or S
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: I, V or L
<220> FEATURE:
<221> NAME/KEY: misc_feature
<222> LOCATION: (9)..(12)
<223> OTHER INFORMATION: Xaa can be any naturally occurring amino acid
<220> FEATURE:
<221> NAME/KEY: misc_feature
```

-continued

```
<222> LOCATION: (14)..(14)
<223> OTHER INFORMATION: 0-100 amino acids of any kind
<220> FEATURE:
<221> NAME/KEY: misc_feature
<222> LOCATION: (15)..(15)
<223> OTHER INFORMATION: V, I, A or L
<220> FEATURE:
<221> NAME/KEY: misc_feature
<222> LOCATION: (16)..(16)
<223> OTHER INFORMATION: E, S, A or D
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: L or I
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: G, E or N
<220> FEATURE:
<221> NAME/KEY: misc_feature
<222> LOCATION: (22)..(22)
<223> OTHER INFORMATION: D, E, A, Q or T
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: V, I, A, L or M
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: T, V, L or A
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: D, S, E or T
<220> FEATURE:
<221> NAME/KEY: misc_feature
<222> LOCATION: (29)..(29)
<223> OTHER INFORMATION: 0-100 amino acids of any kind
<220> FEATURE:
<221> NAME/KEY: misc_feature
<222> LOCATION: (30)..(30)
<223> OTHER INFORMATION: P, L, A or M
<220> FEATURE:
<221> NAME/KEY: misc_feature
<222> LOCATION: (31)..(31)
<223> OTHER INFORMATION: V, I, L, T or W
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: I, L, V, F or M
<220> FEATURE:
<221> NAME/KEY: misc_feature
<222> LOCATION: (34)..(38)
<223> OTHER INFORMATION: Xaa can be any naturally occurring amino acid
<220> FEATURE:
```

```
<221> NAME/KEY: misc_feature
<222> LOCATION: (39)..(39)
<223> OTHER INFORMATION: A, D, G, H, K, N, Q or S
<220> FEATURE:
<221> NAME/KEY: misc_feature
<222> LOCATION: (40)..(40)
<223> OTHER INFORMATION: 0-100 amino acids of any kind
<220> FEATURE:
<221> NAME/KEY: misc_feature
<222> LOCATION: (41)..(41)
<223> OTHER INFORMATION: A, C, D, E, F, G, H, L, M, Q, R, S, T, V or Y
<220> FEATURE:
<221> NAME/KEY: misc_feature
<222> LOCATION: (42)..(42)
<223> OTHER INFORMATION: A, C, E, G, H, K, L, N, Q, R, S or T
<220> FEATURE:
<221> NAME/KEY: misc_feature
<222> LOCATION: (43)..(43)
<223> OTHER INFORMATION: A, D, E, G, N, P or T
<220> FEATURE:
<221> NAME/KEY: misc_feature
<222> LOCATION: (44)..(44)
<223> OTHER INFORMATION: I, L, M, R or V
<220> FEATURE:
<221> NAME/KEY: misc_feature
<222> LOCATION: (45)..(45)
<223> OTHER INFORMATION: F, I, L, M, Q, R, V, W or Y
<220> FEATURE:
<221> NAME/KEY: misc_feature
<222> LOCATION: (46)..(46)
<223> OTHER INFORMATION: A, L, M or V
<220> FEATURE:
<221> NAME/KEY: misc_feature
<222> LOCATION: (47)..(47)
<223> OTHER INFORMATION: A, G, L, M, P, S, or T
<220> FEATURE:
<221> NAME/KEY: misc_feature
<222> LOCATION: (48)..(48)
<223> OTHER INFORMATION: A, E, G, H, P, Q or S
<220> FEATURE:
<221> NAME/KEY: misc_feature
<222> LOCATION: (49)..(49)
<223> OTHER INFORMATION: D, E, G, H, L, N, Q, R or S
<220> FEATURE:
<221> NAME/KEY: misc_feature
<222> LOCATION: (50)..(50)
<223> OTHER INFORMATION: A, H, Q or T
<220> FEATURE:
<221> NAME/KEY: misc_feature
<222> LOCATION: (51)..(51)
<223> OTHER INFORMATION: A, C, F, G, P, Q or R
<220> FEATURE:
<221> NAME/KEY: misc_feature
<222> LOCATION: (52)..(52)
<223> OTHER INFORMATION: F, I, L, M or V
<220> FEATURE:
<221> NAME/KEY: misc_feature
<222> LOCATION: (53)..(53)
<223> OTHER INFORMATION: A, C, F, L, V or Y
<220> FEATURE:
<221> NAME/KEY: misc_feature
<222> LOCATION: (54)..(54)
<223> OTHER INFORMATION: A, F, I, L, M, T, V or W
<220> FEATURE:
<221> NAME/KEY: misc_feature
<222> LOCATION: (55)..(55)
<223> OTHER INFORMATION: 0-100 amino acids of any kind
<220> FEATURE:
<221> NAME/KEY: misc_feature
<222> LOCATION: (56)..(56)
<223> OTHER INFORMATION: A, D, E, G, L, P, Q, S, T or Y
<220> FEATURE:
<221> NAME/KEY: misc_feature
<222> LOCATION: (57)..(57)
<223> OTHER INFORMATION: A, F, I, K, L, M, R, T or V
<220> FEATURE:
<221> NAME/KEY: misc_feature
<222> LOCATION: (58)..(58)
<223> OTHER INFORMATION: D, F, L, M or V
```

```
-continued

<220> FEATURE:
<221> NAME/KEY: misc_feature
<222> LOCATION: (59)..(59)
<223> OTHER INFORMATION: A, I, L, T or V
<220> FEATURE:
<221> NAME/KEY: misc_feature
<222> LOCATION: (60)..(60)
<223> OTHER INFORMATION: A, K, M, P, Q or R
<220> FEATURE:
<221> NAME/KEY: misc_feature
<222> LOCATION: (61)..(61)
<223> OTHER INFORMATION: A, I or V
<220> FEATURE:
<221> NAME/KEY: misc_feature
<222> LOCATION: (62)..(62)
<223> OTHER INFORMATION: A, C, D, E, G, H, I, K, L, M, Q, R, T or V
<220> FEATURE:
<221> NAME/KEY: misc_feature
<222> LOCATION: (63)..(63)
<223> OTHER INFORMATION: A, C, D, F, H, M, R, T or V
<220> FEATURE:
<221> NAME/KEY: misc_feature
<222> LOCATION: (64)..(64)
<223> OTHER INFORMATION: A, F, L or M
<220> FEATURE:
<221> NAME/KEY: misc_feature
<222> LOCATION: (65)..(65)
<223> OTHER INFORMATION: A, G, I, L, R, T or V
<220> FEATURE:
<221> NAME/KEY: misc_feature
<222> LOCATION: (66)..(66)
<223> OTHER INFORMATION: A, D, G, L, N or P
<220> FEATURE:
<221> NAME/KEY: misc_feature
<222> LOCATION: (67)..(67)
<223> OTHER INFORMATION: A, D, F, G, H, K, L, N, P, Q, S, T or Y
<220> FEATURE:
<221> NAME/KEY: misc_feature
<222> LOCATION: (68)..(68)
<223> OTHER INFORMATION: A, D, E, G, H, I, M, N, P, Q, R, S, T or K
<220> FEATURE:
<221> NAME/KEY: misc_feature
<222> LOCATION: (69)..(69)
<223> OTHER INFORMATION: A, D, E, F, G, H, L, M, Q, R, S, T or W
<220> FEATURE:
<221> NAME/KEY: misc_feature
<222> LOCATION: (70)..(70)
<223> OTHER INFORMATION: A, G, I, P, T or V
<220> FEATURE:
<221> NAME/KEY: misc_feature
<222> LOCATION: (71)..(71)
<223> OTHER INFORMATION: 0-100 amino acids of any kind
<220> FEATURE:
<221> NAME/KEY: misc_feature
<222> LOCATION: (72)..(72)
<223> OTHER INFORMATION: A, I, L, M, Q, T, V or Y
<220> FEATURE:
<221> NAME/KEY: misc_feature
<222> LOCATION: (73)..(73)
<223> OTHER INFORMATION: D, E, K, L, P, Q, R, S, T or V
<220> FEATURE:
<221> NAME/KEY: misc_feature
<222> LOCATION: (74)..(74)
<223> OTHER INFORMATION: A, I, L, V, W or Y
<220> FEATURE:
<221> NAME/KEY: misc_feature
<222> LOCATION: (75)..(75)
<223> OTHER INFORMATION: A, F, H, I, L, M, T, V, W or Y
<220> FEATURE:
<221> NAME/KEY: misc_feature
<222> LOCATION: (76)..(76)
<223> OTHER INFORMATION: A, G, H, N, Q, R, S or T
<220> FEATURE:
<221> NAME/KEY: misc_feature
<222> LOCATION: (77)..(77)
<223> OTHER INFORMATION: F, I, L, M or V
<220> FEATURE:
<221> NAME/KEY: misc_feature
<222> LOCATION: (78)..(78)
```

```
<223> OTHER INFORMATION: A, C, E, H, L, M, R, T or V
<220> FEATURE:
<221> NAME/KEY: misc_feature
<222> LOCATION: (79)..(79)
<223> OTHER INFORMATION: F, L, M or T
<220> FEATURE:
<221> NAME/KEY: misc_feature
<222> LOCATION: (80)..(80)
<223> OTHER INFORMATION: A, D, E, H, P, Q or R
<220> FEATURE:
<221> NAME/KEY: misc_feature
<222> LOCATION: (81)..(81)
<223> OTHER INFORMATION: A, C, D, E, G, H, N, Q, R, S or T
<220> FEATURE:
<221> NAME/KEY: misc_feature
<222> LOCATION: (82)..(82)
<223> OTHER INFORMATION: A, D, E, H, N or P
<220> FEATURE:
<221> NAME/KEY: misc_feature
<222> LOCATION: (83)..(83)
<223> OTHER INFORMATION: A, D, E, G, H, L, Q or S
<220> FEATURE:
<221> NAME/KEY: misc_feature
<222> LOCATION: (84)..(84)
<223> OTHER INFORMATION: A, I, L, M, S or V
<220> FEATURE:
<221> NAME/KEY: misc_feature
<222> LOCATION: (85)..(85)
<223> OTHER INFORMATION: I, L, M or V
<220> FEATURE:
<221> NAME/KEY: misc_feature
<222> LOCATION: (86)..(86)
<223> OTHER INFORMATION: F, L, N, R, S, T, V, W or Y
<220> FEATURE:
<221> NAME/KEY: misc_feature
<222> LOCATION: (87)..(87)
<223> OTHER INFORMATION: A, G, S, T or V
<220> FEATURE:
<221> NAME/KEY: misc_feature
<222> LOCATION: (88)..(88)
<223> OTHER INFORMATION: A, D, E, G, H, N, Q or S

<400> SEQUENCE: 106

Xaa Xaa Xaa Xaa Xaa Xaa Xaa Xaa Xaa Xaa Xaa Gly Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa
            85

<210> SEQ ID NO 107
<211> LENGTH: 149
<212> TYPE: PRT
<213> ORGANISM: Pseudomonas syringae

<400> SEQUENCE: 107

Cys Phe Ala Ala Gly Thr Met Val Ser Thr Pro Asp Gly Glu Arg Ala
1               5                   10                  15

Ile Asp Thr Leu Lys Val Gly Asp Ile Val Trp Ser Lys Pro Glu Gly
            20                  25                  30

Gly Gly Lys Pro Phe Ala Ala Ala Ile Leu Ala Thr His Ile Arg Thr
        35                  40                  45
```

```
Asp Gln Pro Ile Tyr Arg Leu Lys Leu Lys Gly Lys Gln Glu Asn Gly
        50                  55                  60

Gln Ala Glu Asp Glu Ser Leu Leu Val Thr Pro Gly His Pro Phe Tyr
 65                  70                  75                  80

Val Pro Ala Gln His Gly Phe Val Pro Val Ile Asp Leu Lys Pro Gly
                85                  90                  95

Asp Arg Leu Gln Ser Leu Ala Asp Gly Ala Ser Glu Asn Thr Ser Ser
                100                 105                 110

Glu Val Glu Ser Leu Glu Leu Tyr Leu Pro Val Gly Lys Thr Tyr Asn
            115                 120                 125

Leu Thr Val Asp Val Gly His Thr Phe Tyr Val Gly Lys Leu Lys Thr
        130                 135                 140

Trp Val His Asn Thr
145

<210> SEQ ID NO 108
<211> LENGTH: 461
<212> TYPE: PRT
<213> ORGANISM: artificial sequence
<220> FEATURE:
<223> OTHER INFORMATION: MBP-CBD splicing product

<400> SEQUENCE: 108

Met Lys Thr Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
                20                  25                  30

Gly Ile Lys Val Thr Val Glu His Pro Asp Lys Leu Glu Glu Lys Phe
            35                  40                  45

Pro Gln Val Ala Ala Thr Gly Asp Gly Pro Asp Ile Ile Phe Trp Ala
        50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
                100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
        130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Phe Leu
                180                 185                 190

Val Asp Leu Ile Ala Gly Leu Thr Lys Asn Lys His Met Asn Ala Asp
            195                 200                 205

Thr Asp Tyr Ser Ile Ala Glu Ala Ala Phe Asn Lys Gly Glu Thr Ala
        210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255
```

-continued

```
Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
    370                 375                 380

Glu Gly Arg Ile Ser Glu Phe Gly Ser Thr Ser Arg Val Asp Cys Gly
385                 390                 395                 400

Gly Leu Thr Gly Leu Asn Ser Gly Leu Thr Thr Asn Pro Gly Val Ser
                405                 410                 415

Ala Trp Gln Val Asn Thr Ala Tyr Thr Ala Gly Gln Leu Val Thr Tyr
            420                 425                 430

Asn Gly Lys Thr Tyr Lys Cys Leu Gln Pro His Thr Ser Leu Ala Gly
        435                 440                 445

Trp Glu Pro Ser Asn Val Pro Ala Leu Trp Gln Leu Gln
    450                 455                 460

<210> SEQ ID NO 109
<211> LENGTH: 541
<212> TYPE: PRT
<213> ORGANISM: artificial sequence
<220> FEATURE:
<223> OTHER INFORMATION: MBP-PsyBIL carboxy terminal cleavage product

<400> SEQUENCE: 109

Met Lys Thr Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160
```

-continued

```
Leu Ile Ala Ala Asp Gly Gly Tyr Ala Phe Lys Tyr Glu Asn Gly Lys
                165                 170                 175
Tyr Asp Ile Lys Asp Val Gly Val Asp Asn Ala Gly Ala Lys Ala Gly
            180                 185                 190
Leu Thr Phe Leu Val Asp Leu Ile Lys Asn Lys His Met Asn Ala Asp
        195                 200                 205
Thr Asp Tyr Ser Ile Ala Glu Ala Ala Phe Asn Lys Gly Glu Thr Ala
    210                 215                 220
Met Thr Ile Asn Gly Pro Trp Ala Trp Ser Asn Ile Asp Thr Ser Lys
225                 230                 235                 240
Val Asn Tyr Gly Val Thr Val Leu Pro Thr Phe Lys Gly Gln Pro Ser
                245                 250                 255
Lys Pro Phe Val Gly Val Leu Ser Ala Gly Ile Asn Ala Ala Ser Pro
            260                 265                 270
Asn Lys Glu Leu Ala Lys Glu Phe Leu Glu Asn Tyr Leu Leu Thr Asp
        275                 280                 285
Glu Gly Leu Glu Ala Val Asn Lys Asp Lys Pro Leu Gly Ala Val Ala
    290                 295                 300
Leu Lys Ser Tyr Glu Glu Leu Ala Lys Asp Pro Arg Ile Ala Ala
305                 310                 315                 320
Thr Met Glu Asn Ala Gln Lys Gly Glu Ile Met Pro Asn Ile Pro Gln
                325                 330                 335
Met Ser Ala Phe Trp Tyr Ala Val Arg Thr Ala Val Ile Asn Ala Ala
            340                 345                 350
Ser Gly Arg Gln Thr Val Asp Glu Ala Leu Lys Asp Ala Gln Thr Asn
        355                 360                 365
Ser Ser Ser Asn Asn Asn Asn Asn Asn Asn Asn Asn Leu Gly Ile
    370                 375                 380
Glu Gly Arg Ile Ser Glu Phe Gly Ser Cys Phe Ala Ala Gly Thr Met
385                 390                 395                 400
Val Ser Thr Pro Asp Gly Glu Arg Ala Ile Asp Thr Leu Lys Val Gly
                405                 410                 415
Asp Ile Val Trp Ser Lys Pro Glu Gly Gly Lys Pro Phe Ala Ala
            420                 425                 430
Ala Ile Leu Ala Thr His Ile Arg Thr Asp Gln Pro Ile Tyr Arg Leu
        435                 440                 445
Lys Leu Lys Gly Lys Gln Glu Asn Gly Gln Ala Glu Asp Glu Ser Leu
    450                 455                 460
Leu Val Thr Pro Gly His Pro Phe Tyr Val Pro Ala Gln His Gly Phe
465                 470                 475                 480
Val Pro Val Ile Asp Leu Lys Pro Gly Asp Arg Leu Gln Ser Leu Ala
                485                 490                 495
Asp Gly Ala Ser Glu Asn Thr Ser Ser Glu Val Glu Ser Leu Glu Leu
            500                 505                 510
Tyr Leu Pro Val Gly Lys Thr Tyr Asn Leu Thr Val Asp Val Gly His
        515                 520                 525
Thr Phe Tyr Val Gly Lys Leu Lys Thr Trp Val His Asn
    530                 535                 540
```

What is claimed is:

1. A chimeric polypeptide comprising an autoprocessing segment having the amino acid sequence set forth by SEQ ID NO: 31.

2. The chimeric polypeptide of claim 1, wherein a carboxy terminal end of said autoprocessing segment is attached to a first polypeptide segment and further wherein said autoprocessing results in removal of said first polypeptide segment.

3. The chimeric polypeptide of claim 1, wherein said autoprocessing segment is flanked by a first and a second polypeptide segments and further wherein said autoprocessing results in splicing of said first and said second polypeptide segments.

4. The chimeric polypeptide of claim 2, wherein said segment of the polypeptide adjacent to said carboxy terminal end of said autoprocessing segment includes an amino acid residue comprising a nucleophilic group at an amino terminal end thereof.

5. The chimeric polypeptide of claim 4, wherein said nucleophilic group is a hydroxyl group.

6. The chimeric polypeptide of claim 4, wherein said amino acid residue is a threonine residue.

7. The chimeric polypeptide of claim 2, wherein a segment of the chimeric polypeptide adjacent to an amino terminal end of said autoprocessing segment includes a serine amino acid residue at a carboxy terminal end thereof.

8. The chimeric polypeptide of claim 1, wherein said autoprocessing results in auto-splicing.

9. The chimeric polypeptide of claim 8, wherein said auto-splicing is auto-splicing of segments of the polypeptide flanking said autoprocessing segment.

10. The chimeric polypeptide of claim 1, wherein the chimeric polypeptide is active in said autoprocessing under a condition selected from the group consisting of a temperature selected from a range of 33° C. to 41° C., a pH selected from a range of pH 7.8 to pH 8.2, and a concentration of dithiothreitol selected from a range of 0.1 mM to 20 mM.

11. The chimeric polypeptide of claim 1, further comprising an affinity tag capable of specifically binding a molecule.

12. The chimeric polypeptide of claim 11, wherein said affinity tag is a maltose-binding domain or a chitin-binding domain.

13. The chimeric polypeptide of claim 11, wherein said molecule is displayed on a virus or a cell.

14. The chimeric polypeptide of claim 11, wherein said molecule is amylose or chitin.

15. The chimeric polypeptide of claim 13, wherein said virus is a bacteriophage.

* * * * *